US011826585B2

(12) United States Patent
Ebbini et al.

(10) Patent No.: US 11,826,585 B2
(45) Date of Patent: Nov. 28, 2023

(54) ADAPTIVE REFOCUSING OF ULTRASOUND TRANSDUCER ARRAYS USING IMAGE DATA

(71) Applicant: REGENTS OF THE UNIVERSITY OF MINNESOTA, Minneapolis, MN (US)

(72) Inventors: Emad S. Ebbini, Edina, MN (US); Dalong Liu, Sammamish, WA (US); Hasan Aldiabat, Minneapolis, MN (US); Parker O'Brien, Minneapolis, MN (US)

(73) Assignee: REGENTS OF THE UNIVERSITY OF MINNESOTA, Minneapolis, MN (US)

( * ) Notice: Subject to any disclaimer, the term of this patent is extended or adjusted under 35 U.S.C. 154(b) by 0 days.

(21) Appl. No.: 17/949,535

(22) Filed: Sep. 21, 2022

(65) Prior Publication Data
US 2023/0118199 A1  Apr. 20, 2023

Related U.S. Application Data

(63) Continuation of application No. 16/202,992, filed on Nov. 28, 2018, now Pat. No. 11,458,337.
(Continued)

(51) Int. Cl.
*A61N 7/00* (2006.01)
*A61B 8/00* (2006.01)
(Continued)

(52) U.S. Cl.
CPC .............. *A61N 7/00* (2013.01); *A61B 8/0875* (2013.01); *A61B 8/145* (2013.01); *A61B 8/4488* (2013.01);
(Continued)

(58) Field of Classification Search
CPC .... A61N 7/00; A61N 7/02; A61N 2007/0052; A61N 2007/0078; A61N 2007/0095;
(Continued)

(56) References Cited

U.S. PATENT DOCUMENTS

| 5,694,936 A | 12/1997 | Fujimoto |
| 5,906,580 A | 5/1999 | Kline-Schoder |

(Continued)

FOREIGN PATENT DOCUMENTS

| CN | 101179998 A | 5/2008 |
| CN | 102788836 A | 11/2012 |

(Continued)

OTHER PUBLICATIONS

Trahey, Gregg E., John W. Allison, and Olaf T. Von Ramm. "Angle independent ultrasonic detection of blood flow." IEEE Transactions on Biomedical Engineering 12 (1987): 965-967.
(Continued)

*Primary Examiner* — Baisakhi Roy
*Assistant Examiner* — Kaitlyn E Sebastian
(74) *Attorney, Agent, or Firm* — Mueting Raasch Group

(57) ABSTRACT

A dual-mode ultrasound system provides real-time imaging and therapy delivery using a transducer array. The system may use various imaging modes to provide image data that may be used to select control points within an imaging field of view. The control points along with the image data may be used to solve an optimization problem to achieve desired focusing gains at one or more of the control points. The optimized solution may be used to produce excitation waveforms to generate new image data. The focusing gains may be evaluated and the optimization problem may be iterated until desired focusing gains are achieved. Virtual arrays may be defined and cascaded to provide flexibility in solving the optimization problem.

29 Claims, 22 Drawing Sheets

Related U.S. Application Data

(60) Provisional application No. 62/591,308, filed on Nov. 28, 2017.

(51) Int. Cl.
  *A61B 8/14* (2006.01)
  *A61B 8/08* (2006.01)
  *A61N 7/02* (2006.01)
  *A61B 17/22* (2006.01)

(52) U.S. Cl.
  CPC .............. *A61B 8/5207* (2013.01); *A61B 8/54* (2013.01); *A61B 8/565* (2013.01); *A61N 7/02* (2013.01); *A61B 2017/22008* (2013.01); *A61N 2007/0052* (2013.01); *A61N 2007/0078* (2013.01); *A61N 2007/0095* (2013.01)

(58) Field of Classification Search
  CPC ..... A61B 8/0875; A61B 8/145; A61B 8/4488; A61B 8/5207; A61B 8/54; A61B 8/565; A61B 2017/22008
  See application file for complete search history.

(56) References Cited

U.S. PATENT DOCUMENTS

| | | |
|---|---|---|
| 6,172,939 B1 | 1/2001 | Cole |
| 6,277,075 B1 | 8/2001 | Torp |
| 6,318,179 B1 | 11/2001 | Hamilton |
| 6,492,762 B1 | 12/2002 | Pant |
| 6,494,839 B1 | 12/2002 | Averkiou |
| 6,540,677 B1 | 4/2003 | Angelsen ............. B06B 1/0215 310/314 |
| 6,618,493 B1 | 9/2003 | Torp |
| 6,705,993 B2 | 3/2004 | Ebbini ................ G01S 7/52038 600/443 |
| 6,770,031 B2 | 8/2004 | Hynynen et al. |
| 6,951,540 B2 | 10/2005 | Ebbini et al. |
| 7,063,666 B2 | 6/2006 | Weng et al. |
| 7,686,764 B2 | 3/2010 | Watanabe et al. |
| 7,901,358 B2 | 3/2011 | Mehi |
| 8,002,705 B1 | 8/2011 | Napolitano |
| 8,086,296 B2 | 12/2011 | Bystritsky |
| 8,591,419 B2 | 11/2013 | Tyler |
| 8,911,372 B2 | 12/2014 | Yoshikawa et al. |
| 8,939,909 B2 | 1/2015 | Wegner |
| 9,144,693 B2 | 9/2015 | Appelman |
| 9,592,409 B2 | 3/2017 | Yoo |
| 9,610,061 B2 | 4/2017 | Ebbini et al. |
| 10,231,712 B2 | 3/2019 | Ebbini et al. |
| 2001/0017937 A1 | 5/2001 | Bonnefous |
| 2001/0029336 A1 | 10/2001 | Teo |
| 2001/0039381 A1 | 11/2001 | Burns |
| 2003/0036702 A1 | 2/2003 | Davidsen |
| 2003/0097068 A1 | 5/2003 | Hossack |
| 2003/0220636 A1 | 11/2003 | Bowman |
| 2003/0225331 A1 | 12/2003 | Diederich |
| 2004/0015079 A1 | 1/2004 | Berger |
| 2004/0106880 A1 | 6/2004 | Weng |
| 2004/0210135 A1 | 10/2004 | Hynynen |
| 2005/0070796 A1 | 3/2005 | Tsujita |
| 2005/0102009 A1 | 5/2005 | Costantino |
| 2005/0249667 A1 | 11/2005 | Tuszynski |
| 2005/0267453 A1 | 12/2005 | Wong et al. |
| 2007/0016040 A1 | 1/2007 | Nita |
| 2007/0038100 A1 | 2/2007 | Nita |
| 2007/0055155 A1 | 3/2007 | Owen |
| 2007/0129633 A1 | 6/2007 | Lee et al. |
| 2008/0015440 A1 | 1/2008 | Shandas |
| 2008/0027320 A1 | 1/2008 | Bolorforosh |
| 2008/0045882 A1 | 2/2008 | Finsterwald |
| 2008/0221448 A1 | 9/2008 | Khuri-Yakub et al. |
| 2008/0228075 A1 | 9/2008 | Fraser |
| 2009/0048546 A1 | 2/2009 | Appelman et al. |
| 2009/0069677 A1 | 3/2009 | Chen |
| 2009/0069680 A1 | 3/2009 | Yasuhiko |
| 2010/0004540 A1 | 1/2010 | Thiele |
| 2010/0286520 A1 | 11/2010 | Hazard |
| 2011/0112405 A1 | 5/2011 | Barthe |
| 2011/0248714 A1 | 10/2011 | Salomir |
| 2012/0053391 A1 | 3/2012 | Mishelevich |
| 2012/0083692 A1 | 4/2012 | Stoll |
| 2012/0283502 A1 | 8/2012 | Mishelevich |
| 2012/0283564 A1 | 11/2012 | Ebbini |
| 2012/0289869 A1 | 11/2012 | Tyler |
| 2013/0123635 A1 | 5/2013 | Wegner |
| 2013/0144165 A1* | 6/2013 | Ebbini ................. A61B 8/0891 600/439 |
| 2013/0197368 A1 | 8/2013 | Jin |
| 2014/0343463 A1 | 11/2014 | Mishelevich |
| 2015/0251025 A1 | 9/2015 | You |
| 2016/0143617 A1 | 5/2016 | Ebbinl ..................... A61B 8/14 600/447 |
| 2017/0080255 A1 | 3/2017 | Law |
| 2017/0224990 A1 | 8/2017 | Goldwasser |
| 2017/0296140 A1 | 10/2017 | Ebbini |
| 2019/0269385 A1 | 9/2019 | Ebbini et al. |
| 2019/0308036 A1 | 10/2019 | Ebbini |
| 2020/0121960 A1 | 4/2020 | Darrow et al. |

FOREIGN PATENT DOCUMENTS

| | | |
|---|---|---|
| CN | 102800071 A | 11/2012 |
| EP | 0392743 A1 | 10/1990 |
| EP | 2310094 B1 | 10/2014 |
| WO | WO 2006/018761 A1 | 2/2006 |
| WO | WO 2006/042201 A1 | 4/2006 |
| WO | WO 2006/090298 A1 | 8/2006 |
| WO | WO 2008/053457 A2 | 5/2008 |
| WO | WO 2009/002492 A1 | 12/2008 |
| WO | WO 2009/050719 A2 | 4/2009 |
| WO | WO 2011/156624 A2 | 12/2011 |
| WO | WO 2012/033584 A2 | 3/2012 |
| WO | WO 2012/142455 A2 | 10/2012 |
| WO | WO 2013/059833 A1 | 4/2013 |
| WO | WO 2015/013196 A2 | 1/2015 |

OTHER PUBLICATIONS

English translation of Office Action for Chinese Patent Application No. 201810722985.7, dated Nov. 24, 2020, 15 pages.

European Search Report dated Jul. 27, 2020 for European Patent Application No. 20176810.8, 8 pages.

Ainsworth, "3D ultrasound measurement of change in carotid plaque volume—A tool for rapid evaluation of new therapies," 2005. *Stroke*. 36(9):1904-1909.

Aldiabat, "Real-Time Image-Based Transcranial Refocusing of Dual-Mode Ultrasound Arrays" Dissertation, Jan. 2019, 161 pages.

Alonso, "Focal delivery of AAV2/1-transgenes into the rat brain by localized ultrasound-induced BBB opening" 2013 *Mol Ther Nucleic Acids*, 2:e73.

Amini, "Noninvasive Estimation of Tissue Temperature Via High-Resolution Spectral Analysis Techniques," Feb. 2005 *IEEE Transactions on Biomedical Engineering*, 52(2):221-228.

Arthur, "In vivo change in ultrasonic backscattered energy with temperature in motion-compensated images," 2008 *International Journal of Hyperthermia*, 24(5):389-398.

Arvanitis, "Combined ultrasound and mr imag-ing to guide focused ultrasound therapies in the brain" Jul. 2013 *Phys Med Biol*, 58(14):4749-4761.

Aryal, "Multiple treatments with liposomal doxorubicin and ultrasound-induced disruption of blood-tumor and blood-brain barriers improve outcomes in a rat glioma model" Jul. 2013 *J Control Release*, 169(1-2):103-111.

Aubry, "Experimental demonstration of noninvasive transskull adaptive focusing based on prior computed tomography scans" 2013 *The Journal of the Acoustical Society of America*, 113(1):84-93.

Aubry, "Transcostal high-intensity-focuses ultrasound: Ex vivo adaptive focusing feasibility study," 2008 *Phys. Med. Biol.*, 53:2937-2951.

(56) References Cited

OTHER PUBLICATIONS

Baek, "A review of low-intensity focused ultrasound for neuromodulation" 2017 *Biomed. Eng. Lett.* 7:135-142.
Baker, "A review of therapeutic ultrasound: biophysical effects" 2001 *Phys. Ther.* 81, 1351-1358.
Bakker, "The scalable brain atlas: Instant web-based access to public brain atlases and related content" 2015 *Neuroinformatics*, 13(3):353-366.
Ballard, "Adaptive transthoracic refocusing of dual-mode ultrasound arrays" Jan. 2010 *IEEE Trans Bionred Eng.*, 57(1): 93-102.
Ballard, "Monitoring and Guidance of HIFU Beams with Dual-Mode Ultrasound Arrays," *31st Annual International Conference of the IEEE EMBS*, Minneapolis, MN; Sep. 2-6, 2009:137-140.
Ballard, "Dual-mode ultrasound arrays for image-guided targeting of atheromatous plaques" in *AIP Conference Proceedings* 1503, 124-128 (AIP, 2012).
Barber, "The density of tissues in and about the head" 1970 *Acta neurologica scandinavica*, 46(1):85-92.
Barnard, "Small localized ultrasonic lesions in the white and gray matter of the cat brain" 1956 *AMA Archives of Neurology & Psychiatry*, 75(1): 15-35.
Bayat, "Adaptive motion compensation for in vivo ultrasound temperature estimation" in Ultrasonics Symposium (IUS), 2013 IEEE International, pp. 1797-1800.
Bayat, "Ultrasound thermography in vivo: A new model for calculation of temperature change in the presence of temperature heterogeneity" in 2013 *IEEE International Ultrasonics Symposium (IUS)*, pp. 116-119 (ieeexplore.ieee.org, 2013).
Bischof, "Rectal Protection During Prostate Cryosurgery: Design and Characterization of an Insulating Probe," 1997 *Cryobiology*, 34:80-92.
Blake, "A Method to estimate wall shear rate with a clinical ultrasound scanner" 2008 *Ultrasound in Medicine and Biology*, 34(5):760-774.
Blana, "First analysis of the long-term results with transrectal HIFU in patients with localized prostate cancer" Jun. 2008 *Euro Urology*, 53(6):1194-1203.
Bohn, "An analysis package comparing PID anti-windup strategies" Apr. 1995 *Control Systems Magazine, IEEE*, 15(2):34-40.
Botros, "A Hybrid Computational Model for Ultrasound Phased-Array Heating in Presence of Strongly Scattering Obstacles" Nov. 1997 IEEE Trans Biomed Eng., 44(11): 1039-1050.
Botros, "Two-step hybrid virtual array-ray (VAR) technique for focusing through the rib cage," Jul. 1998 *IEEE Trans. Ultrason. Ferroelectr., Freq. Control*, 45(4): 989-1000.
Bracewell, "Two-dimensional Imaging" Prentice-Hall Signal Processing Series. 1995. Cover page, Title Page, Copyright Page, and Table of Contents. 11 pages total.
Burgess, "Targeted delivery of neural stem cells to the brain using mri-guided focused ultrasound to disrupt the blood-brain barrier" 2011 *PLoS One*, 6(11):e27877.
Byrne, "Epidural cylinder electrodes for presurgical evaluation of intractable epilepsy: technical note" Aug. 2008 Surg Neurol., 70(2):160-4; discussion 164. doi: 10.1016/j.surneu.2007.04.024. Epub Feb. 8, 2008.
Bystristsky, A review of low-intensity transcranial focused ultrasound for clinical applica-tions. *Curr Behav Neurosci*, 2:60-66, 2015.
Bystritsky, A review of low-intensity focused ultrasound pulsation. *Brain Stimul*, 4(3):125-136, Jul. 2011.
Casper, "Realtime Control of Multiple-focus Phased Array Heating Patterns Based on Noninvasive Ultrasound Thermography," 2010 *IEEE International Ultrasonics Symposium Proceedings*, pp. 467-470.
Casper, "Realtime Control of Multiple-focus Phased Array Heating Patterns Based on Noninvasive Ultrasound Thermography," Jan. 2012 *IEEE Trans. Biomed. Eng.*, 59(1):95-105.
Casper, "Real-time implementation of a dual-mode ultrasound array system: In vivo results" 2013 IEEE Transactions on Biomedical Engineering, 60(10):2751-2759.

Cespedes, "Echo decorrelation from displacement gradients in elasticity and velocity estimation" 1999 *IEEE Trans. UFFC.*, 46:791-801.
Chan, "Laser-generated focused ultrasound for arbitrary waveforms" 2016 *Appl. Phys. Lett.*, 109:174102.
Chan, "An image-guided high intensity focused ultrasound device for uterine fibroids treatment," 2002 *Med. Phys.*, 29:2611-2620.
Chan, Chapter 2 "Basics of Ultrasound Imaging" Narouze (Ed.), Atlas of Ultrasound-Guided Procedures in Interventional Pain Management, Springer: New York, NY; 2011. Cover page, publisher's page, and pp. 13-19.
Chang, "Unilateral magnetic resonance guided focused ultrasound thalamotomy for essential tremor: practices and clinicoradiological outcomes" 2015 *J Neurol Neurosurg Psychiatry*, 86(3):257-264.
Chapelon, "New piezoelectric transducers for therapeutic ultrasound," Jan. 2000 *Ultrasound Med. Biol.*, 26(1):153-159.
Chew, Waves and Fields in Inhomogenous Media, Van Nostrand Reinhold: New York; 1990. Cover Page, Title Page, Copyright Page, and Table of Contents. 12 pages total.
Chiao, "Coded excitation for diagnostic ultrasound: A system developer's perspective" Feb. 2005 IEEE Trans. *Ultrason., Ferroelect., Freq. Colllr.*, 52(2):160-170.
Chu, "Neuromodulation Accompanying Focused Ultrasound-Induced Blood-Brain Barrier Opening" Oct. 2015 *Scientific Reports* 5:15477; 12 pages.
Clement, "A noninvasive method for focusing ultrasound through the human skull" 2002 *Phys Med Biol.*, 47: 1219-1236.
Coluccia, "First noninvasive thermal ablation of a brain tumor with MR-guided focused ultrasound," 2014, *J Ther Ultrasound*, 2:17.
Constans, "A 200-1380-kHz Quadrifrequency Focused Ultrasound Transducer for Neurostimulation in Rodents and Primates: Transcranial In Vitro Calibration and Numerical Study of the Influence of Skull Cavity" 2017 *IEEE Trans Ultrason Ferroelectr Freq Control.*, 64(4):717-724. doi: 10.1109/TUFFC.2017.2651648. Epub Jan. 11, 2017.
Corl, "A real-time synthetic-aperture imaging system" in Acoustical Imaging vol. 9 Visualization and Characterization, 1980, Plenum Press. Cover page, copyright page and pp. 341-355.
Curiel, "1.5-D high intensity focused ultrasound array for non-invasive prostate cancer surgery," Feb. 2002 *IEEE Trans. Ultrason., Ferroelectr., Freq. Control*, 49(2):231-242.
Dallapiazza, "Noninvasive neuromodulation and thalamic mapping with low-intensity focused ultrasound" Apr. 2017, *J Neurosurg.*, 1-10. doi: 10.3171/2016.11.JNS16976. [Epub ahead of print].
Dalong, "Viscoelastic property measurement in thin tissue constructs using ultrasound," 2008 *IEEE Trans. Ultrason. Ferroelecdt. Freq. Contr.*, 55(2):368-383.
Daniels, "Focused Ultrasound-Induced Suppression of Auditory Evoked Potentials in Vivo" 2018 *Ultrasound Med. Biol.* 44, 1022-1030.
Darrow, "Reversible neuroinhibition by focused ultrasound is mediated by a thermal mechanism" Nov.-Dec. 2019 *Brain Stimul.*, 12(6):1439-1447. doi: 10.1016/j.brs.2019.07.015. Epub Jul. 23, 2019. Prepublication.
Darrow, "Transcranial Focused Dual-Mode Ultrasound for Noninvasive Neuromodulation" presentation Sep. 30, 2018, Minnesota Neurological Society meeting; 34 pages.
Darvas, "Toward Deep Brain Monitoring with Superficial EEG Sensors Plus Neuromodulatory Focused Ultrasound" Aug. 2016, *Ultrasound Med Biol.*, 42(8):1834-47. doi: 10.1016/j.ultrasmedbio.2016.02.020. Epub May 13, 2016.
Davies, "Pulse wave analysis and pulse wave velocity: A critical review of their strengths and weaknesses" Mar. 2003 *J Hypertens.*, 21(3):463-72.
Deffieux, "Low-intensity focused ultrasound modulates monkey visuomotor behavior" 2013 *Current Biology*, 23(23):2430-2433.
Deng, "Targeted drug delivery across the blood-brain barrier using ultrasound technique" Dec. 2010 *Ther Deliv*, 1(6):819-848.
Dumas, "Piezocomposite technology an innovative approach to the improvement of ndt performance using ultrasounds" in 8th European Conference on Non Destructive Testing, Jun. 2002, Barcelona, Spain; 2 pages.

(56) References Cited

OTHER PUBLICATIONS

Dunmire, "Cross-beam vector doppler ultrasound for angle-independent velocity measurements" Oct. 2000 *Ultrasound Med Biol.*, 26(8):1213-1235.
Ebbini, "A cylindrical-section ultrasound phased-array applicator for hyperthermia cancer therapy," 1988 *IEEE Trans. Ultrasonics, Ferroelectrics, and Frequency Control*, 35(5):561-572.
Ebbini, "Deep-localized hyperthermia with ultrasound phased arrays using the pseudoinverse pattern synthesis methods," Ph.D. Dissertation, University of Illinois, Urbana, IL, 1990, 24 pages.
Ebbini, "Dereverberation of ultrasound echo data in vascular imaging applications" 2011, *ICASSP, IEEE International Conference on Acoustics, Speech and Signal Processing—Proceedings.* 2011: 741-744.
Ebbini, "Dual-mode ultrasound phased arrays for image-guided surgery" Apr. 2006 *Ultrasonic Imaging*, 28(2):65-82.
Ebbini, "Experimental evaluation of a prototype cylindrical section ultrasound hyperthermia phased-array applicator," Sep. 1991 *IEEE Transactions on Ultrasonics Ferroelectrics and Frequency Control*, 38(5):510-520.
Ebbini, "Fundamental resolution limits of a coded-excitation system for real-time pulse-echo imaging" in Nov. 1997 Proceedings of the IEEE Ultrasonic Symposium 2, 1997(2):1539-1542.
Ebbini, "Guest Editorial to the Special Issue on Therapeutic Ultrasound: Current Status and Future Directions," Jan. 2010 *IEEE Transactions on Biomedical Engineering*, 57(1):57-60.
Ebbini, "Guest Editorial to the Special Issue on Therapeutic Ultrasound: Trends at the Leading-Edge," *IEEE Transactions on Biomedical Engineering*, Jan. 2010; 57(1):5-6.
Ebbini, "Lesion formation and visualization using dual-mode ultrasound phased arrays," Oct. 2001 *Proc. IEEE Ultrason. Symp.*, 2:1351-1354.
Ebbini, "Monitoring and Guidance of Minimally-Invasive Thermal Therapy Using Diagnostic Ultrasound," $31^{st}$ Annual International Conference of the IEEE EMBS, Minneapolis, MN; Sep. 2-6, 2009:4283-4286.
Ebbini, "Multiple-focus ultrasound phased-array pattern synthesis: optimal driving-signal distributions for hyperthermia" Sep. 1989 IEEE Trans Ultrason Ferroelectr Freq Control., 36(5):540-8.
Ebbini, "A new Svd-based optimal inverse filter design for ultrasonic applications" in Ultrasonics Symposium, 1993. Proceedings., IEEE, 2:1187-1190.
Ebbini, "Optimal transversal filter bank for 3d real-Lime acoustical imaging" in Signals, Systems and Computers, 1992 Conference Record of The Twenty-Sixth Asilomar Conference 011, 2:831-835.
Ebbini, "Optimization of the intensity gain of multiple-focus phased-array heating patterns," 1991 *Int. J. Hyperthermia*, 7(6): 953-973.
Ebbini, "Phase-coupled two-dimensional speckle tracking algorithm" May 2006 IEEE Trans Ultrason Ferroelectr Freq Control., 53(5):972-90.
Ebbini, "Real-time ultrasound thermography and thermometry [life sciences]" Mar. 2018 IEEE Signal Processing Magazine, 35:166-174.
Ebbini, "Region-adaptive motion tracking of speckle imagery" 2000 ICASSP, IEEE International Conference on Acoustics, Speech and Signal Processing—Proceedings. 4:2075-2078.
Ebbini, "A spherical-section ultrasound phased array applicator for deep localized hyperthermia," Jul. 1991 *IEEE Trans. Biomedical Engineering*, 38(7):634-643.
Elias, "A randomized trial of focused ultrasound thalamotomy for essential tremor" Aug. 2016, *New England Journal of Medicine*, 375(8):730-9.
European Search Report and Search Opinion for European Patent Application No. 18193572.7, dated Sep. 2, 2019, 15 pages.
Figueroa, "A Computational Framework for Fluid-Solid-Growth Modeling in Cardiovascular Simulations" Sep. 2009 *Comput Methods Appl Mech Eng.*, 198(45-46):3583-3602.
Fink, "Time reversal of ultrasonic fields. I. Basic principles," Sep. 1992 *IEEE Trans. Ultrason., Ferroelectr., Freq. Control*, 39(5):555-566.
Fisher, "Low-intensity focused ultrasound alters the latency and spatial patterns of sensory-evoked cortical responses in vivo" 2018 *J. Neural Eng.* 15, 035004.
Fleury, "New piezocomposite transducers capable of producing high-power levels suitable for therapy with reasonably wide bandwidth suitable for imaging," 2002 *Proc. $2^{nd}$ Int. Symp. Ther. Ultrasound*, 1:428-436.
Fry, "Ultrasonic lesions in the mammalian central nervous system" 1955, *Science*, 122(3168):517-518.
Fry, "Acoustical properties of the human skull" 1978 *The Journal of the Acoustical Society of America*, 63(5):1576-1590.
Fry, "Fundamental neurological research and human neurosurgery using intense ultrasound" 1960 *IRE transactions on medical electronics*, 3:166-181.
Fry, "Further studies of the transkull transmission of an intense focused ultrasonic beam: lesion production at 500 khz" 1980 *Ultrasound Med Biol*, 6(1):33-38.
Fry, "Production of focal destructive lesions in the central nervous system with ultrasound" 1954 *Journal of neurosurgery*, 11(5):471-478.
Fry, "Production of reversible changes in the central nervous system by ultrasound" 1958 *Science*, 127(3289):83-84.
Fry, "Transkull transmission of an intense focused ultrasonic beam" 1977 *Ultrasound in Medicine and Biology*, 3(2):183-184.
Fry, "Transkull focal lesions in cat brain produced by ultrasound" May 1981 *J Neurosurg*, 54(5):659-663.
Fung, Biomechanics: Circulation, $2^{nd}$ Ed. Springer, New York. 1997. Cover Page, Copyright Page, Table of Contents.
Gelet, "845 Prostate cancer control with transrectal HIFU in 242 consecutive patients: 5-year results" Jan. 2004 *European Urology Supplements* 3(2):214-214.
Goel, "Adjuvant Approaches to Enhance Cryosurgery," Jul. 2009 *Journal of Biomechanical Engineering*, 131(7):074003.
Golemati, "Carotid artery wall motion estimated from b-mode ultrasound using region tracking and block matching" 2003 *Ultrasound in Med & Biol.*, 29(3):387-399.
Goodman, "*Introduction to Fourier Optics*" 2005, Roberts & Company, Greenwood Village, Colorado. Cover page, publisher page, table of contents.
Gronningsaeter, "Vessel wall detection and blood noise reduction in intravascular ultrasound imaging," May 1996; *IEEE Transactions on Ultrasonics, Ferroelectronics and Frequency Control, IEEE, US*, 43(3):359-369.
Gulick, "Comparison of Electrical and Ultrasound Neurostimulation in Rat Motor Cortex" 2017 *Ultrasound Med. Biol.*, 43:2824-2833.
Gulick, "Effect of Ultrasound Stimulation on Excised Brain Tissue Impedence" 2013 *IEEE Neural Engineering Short Papers No. 0669*; 1 page.
Guo, "Ultrasound Produces Extensive Brain Activation via a Cochlear Pathway" 2018 *Neuron* 98:1020-1030.e4.
Haddadin, "Imaging Strongly Scattering Media Using Multiple-frequency Distorted Born Iterative Method," 1998 *IEEE Trans. UFFC*, 5(6):1485-1496.
Haddadin, "Ultrasonic focusing through inhomogeneous media by application of the inverse scattering problem" Jul. 1998, *J Acoust Soc Am.*, 104(1): 313-325.
Haken, "Effect of mode conversion on ultrasonic heating oat tissue interfaces," 1992 *J. Ultrasound Med.*, 11:393-405.
Hakimova, "Ultrasound stimulation inhibits recurrent seizures and improves behavioral outcome in an experimental model of mesial temporal lobe epilepsy" Aug. 2015 *Epilepsy Behav*, 49:26-32.
Hall, "Phantom materials for elastography" 1997 *IEEE transactions on ultrasonics, ferroelectrics, and frequency control*, 44(6):1355-1365.
Hameroff, "Transcranial ultrasound (TUS) effects on mental states: a pilot study" May 2013 *Brain Stimul.*, 6(3):409-15. doi: 10.1016/j.brs.2012.05.002. Epub May 29, 2012.
Haritonova, "In vivo application and localization of transcranial focused ultrasound using dual-mode ultrasound arrays" 2015 *IEEE transactions on ultrasonics, ferroelectrics, and frequency control*, 62(12):2031-2042.

(56) References Cited

OTHER PUBLICATIONS

Hermus, "Advanced carotid plaque imaging" 2010 *European Journ. Of Vascular and Endovascular Surgery*, 39(2):125-133.

Hindley, "MRI guidance of focused ultrasound therapy of uterine fibroids: Early results," Dec. 2004 *Am. J. Roentgenology*, 183(6):1713-1719.

Hirata, "Pulse wave analysis and pulse wave velocity: a review of blood pressure interpretation 100 years after Korotkov" Oct. 2006 *Circ J.*, 70(10):1231-9.

Hynynen, "Demonstration of potential noninvasive ultrasound brain therapy through an intact skull" 1998 *Ultrasound in medicine & biology*, 24(2):275-283.

Hynynen, "MR imaging-guided focused ultrasound surgery of fibroadenomas in the breast: a feasibility study" 2001 *Radiology*, 219(1):176-185.

Hynynen, "Noninvasive MR imaging-guided focal opening of the blood-brain barrier in rabbits" Sep. 2001 *Radiology*, 220(3):640-646.

Hynynen, "Pre-clinical testing of a phased array ultrasound system for mri-guided noninvasive surgery of the braina primate study" 2006 *European journal of radiology*, 59(2):149-156.

Hynynen, "Trans-skull ultrasound therapy: The feasibility of using image-derived skull thickness information to correct the phase distortion," May 1999 *IEEE Trans. Ultrason, Ferroelectr., Freq. Control*, 46(5):752-755.

Hynynen, "Ultrasound for drug and gene delivery to the brain" Jun. 2008 *Adv Drug Deliv Rev*, 60(10):1209-1217.

Hynynen, "500-element ultrasound phased array system for noninvasive focal surgery of the brain: a preliminary rabbit study with ex vivo human skulls" 2004 *Magn. Reson. Med.*, 52:100-107.

Hyungmin, "Estimation of the spatial profile of neuromodulation and the temporal latency in motor responses induced by focused ultrasound brain stimulation" May 2014 *Neuroreport*, 25(7):475-479.

Ibbini, "N X N square-element ultrasound phased array applicator: Simulated temperature distributions associated with directly synthesized heating patterns," 1990 *IEEE Trans. Ultrason, Ferroelectr., Freq. Control*, 37(6):491-500.

Insana, "Maximum-likelihood approach to strain imaging using ultrasound" 2000 *J. Acoust. Soc. Am.*, 107(3):1421-1434.

International Written Opinion/International Preliminary Report on Patentability, dated Jul. 15, 2009 for International Patent Application No. PCT/US2008/007842, 25 pgs.

International Preliminary Report on Patentability dated Feb. 4, 2016 for International Patent Application No. PCT/US2014/047430, 13 pages.

International Preliminary Report on Patentability dated Oct. 15, 2013 for International Patent Application No. PCT/US2012/033584, 12 pgs.

International Preliminary Report on Patentability dated Dec. 10, 2012 for International Patent Application No. PCT/US2011/039837, 6 pgs.

International Search Report dated Jun. 13, 2013 for International Patent Application No. PCT/US2012/033584, 6 pgs.

International Search Report dated Jan. 20, 2012 for International Patent Application No. PCT/US2011/039837, 4 pgs.

International Search Report dated Jan. 20, 2015 for International Patent Application No. PCT/US2014/047430, 16 pgs.

Ishida, "Development and animal experiment of variable focusing HIFU system for prostate cancer treatment," 2003 $3^{rd}$*Int. Symp. THer. Ultrasound*, 1:382-387.

Jedrzejewicz, "Two-way continuous transmit and receive focusing in ultrasound imaging" 2013 ZONARE Medical Systems, Inc., Tech. Rep., [Online]. Available: http://res.mindray.com/Documents/2016-12-14/d2dd8ebd-a052-482a-8541-b8de227d4ee6/K90127_two_way_transmit_receive.pdf.

Jensen, "Calculation of pressure fields from arbitrarily shaped, apodized, and excited ultrasound transducers" 1992 *IEEE transactions on ultrasonics, ferroelectrics, and frequency control*, 39(2):262-267.

Jensen, "Synthetic aperture ultrasound imaging" 2006 *Ultrasonics*, 44:e5-e15.

Jones, "Comparison of analytical and numerical approaches for ct-based aberration correction in transcranial passive acoustic imaging" 2015 *Physics in Medicine & Biology*, 61(1): 23.

Jossinet, "Impedance Modulation by Pulsed Ultrasound" 1999 *Annals of the New York Academy of Sciences* 873 (I Electrical BI):396-407.

Kamimura, "Focused ultrasound neuromodulation of cortical and subcortical brain structures using 1.9 MHz" 2016 *Med. Phys.* 43, 5730.

Karimi, "Estimation of Nonlinear Mechanical Propcnics of Vascular Tissues via Elastography" Dec. 2008 *Cardiovasc Eng.*, 8(4):191-202. doi: 10.1007/s10558-008-9061-0.

Khanna, "Intracranial Applications of MR Imaging-Guided Focused Ultrasound" 2017 *AJNR Am. J. Neuroradiol.* doi:10.3174/ajnr.A4902, 426-431.

Khraiche, "Ultrasound induced increase in excitability of single neurons" 2008 *Conf Proc IEEE Eng Med Biol Soc.* 2008:4246-9. doi: 10.1109/IEMBS.2008.4650147.

Kim, "Arterial vulnerable plaque characterization using ultrasound-induced thermal strain imaging (TSI)," 2008 *IEEE Transaction on Biomedical engineering*, 55(1):171-180.

Kim, "Estimation of the spatial profile of neuromodulation and the temporal latency in motor responses induced by focused ultrasound brain stimulation" 2014 *Neuroreport*, 25(7):475.

Kim "Focused ultrasound-mediated non-invasive brain stimulation: examination of sonication parameters" 2014 *Brain Stimul.*, 7(5):748-56. doi: 10.1016/j.brs.2014.06.011. Epub Jul. 2, 2014.

Kim, "Noninvasive transcranial stimulation of rat abducens nerve by focused ultrasound" *Ultrasound in medicine & biology*, 38, No. 9, pp. 1568-1575, 2012.

Kim, "Suppression of EEG visual-evoked potentials in rats through neuromodulatory focused ultrasound" 2015 *Neuroreport* 26:211-215.

King, "Effective parameters for ultrasound-induced in vivo neurostimulation" *Ultrasound in medicine & biology*, 39, No. 2, pp. 312-331, 2013.

King, "Localization of ultrasound induced in vivo neurostimulation in the mouse model" *Ultrasound in medicine & biology*, 40, No. 7, pp. 1512-1522, 2014.

Kinoshita, "Noninvasive localized delivery of herceptin to the mouse brain by mri-guided focused ultrasound-induced blood-brain barrier disruption" *Proceedings of the National Academy of Sciences*, 2006, 103(31):11719-11723.

Konofagou, "Optimization of the ultrasound-induced blood-brain barrier opening" 2012 *Theranostics*, 2(12):1223-1237.

Krishna, "Prospective Tractography-Based Targeting for Improved Safety of Focused Ultrasound Thalamotomy" 2018 *Neurosurgery.* doi:10.1093/neuros/nyy020.

Kyriakou, "A review of numerical and experimental compensation techniques for skull-induced phase aberrations in transcranial focused ultrasound" 2014 *Int. J. Hyperthermia* 30:36-46.

Lalonde, "Field conjugate acoustic lenses for ultrasound hyperthermia" Sep. 1993 *IEEE Transactions on Ultrasonics, Ferroelectrics, and Frequency Control*, 40(5):592-602.

Lalonde, "Variable frequency field conjugate lenses for ultrasound hyperthermia" Sep. 1995 *IEEE Transactions on Ultrasonics, Ferroelectrics, and Frequency Control*, 42(5):825-831.

Lee, "High Intensity Focused Ultrasound Effect on Cardiac Tissues: Potential for Clinical Application," 2000 *Echocardiography*, 17(6):563-566.

Legon, "Neuromodulation with single-element transcranial focused ultrasound in human thalamus" 2018 *Hum. Brain Mapp.* 39, 1995-2006.

Legon, "Transcranial focused ultrasound modulates the activity of primary somatosensory cortex in humans" 2014 *Nature Neurosci.*, 17(2):322-329.

Legon, "Transcranial focused ultrasound neuromodulation of the human primary motor cortex" 2018 *Sci. Rep.* 8:10007.

Lele, "The thermal hypothesis of the mechanism of ultrasonic focal destruction in organized tissues" Interaction of ultrasound and biological tissues. FDA, pp. 73-8008, 1972.

(56) References Cited

OTHER PUBLICATIONS

Li, "A new filter design technique for coded excitation systems," 1992 *IEEE Trans. Ultrasonics, Ferroelectrics, and Frequency Control*, 39(6):693-699.

Li, "Blocked Element Compensations in Phased Array Imaging," 1993 *IEEE Trans. Ultrasonics, Ferroelectrics, and Frequency Control*, 40(4):283-292.

Lindsey, "Simultaneous bilateral real-time 3-d transcranial ultrasound imaging at 1 {MHz} through poor acoustic windows" 2013 *Ultrasound in Medicine and Biology*, 39(4) 721-734, 2013.

Lipsman, "MR-guided focused ultrasound thalamotomy for essential tremor: a proof-of-concept study" 2013 *The Lancet Neurology*, 12(5):462-468.

Liu, "Adaptive lesion formation using dual mode ultrasound array system" 2017 *AIP Conf. Proc.* 1821, 060003.

Liu, "In vivo mr quantification of superparamagnetic iron oxide nanoparticle leakage during low-frequency-ultrasound-induced blood-brain barrier opening in swine" Dec. 2011 *J Magn Reson Imaging*, 34(6):1313-1324.

Liu, "Magnetic resonance monitoring of focused ultrasound/magnetic nanoparticle targeting delivery of therapeutic agents to the brain" Aug. 2010 *Proc Natl Acad Sci U S A*, 107(34):15205-15210.

Liu, "Real-Time 2-D Temperature Imaging Using Ultrasound" Jan. 2010 *IEEE Trans Biomed Eng.*, 57(1):12-6.

Liu, "Three-dimensional image guidance for transcranial focused ultrasound therapy" Apr. 2017 IEEE 14th International Symposium on Biomedical Imaging (ISBI 2017), 916-919.

Liu, "Viscoelastic property measurement in thin tissue constructs using ultrasound" 2008 *IEEE Trans. Ultrason. Ferroelect. Freq. Contr.* 55(2):368-383.

Lockwood, "High-speed method for computing the exact solution for the pressure variations in the near field of a baffled piston" *The Journal of the Acoustical Society of America*, 53, No. 3, pp. 735-741:1973.

Lubinski, "Speckle tracking methods for ultrasonic elasticity imaging using short-time correlation" 1999 *IEEE Trans. UFFC.*, 46:82-96.

Luo, "Pulse wave imaging of normal and aneurysmal abdominal aortas in vivo" Apr. 2009 *IEEE Trans Med Imaging.*, 28(4):477-86.

Lynn, "Histology of cerebral lesions produced by focused ultrasound" 1944 *The American journal of pathology*, 20(3):637.

Maass-Moreno, "Noninvasive temperature estimation in tissue via ultrasound echo shifts. Part I. Theoretical model," 1996 *The Journal of the Acoustical Society of America*, 100(4.1):2514-2521.

Mahmoud, "In vivo vascular wall tissue characterization using a strain tensor measuring (STM) technique for flow-mediated vasodilation analyses" 2009 *Physics in Medicine and Biology*, 54(20):6217-6238.

Maimbourg, "3d printed adaptive acoustic lens as a disruptive technology for transcranial ultrasound therapy using single-element transducers" 2018 *Physics in Medicine & Biology*, 63(2):025026.

Manlapaz, "Effects of ultrasonic radiation in experimental focal epilepsy in the cat" 1964 *Experimental neurology*, 10(4):345-356.

Marquet, "Non-invasive transcranial ultrasound therapy based on a 3d ct scan: protocol validation and in vitro results" May 2009 *Phys Med Biol*, 54(9):2597-2613.

Martin, "High intensity focused ultrasound for noninvasive functional neurosurgery" 2009 *Annals of Neurology: Official Journal of the American Neurological Association and the Child Neurology Society*, 66(6):858-861.

Martin, "Investigation of HIFU produced emulsion for acoustic hemostasis," 2003 *Proc. 3rd Int. Symp. Ther. Ultrasound*, 1:351-356.

Marty, "Dynamic study of blood-brain barrier closure after its disruption using ultrasound: a quantitative analysis" Oct. 2012 *J Cereb Blood Flow Metab*, 32(10):1948-1958.

McDannold, "Transcranial magnetic resonance imaging-guided focused ultrasound surgery of brain tumors: initial findings in 3 patients" *Neurosurgery*, 66, No. 2, 323-332, 2010.

McGough, "Direct Computation of ultrasound phased-array driving signals from specified temperature distribution for hyperthermia," Aug. 1992 *IEEE Trans. Biomedical Engineering*, 39(8):825-835.

McGough, "Mode scanning: heating pattern synthesis with ultrasound phased arrays," 1994 *Int. Journal of Hyperthermia*, 10(3):433-442.

McGough, "Rapid calculations of time-harmonic nearfield pressures produced by rectangular prisons" *The Journal of the Acoustical Society of America*, 115, No. 5, pp. 1934-1941, 2004.

Mehic, "Increased anatomical specificity of neuromodulation via modulated focused ultrasound" 2014 *PLoS One*, 9(2):e86939.

Meyers, "Early experiences with ultrasonic irradiation of the pallidofugal and nigral complexes in hyperkinetic and hypertonic disorders" Jan. 1959 *J Neurosurg*, 16(1):32-54.

Miller, "Fundamental limitations of noninvasive temperature imaging by means of ultrasound echo strain estimation," 2002 *Ultrasound in Medicine and Biology*, 28(10):1319-1333.

Min, "Focused ultrasound-mediated suppression of chemically-induced acute epileptic EEG activity" 2011 *BMC Neurosci.*, 12:23.

Misaridis, "Use of modulated excitation signals in medical ultrasound. part 1: basic concepts and expected benefits" Feb. 2005 *IEEE Trans. Ultrason., Ferroelect., Freq. Colltr.*, 52(2): 177-191.

Montaldo, "Spatio-temporal coding in complex media for optimum beamforming: the iterative time-reversal approach" Feb. 2005 *IEEE Trans. Ultrason., Ferroelect., Freq. Comr.*, 52(2):220-230.

Mougenot, "Automatic spatial and temporal temperature control for MR-guided focused ultrasound using fast 3D MR thermometry and multispiral trajectory of the focal point," Nov. 2004 *Magnetic Resonance in Medicine*, 52(5):1005-1015.

Mougenot, "Three-dimensional spatial and temporal temperature control with MR thermometry-guided focused ultrasound (mrghifu)," 2009 *Magnetic Resonance in Medicine*, 61:603-614.

Moyle, "Inlet conditions for image-based CFD models of the Carotid bifurcation: Is it reasonable to assume fully developed flow?" 2006 *Journ. Of Biomechnical Engr. Transactions of the ASME*, 128(3):371-379.

Mucci, "A comparison of efficient beamforming algorithms" 1984 *IEEE Transactions on Acoustics, Speech, and Signal Processing*, 32(3):548-558.

Mueller, "Transcranial Focused Ultrasound Modulates Intrinsic and Evoked EEG Dynamics" 2014 *Brain Stimul.*, 7:900-908.

Naor, "Ultrasonic neuromodulation" 2016 *J. Neural Eng.*, 13:031003.

Nichols, *McDonald's Blood Flow in Arteries*, Hodder Arnold: New York, NY; 2005. Cover page, title page and table of contents.

Nightingale, "On the feasibility of remote palpation using acoustic radiation force," Jul. 2001 *J. Acoust. Soc. Amer.*, 110:625-634.

Ocheltree, "Sound field calculation for rectangular sources" 1989 *IEEE transactions on ultrasonics, ferroelectrics, and frequency control*, 36(2):242-248.

O'Donnell, "Coded excitation for synthetic aperture ultrasound imaging" Feb. 2005 *IEEE Trns. Ultrason., Ferroelect., Freq. Contr.*, 52(2):171-176.

Oppenheim et al., Discrete-time signal processing, Second Edition. Prentice-Hall, Upper Saddle River, New Jersey, 1999; 896 pages.

Patel, "Hard real-time closed-loop electrophysiology with the Real-Time eXperiment Interface (RTXI)" 2017 *PLoS Comput. Biol.*, 13:e1005430.

Paxinos, "The mouse brain in sterotaxic coordinates" 2004 Gulf Professional Publishing. Cover page, publisher page, table of contents.

Pernot, "High power density prototype for high precision transcranial therapy," 2003 *Proc. 3rd Int. Symp. Ther. Ultrasound*, 1:405-410.

Pernot, "Temperature estimation using ultrasonic spatial compounding," 2004 *IEEE Trans. Ultrason., Ferroelect., Freq. Contr.*, 51(5):606-615.

Pesavento, "A time efficient and accurate strain estimation concept for ultrasonic elastography using iterative phase zero estimation" 1999 *IEEE Trans, UFFC*, 46(5):1057-1067.

Pinton, "Direct phase projection and transcranial focusing of ultrasound for brain therapy" 2012 *IEEE Trans Ultrason Ferroelectr Freq Control*, 59(6):1149-59.

Podgorski, "Brain heating induced by near-infrared lasers during multiphoton microscopy" 2016 *J. Neurophysiol.* 116:1012-1023.

(56) References Cited

OTHER PUBLICATIONS

Poissonnier, "Control of prostate cancer by transrectal HIFU in 227 patients," 2007 *Eur. Urol.*, 51:381-387.
Prada, "Decomposition of the time reversal operator: Detection and selective focusing on two scatterers" 1996 *The Journal of the Acoustical Society of America*, 99(4):2067-2076.
Prada, "The iterative time reversal process: Analysis of the convergence," 1995 *J. Acoust. Soc. Amer.*, 95:62-71.
Pramanik, "Thermoacoustic and photoacoustic sensing of temperature," Sep. 2009 *Journal of Biomedical Optics*, 14(5): 054024.
Rabben, "An ultrasound-based method for determining pulse wave velocity in superficial arteries" 2004 *Jour. of Biomechanics*, 37(10):1615-1622.
Rabben, "Ultrasound-based vessel wall tracking: An auto-correlation technique with RF center frequency estimation" 2002 *Ultrasound in Medicine and Biology*, 28(4):507-517.
Raghupathy, "Generalized Anisotropic Inverse Mechanics for Soft Tissues" Aug. 2010 *J. Biomech. Eng.*, 132(8):081006.
Raymond, "Ultrasound enhanced delivery of molecular imaging and therapeutic agents in Alzheimer's disease mouse models" 2008 *PLoS One*, 3(5):e2175.
Revell et al., "Ultrasound Speckle Tracking for Strain Estimation," 2003 University of Bristol Department of Computer Science; Dec. 2003, 5 pgs.
Rezayat, "A Review on Brain Stimulation Using Low Intensity Focused Ultrasound" 2016 *Basic and Clinical Neuroscience*, 7 (3):187-94.
Ribbers, "Noninvasive two-dimensional strain imaging of arteries: Validation in phantoms and preliminary experience in carotid arteries in vivo" 2007 *Ultrasound in Medicine and Biology*, 33(4):530-540.
Rieke, "MR thermometry" 2008 *Journal of Magnetic Resonance Imaging: An Official Journal of the International Society for Magnetic Resonance in Medicine*, 27(2):376-390.
Rihaczek, "Radar waveform selection—a simplified approach" Nov. 1971 *IEEE Trans. Aerosp. Electron. Syst.*, AES-7(6):1078-1086.
Rohani, "Focused ultrasound for essential tremor: review of the evidence and discussion of current hurdles" *Tremor and Other Hyper-kinetic Movements*, 2017; 7. doi: 10.7916/D8Z89JN1.
Sakatani, "Somatosensory evoked potentials in rat cerebral cortex before and after middle cerebral artery occlusion" 1990 *Stroke* 21:124-132.
Salomir, "Hyperthermia by MR-guided focuses ultrasound: Accurate temperature control based on fast MRI and a physical model of local energy depositon and heat conduction," 2000 *Magnetic Resonance in Medicine*,43:342-347.
Salomir, "Image-based control of the magnetic resonance imaging guided focused ultrasound thermotherapy" 2006 *Topics in Magnetic Resonance Imaging*, 17(3):139-151.
Sanghvi, "Noninvasive surgery of prostate tissue by high-intensity focused ultrasound," Nov. 1996 *IEEE Trans. Ultrason., Ferroelectr., Freq. Contr.*, 43(6):1099-1110.
Sanghvi, "New developments in therapeutic ultrasound," Nov./Dec. 1996 *IEEE Eng. Med. Biol. Mag.*, 15(6):83-92.
Sapareto, "Thermal dose determination in cancer therapy," 1984 *Int. J. Rad. Onc. Biol. Phys.*, 10(6):787-800.
Sato, "Ultrasonic Neuromodulation Causes Widespread Cortical Activation via an Indirect Auditory Mechanism" 2018 *Neuron* 98:1031-1041.e5.
Savitzky, "Smoothing and diferentiation of data by simplified least squares procedures." *Analytical chemistry*, 36, No. 8, pp. 1627-1639, 1964.
Sawyer, "Nanoparticle-based evaluation of blood-brain barrier leakage during the foreign body response" *Journal of Neural Engineering*, 10(2013) 016013; 10 pages.
Schiefer, "Moving forward: Advances in the treatment of movement disorders with deep brain stimulation" 2011 *Frontiers in Integrative Neuroscience*, 5:69.
Schoenhagen, "Coronary imaging: Angiography shows the stenosis, but IVUS, CT, and MRI show the plaque" 2003 *Cleveland Clinic Journ. of Medicine*, 70(8):713-719.
Seip, "Characterization of a Needle Hydrophone Array for Acoustic Feedback during Ultrasound Hyperthermia Treatments," 1992 *Ultrasonics Symposium Proceedings*, 2:1265-1269.
Seip, "Dynamic focusing in ultrasound hyperthermia treatments using implantable hydrophone arrays," Sep. 1994 *IEEE Trans. Ultrason., Ferroelectr., Freq. Control*, 41(5):706-713.
Seip, "High-intensity focused ultrasound (HIFU) phased arrays: Recent developments in transrectal transducers and driving electronics," 2003 *Proc. 3rd Int. Symp. Ther. Ultrasound*, 1:423-428.
Seip, "Invasive and Non-Invasive Feedback for Ultrasound Phased Array Thermotherapy," 1994 *Ultrasonics Symposium Proceedings*, 3:1821-1824.
Seip, "Non-Invasive Detection of Thermal Effects due to Highly Focused Ultrasonic Fields," 1993 *Ultrasonics Symposium Proceedings*, 2:1229-1232.
Seip, "Non-invasive estimation of tissue temperature response to heating fields using diagnostic ultrasound," 1995 *IEEE Trans. Biomed. Eng.*, 42(8):828-839.
Seip, "Noninvasive real-time multipoint temperature control for ultrasound phased array treatments," Nov. 1996 *IEEE Transactions on Ultrasonics Ferroelectrics and Frequency Control*, 43(6):1063-1073.
Seip, "Non-invasive Spatio-temporal Temperature Change Estimation Using Diagnostic Ultrasound," *Ultrasonics Symposium Proceedings*, 1995, pp. 1613-1616.
Shapoori, "An ultrasonic-adaptive beamforming method and its application for trans-skull imaging of certain types of head injuries; part i: Transmission mode" *IEEE Transactions on Biomedical Engineering*, 2015, 62(5):1253-1264.
Shehata, "Feasibility of targeting atherosclerotic plaques by high-intensity-focused ultrasound: an in vivo study" Dec. 2013 *J Vasc Interv Radiol*, 24(12):1880-1887.e2.
Shen, "A New Coded-Excitation Ultrasound Imaging System-Part I: basic principles" 1996 *IEEE Trans. Ultrason., Ferroelect., Freq. Cont*, 43(1):131-140.
Shen, "A New Coded-Excitation Ultrasound Imaging System-Part II: Operator Design," 1996 *IEEE Trans. Ultrason., Ferroelect., Freq. Cont*, 43(1):141-148.
Shen, "An optimal image operator design technique for coded excitation ultrasound imaging system" *Ultrasonics Symposium Proceedings. IEEE*, 1994, 3:1777-1781.
Shen, "A Post-Beamforming Processing Technique for Enhancing Conventional Pulse-Echo Ultrasound Imaging Contrast Resolution," 1995 *IEEE Ultrasonics Symposium Proceedings*, pp. 1319-1322.
Shen, "On the design of a transversal filler bank for parallel processing multiple image lines in real-time acoustic imaging" in Acoustics, Speech, and Signal Processing, 1996. ICASSP-96. Conference Proceedings., IEEE International Conference, 6:3109-3112.
Shen, "Real-time 3d pulse-echo ultrasonic imaging with coded-excitation systems" in Image Processing, Oct. 1996. Proceedings. International Conference, 1:717-720.
Shen, "Filter-based coded-excitation system for high-speed ultrasonic imaging" Dec. 1998 *IEEE Transactions on Medical Imaging*, 17(6): 923-934.
Shung, "Scattering of ultrasound by blood" Nov. 1976 IEEE Trans Biomed Eng., 23(6):460-7.
Simon, "Combined ultrasound image guidance and therapy using a therapeutic phased array," May 1998 *SPIE Med. Imag.*, 3341:89-98.
Simon, "Estimation of Mean Scatterer Spacing Based on Autoregressive Spectral Analysis of Prefiltered Echo Data," 1995 *Ultrasonics Symposium Proceedings*, pp. 1153-1156.
Simon, "Two-Dimensional Temperature Estimation Using Diagnostic Ultrasound" Jul. 1998 *IEEE Transactions on Ultrasonics, Ferroelectrics, and Frequency Control.*, 45(4):1088-1099.
Smith, "Control system for an MRI compatible intracavitary ultrasound array for thermal treatment of prostate disease," May-Jun. 2001 *International Journal of Hyperthermia*, 17(3):271-282.

(56) References Cited

OTHER PUBLICATIONS

Souchon, "Monitoring the formation of thermal lesions with heat-induces echo-strain imaging: a feasibility study," 2005 *Ultrasound in Medicine and Biology*, 31:251-259.
Souchon, "Ultrasonic elastography using sector scan imaging and a radial compression" 2002 *Ultrasonics*, 40(1-8):867-871.
Steidl, "Dual-mode ultrasound phased arrays for noninvasive surgery: Post-beamforming image compounding algorithms for enhanced visualization of thermal lesions," Jul. 2002 *Proc. IEEE Int. Symp. Biomed. Imag.*, 429-432.
Steinman, "Flow imaging and computing: large artery hemodynamics" Dec. 2005 *Annals of Biomedical Engineering*, 33(12):1704-1709.
Sumi, "Fine elasticity imaging utilizing the iterative rf-echo phase matching method" 1999 *IEEE Transactions on Ultrasonics, Ferroelectrics, and Frequency Control*, 46(1):158-166.
Sun, "Adaptive real-time closed-loop temperature control for ultrasound hyperthermia using magnetic resonance thermometry," Oct. 2005 *Concepts in Magnetic Resonance Part B—Magnetic Resonance Engineering*, 27B(1):51-63.
Sun, "Focusing of therapeutic ultrasound through a human skull: A numerical study," 1998 *J. Acoust. Soc. Amer.*, 104:1705-1715.
Swillens, "Two dimensional flow imaging in the carotid bifurcation using a combined speckle tracking and phase-shift estimator: a study based on ultrasound simulations and in vivo analysis" 2010 *Ultrasound in Medicine and Biology*, 36(10):1722-1735.
Swillens, "Two-dimensional blood velocity estimation with ultrasound: speckle tracking versus crossed-beam vector Doppler based on flow simulations in a carotid bifurcation model" 2010 *IEEE Transactions on Ultrasonics Ferroelectrics and Frequency Control*, 57(2):327-339.
Szabo, "Diagnostic ultrasound imaging: inside out," Elsevier Academic Press, Burlington, Massachusetts, 2004. Title page, copyright page, and table of contents, 12 pages total.
Tanaka, "Active circulators—the realization of circulators using transistors" 1965 *Proceedings of the IEEE*, 53:260-267.
Tanter, "Focusing and steering through absorbing and aberrating layers: Application to ultrasonic propagation through the skull," 1998 *J. Acoust. Soc. Amer.*, 103:2403-2410.
Taylor, "Open problems in computational vascular biomechanics: Memodynamics and arterial wall mechanics" Sep. 2009 *Comput Methods Appl Mech Eng.*, 198(45-46): 3514-3523.
Tempany, "MR imaging-guided focuses ultrasound surgery of uterine leiomyomas: A feasibility study," Nov. 2003 *Radiology*, 226:897-905.
Ter Haar, "Therapeutic applications of ultrasound" 2007 *Prog. Biophys. Mol. Biol.*, 93:111-129.
Thomenius, "Evolution of ultrasound beamformers" 1996 *IEEE Ultrasonic Symposium Proceedings*, Nov. 1996, pp. 1615-1622.
Thomenius, "Recent Trends in Ultrasound Beamformation" Sep. 2005 IEEE Ultrasonics Symposium, Rotterdam, The Netherlands, 113 pages.
Trahey, "Angle independent ultrasonic blood flow detection by frame-to-frame correlation of B-mode images," *Ultrasonics*, Sep. 1988; 26(5):271-276.
Treat, "Improved anti-tumor effect of liposomal doxorubicin after targeted blood-brain barrier disruption by MRI-guided focused ultrasound in rat glioma" Oct. 2012 *Ultrasound Med Biol*, 38(10):1716-1725.
Treat, "Targeted delivery of doxorubicin to the rat brain at therapeutic levels using mri-guided focused ultrasound" Aug. 2007 *Int J Cancer*, 121(4):901-907.
Tsou, "Role of ultrasonic shear rate estimation errors in assessing inflammatory response and vascular risk" Jun. 2008 *Ultrasound Med Biol.*, 34(6): 963-972.
Tufail, "Transcranial pulsed ultrasound stimulates intact brain circuits" 2010 *Neuron* 66:681-694.
Tufail, "Ultrasonic neuromodulation by brain stimulation with transcranial ultrasound" Sep. 2011 *Nat Protoc*, 6(9):1453-1470.

Tung, "The mechanism of interaction between focused ultrasound and microbubbles in blood-brain barrier opening in mice" Nov. 2011 *J Acoust Soc Am*, 130(5):3059-3067.
Tutwiler, "Ultrasonic beamforming architectures" in Medical Imaging 1998: Ultrasonic Transducer Engineering, 3341, pp. 43-55, *International Society for Optics and Photonics*, 1998.
Tyler, "Noninvasive neuromodulation with ultrasound? A continuum mechanics hypothesis" Feb. 2011 *Neuroscientist*, 17(1):25-36.
Tyler, "Remote excitation of neuronal circuits using low-intensity, low frequency ultrasound" Oct. 2008 *PLoS One*, 3(10):e3511. doi: 10.1371/journal.pone.0003511. Epub Oct. 29, 2008.
Uchida, "Transrectal high-intensity focused ultrasound for the treatment of localized prostate cancer: Eight-year experience," Nov. 2009 *Int. J. Urology*, 16(11):881-886.
Vanbaren, "2D Large Aperture Ultrasound Phased Arrays for Hyperthermia Cancer Therapy: Design, Fabrication, and Experimental Results," 1995 *Ultrasonics Symposium Proceedings*, pp. 1269-1272.
Vanbaren, "A new algorithm for dynamic focusing of phased-array hyperthermia applicators through tissue inhomogeneities," *IEEE Ultrasonics Symposium Proceedings*, 1993; 2:1221-1224.
Vanbaren, "Multi-Point Temperature Control During Hyperthermia Treatments: Theory and Simulation," Aug. 1995 *IEEE Transactions on Biomedical Engineering*, 41(5):706-713.
Vanbaren, "Real-time Dynamic Focusing through Tissue Inhomogeneities during Hyperthermia Treatments with Phased Arrays," 1994 *Ultrasonics Symposium Proceedings*, 3:1815-1819.
Vanne, "MRI feedback temperature control for focused ultrasound surgery," 2003 *Physics in Medicine and Biology*, 48(1):31.
Varghese, "Direct strain estimation in elastography using spectral cross-correlation" 2000 *Ultrasound in Med. Biol.*, 26(9):1525-1537.
Vyas, "Extension of the angular spectrum method to calculate pressure from a spherically curved acoustic source" Nov. 2011 *J Acoust Soc Am.*, 130:2687-93.
Wagner, "Fundamental correlation lengths of coherent speckle in medical ultrasonic images" Jan. 1988 IEEE *Tmns. Ultrason., Ferroelect., Freq. Contr.*, 35(1):34-44.
Wan, "A 2d post-beamforming filter for contrast restoration in medical ultrasound: in vivo results" 2009 *Conf. Proc IEEE Eng Med Biol Soc*, 2009:1945-8.
Wan, "A Post-Beamforming 2-D Pseudoinverse Filter for Coarsely Sampled Ultrasound Arrays" Sep. 2009 *IEEE Trans Ultrason Ferroelectr Freq Control.*, 56(9):1888-1902.
Wan, "Imaging with concave large-aperture therapeutic ultrasound arrays using conventional synthetic-aperture beamforming" Aug. 2008 *IEEE Trans Ultrason Ferroelectr Freq Control*, 55(8):1705-18.
Wan, "Imaging vascular mechanics using ultrasound: Phantom and in vivo results" Apr. 14-17, 2010, 7th IEEE International Symposium on Biomedical Imaging: From Nano to Macro, ISBI 2010, Rotterdam; Netherlands, Article No. 5490152, 980-983.
Wan, "Simultaneous imaging of tissue motion and flow velocity using 2D phase-coupled speckle tracking" 2010 *Proceedings—IEEE Ultrasonics Symposium*, 2010: 487-490.
Wan, "Ultrasound surgery: Comparison of strategies using phased array systems," Nov. 1996 *IEEE Trans. UFFC*, 43(6):1085-1098.
Wang, "Adaptive 2-D Cylindrical Section Phased Array System for Ultrasonic Hyperthermia," 1992 *Ultrasonics Symposium Proceedings*, 2:1261-1264.
Wang, "Effects of phase quantization errors on field patterns generated by an ultrasound phased array hyperthermia applicator," 1991 *IEEE Trans. Ultrasonics Ferroelec. Frequency Control*, 38(5): 521-531.
Wang, "Phase aberration correction and motion compensation for ultrasonic hyperthermia phased arrays: Experimental results" 1994 *IEEE Trans. on Ultrason., Ferroelec., and Freq. Control*, 41(1):34-43.
Weintraub, "The emerging role of transcranial magnetic resonance imaging-guided focused ultrasound in functional neurosurgery" 2016 *Movement Disorders*, 32(1):20-27.

(56) References Cited

OTHER PUBLICATIONS

Weitzel, "High-Resolution Ultrasound Elasticity Imaging to Evaluate Dialysis Fistula Stenosis" Jan. 2009 *Seminars in Dialysis*, 22(1):84-89.
White, "Effect of the skull in degrading the display of echoencephalographic b and c scans" *The Journal of the Acoustical Society of America*, 44, No. 5, pp. 1339-1345, 1968.
White, "The deformation of the ultrasonic field in passage across the living and cadaver head" *Medical and biological engineering*, 7, No. 6, pp. 607-618, 1969.
White, "Transcranial ultrasound focus reconstruction with phase and amplitude correction" 2005 *IEEE Trans. Ultrason. Ferroelectr. Freq. Control*, 52:1518-1522.
Wright, "Ultrasonic stimulation of peripheral nervous tissue: an investigation into mechanisms" 2015 *J. Phys. Conf. Ser.*, 581:012003.
Wu, "Advanced hepatocellular carcinoma: Treatment with high-intensity focused ultrasound ablation combined with transcatheter arterial embolization," *Radiology*, May 2005; 235(2):659-667.
Wu, "Feasibility of US-guided high-intensity focused ultrasound treatment in patients with advanced pancreatic cancer: Initial experience," *Radiology*, Sep. 2005; 236(3):1034-1040.
Wu, "Time reversal of ultrasonic fields. II. Experimental results," *IEEE Trans. Ultrason., Ferroelectr., Freq. Control*, Sep. 1992; 39(5):567-578.
Wulff, "Effects of ultrasonic vibrations on nerve tissues." *Proceedings of the Society for Experimental Biology and Medicine*, 1951, 76(2):361-366.
Yang, "Neuromodulation of sensory networks in monkey brain by focused ultrasound with MRI guidance and detection" 2018 *Sci. Rep.* 8:7993.
Yang, "Transcranial Ultrasound Stimulation: A Possible Therapeutic Approach to Epilepsy" 2011 *Medical Hypotheses* 76(3):381-83.
Yao, "Dual-mode ultrasound phased arrays for imaging and therapy," Apr. 2004 *Proc. IEEE Int. Symp. Biomed. Imag.*, 1:25-28.
Yao, "Enhanced lesion visualization in image-guided noninvasive surgery with ultrasound phased arrays," Oct. 2001 *Proc. 23$^{rd}$ Annu. Int. Conf. IEEE Eng. Med. Biol. Soc.*, 3:2492-2495.
Yao, "Real-time monitoring of the transients of HIFU-induced lesions," Oct. 2003 *Proc. IEEE Ultrason. Symp.*, 1:1006-1009.
Ye, "Frequency Dependence of Ultrasound Neurostimulation in the Mouse Brain" 2016 *Ultrasound Med Biol.*, 42(7):1512-30.
Yin, "A numerical study of transcranial focused ultrasound beam propagation at low frequency" Apr. 2005 *Phys Med Biol*, 50(8):1821-1836.
Yoo, "Focused ultrasound modulates region-specific brain activity" 2011 *NeuroImage*, 56:1267-1275.
Yoshino, "Effects of focused ultrasound sonodynamic treatment on the rat blood-brain barrier" Mar. 2009 *Anticancer Res*, 29(3):889-895.
Younan, "Influence of the pressure field distribution in transcranial ultrasonic neurostimulation" Aug. 2013 *Med Phys*, 40(8):082902.
Yuh, "Delivery of systemic chemotherapeutic agent to tumors by using focused ultrasound: Study in a murine model," Feb. 2005; *Radiology*, 234(2):431-437.
Zhang, "Defining the optimal age for focal lesioning in a rat model of transcranial hifu" Feb. 2015 *Ultrasound Med Biol*, 41(2):449-455.

\* cited by examiner

Algorithm 3 Optimal Synthesis of Channel Transmit Data for Multiband Transcranial Refocusing

Initialize: SA Imaging
Element waveforms $u_n(t) = 0, \forall n = 1, 2, \ldots, N$  ▷ $N$ number of elements
Target(s) $\rightarrow H_T(f)$  ▷ Size $M_T \times N$
Skull CP(s) $\rightarrow H_C(f)$  ▷ Size $M_C \times N$ 1: for all $i = 1, \ldots, N_F$ do
2:   procedure PERFORM STF($f_i$)
3:     Measure $H_T(f_i), H_C(f_i)$
4:     Evaluate $G_T(f_i)$ and $G_C(f_i)$
5:   end procedure
6:   procedure SOLVE OPTIMIZATION PROBLEM($H_T(f_i), H_C(f_i), u_{opt}(f_i)$)
7:     $W_T = H_T^H H_T, W_C = \left(H_C^H H_C + \gamma_C I\right), \gamma_C > 0$
8:     Lagrange (MNLS): $\boxed{u_{opt}^{(i)} = W_C^{-1} H_T^H \left(H_T W_C^{-1} H_T^H\right)^{\dagger} p_T}$
9:   end procedure
10:   for all $N$ DMUA elements $n = 1, 2, \ldots, N$ do
        $\boxed{u_n(t) = u_n(t) + \Re\left\{u_{opt,n}^*(f_i) e^{j2\pi f_i t} g(t)\right\}}$  ▷ $g(t)$, e.g. raised cosine
11:   end for
12:   procedure PERFORM STF(WB)
13:     Evaluate $G_T(WB)$ and $G_C(WB)$
14:   end procedure
15: end for

Algorithm 1 One-step Optimal Transmit Waveforms for cMTF Synthesis
    Initialize: SA Imaging
        Element waveforms $u_n(t) = 0$, $\forall n = 1, 2, \ldots, N$         ▷ $N$ number of elements
        Target(s): $\{\vec{r}_m, g_m(t)\}_{m=1}^{M_T}$         ▷ Size $M_T \times N$
        Identify Obstacle's Transmission and Critical Points
            Critical Points CP(s): $\{\vec{r}_m\}_{m=1}^{M_C}$         ▷ Size $M_C \times N$
        Define Candidate Transmission Points
1: for all $i = 1, \cdots, N_F$ do
2:     procedure PERFORM NB SA($H_T(f_i), H_C(f_i)$)
3:         Measure $H_T(f_i)$
        $H_T(f_i) = H_{AV}(f_i) H_{VV}(f_i) H_{VT}(f_i)$         ▷
4:         Measure $H_C(f_i)$         ▷
        $H_C(f_i) = H_{AV}(f_i) H_{VV}(f_i) H_{VC}(f_i)$
5:     end procedure
6:     procedure SOLVE OPTIMIZATION PROBLEM($H_T(f_i), H_C(f_i), u_{opt}(f_i)$)
7:         $W_T = H_T^H H_T$, $W_C = (H_C^H H_C + \gamma_C I)$, $\gamma_C > 0$
8:         Complex pressures at target(s): $\{p_T(\vec{r}_m, f_i) = G_m(f_i)\}_{m=1}^{M_T}$
9:         Lagrange (WMNLS): $u_{opt}^{(i)} = W_C^{-1} H_T^H \left(H_T W_C^{-1} H_T^H\right)^\dagger p_T$
10:        Perform NB MTF
11:        Evaluate $G_T(f_i)$ and $G_C(f_i)$
12:     end procedure
13:    for all $N$ DMUA elements $n = 1, 2, \cdots, N$ do
        $u_n(t) = u_n(t) + \Re\left\{u_{opt_n}^*(f_i) e^{j2\pi f_i t} g(t)\right\}$         ▷ $g(t)$, e.g. raised cosine
14:    end for
15:    procedure PERFORM CMTF
16:       Evaluate $G_T(WB)$ and $G_C(WB)$
17:    end procedure
18: end for

FIG. 8B

Algorithm 4 Focused Data Matrix, $X_m$

1: procedure DEFINING FOCUSED DATA MATRIX(DMUA Lattice and RF echo from STF($f_i$), RoI $\vec{r}_m$ & $R, X_m$)
2:     Define RoI $\{\vec{r} : |\vec{r} - \vec{r}_m| < R\}$
3:     for all $N$ DMUA elements $n = 1, 2, \ldots, N$ do
4:         Determine $R_{m,n} = |\vec{r}_n - \vec{r}_m|$ and $R_{m,n}^{\{min, max\}} = R_{m,n} \mp R$ $$X_m(\cdot, i, n) = \mathcal{F}_{f_i}\left\{RF_n\left(\left[\left\lceil\frac{2 * R_{m,n}^{min} * F_s}{c}\right\rceil : \left\lceil\frac{2 * R_{m,n}^{max} * F_s}{c}\right\rceil\right]\right)\right\} \quad (7)$$

where $\mathcal{F}_{f_i}\{\cdot\}$ is a complex NB filter centered at $f_i$ and $\lceil \cdot \rceil$ is the ceiling quantizer.
5:     end for
6: end procedure

FIG. 9

ADAPTIVE REFOCUSING OF ULTRASOUND TRANSDUCER ARRAYS USING IMAGE DATA

CROSS-REFERENCE TO RELATED APPLICATIONS

This application is a Continuation Application of U.S. patent application Ser. No. 16/202,992 filed Nov. 28, 2018, which claims the benefit of U.S. Provisional Application Ser. No. 62/591,308, filed Nov. 28, 2017, each of which is incorporated entirely herein by reference. This application is related to pending U.S. application Ser. No. 13/702,813, published as U.S. Publication No. 2013/144,165 on Jun. 6, 2013, entitled DUAL MODE ULTRASOUND TRANSDUCER (DMUT) SYSTEM AND METHOD FOR CONTROLLING DELIVERY OF ULTRASOUND THERAPY, which is incorporated entirely herein by reference.

STATEMENT REGARDING FEDERALLY SPONSORED RESEARCH OR DEVELOPMENT

This invention was made with government support under NS087887 and NS098781 awarded by National Institutes of Health. The government has certain rights in the invention.

BACKGROUND

In many medical applications, imaging using dual-mode ultrasound arrays (DMUAs), which are a plurality of dual-mode ultrasound transducers (DMUTs) arranged into an array, may be limited by beam distortions caused by a scattering obstacle in a tissue volume of a patient, particularly when the obstacle is positioned between a target region and the ultrasound transducer array. Such obstacles may cause losses in spatial and contrast resolutions, as well as distortions, that may limit the ability of the DMUA to be used for generating sufficient image data or delivering sufficiently focused ultrasound energy for therapy, for example, to a tissue volume including the brain and skull of the patient.

DMUAs may be configured to deliver focused ultrasound (FUS) to the tissue volume of a patient to deliver ultrasound energy to localized regions within the tissue volume. Existing image-based, adaptive refocusing algorithms have been described. For example, U.S. Patent Publication 2013/0144165, entitled "DUAL MODE ULTRASOUND TRANSDUCER (DMUT) SYSTEM AND METHOD FOR CONTROLLING DELIVERY OF ULTRASOUND THERAPY," published Jun. 6, 2013, which is incorporated entirely herein by reference, describes reshaping an imaging or therapy beam using estimated "free space" directivities of the transducers in order to transmit ultrasound energy through intercostal spaces to avoid strongly scattering obstacles, such as a rib cage. However, certain obstacles, such as the skull, may not be avoidable when the target region is the brain, and the array is outside of the patient's skull. Imaging and therapy beams delivered to the target region may be distorted by the obstacle before reaching the target region and even further when echo energy returns to the array for imaging. Not only do these distortions result in loss of focusing gain, but they may also result in shifting the focus from the intended target, which may be undesirable for precisely targeting brain circuits.

Transcranial focused ultrasound (tFUS), has been proposed for various brain conditions, for example, using magnetic resonance (MR) imaging guidance. For example, the use of sub-therapeutic tFUS for the suppression of chemically-induced epileptic activity has been suggested. Temporal lobe epilepsy (TLE) is the most common form of epilepsy and most likely to remain refractory to medications. Recent results demonstrating the feasibility of tFUS in lesion formation, as well as modulation of neural activity in animal models of epilepsy, suggest that a potentially more attractive option for refractory epilepsy patients may be available. In another clinical application, the safe administration of ablative tFUS in a human patient under MR guidance has recently been demonstrated in patients with malignant tumors.

Early efforts to target brain tissue using FUS were performed with the skull removed to minimize the aberrations to the beam. More recent efforts led by several research groups worldwide have triggered a flurry of interest in the application of tFUS for ablation and blood-brain barrier opening. MR guidance is currently used in tFUS applications and is expected to continue to be the main guidance modality due to its high soft-tissue contrast and specificity to a variety of lesions and abnormalities in the brain. However, high-specificity feedback to the tFUS-tissue interactions remains difficult, especially when short bursts of sub-therapeutic tFUS are used.

SUMMARY

In general, the present disclosure relates to dual-mode ultrasound methods and related systems that provide ultrasound refocusing for ultrasound transducer arrays, particularly DMUAs, based on image data. The refocusing may be adaptive in nature and capable of refocusing in real-time for various applications, such as high-intensity focused ultrasound (HIFU) in which therapy shots utilize a plurality of therapy bursts and imaging feedback alternating between one another in the sub-millisecond range. In one or more embodiments, the method may utilize image data at a plurality of frequencies to evaluate FUS responses in the tissue volume including an obstacle. The multiband image data may be used to provide a refocused ultrasound wavefront for further imaging or therapy. In one or more embodiments, the method may utilize one or more transmission points used to deliver ultrasound energy through the obstacle. The transmission points may be used to determine efficient frequencies for transmitting ultrasound energy through the obstacle for further imaging or therapy. In one or more embodiments, the method may utilize one or more virtual arrays to characterize propagation through different regions of the tissue volume including the obstacle. The virtual arrays may be cascaded to provide a refocused ultrasound wavefront to be delivered to one or more target points for further imaging or therapy. In one or more embodiments, a dual mode ultrasound transducer system for imaging or therapy may implement any of the methods described herein.

Various aspects of the present disclosure may relate to a dual mode ultrasound transducer imaging or therapy method. The method may include generating initial image data of a tissue volume in an imaging field of view using an array of ultrasound transducer elements. The array of ultrasound transducer elements may be configured to deliver multiband ultrasound energy to the tissue volume including a target region and to receive echo ultrasound energy from the tissue volume. The tissue volume may include an ultrasound distorting obstacle in the imaging field of view (that is, the target region may be disposed distal to the obstacle such that at least a portion of the ultrasound energy delivered to one or more target points the target region must pass through the obstacle). The method may also include identifying one or more target points in the target region and one or more critical points associated with the obstacle in the tissue volume. The method may further include synthesizing excitation waveforms for driving the array of ultrasound transducer elements based on the one or more target points and the one or more critical points. The method may also include generating focused image data of the target region using the excitation waveforms to drive the array of ultrasound transducer elements. The focused image data may include measurements in a plurality of different frequency bands using the ultrasound transducer elements. The focused image data may also include information associated with the one or more target points and information associated with the one or more critical points. The method may further include determining focusing gains based on the focused image data. The focusing gains may further include at least a target focusing gain associated with one of the target points and a critical focusing gain associated with one of the critical points. Further, the method may include, in response to determining that both the target focusing gain is no less than a minimum threshold and that the critical focusing gain is no greater than a maximum threshold, configuring delivery of refocused ultrasound energy to the tissue volume including the one or more target points in the target region based on the excitation waveforms for imaging or therapy. Still further, the method may include, in response to determining that either the target focusing gain is less than the minimum threshold or that the critical focusing gain is greater than the maximum threshold, synthesizing an iteration of the excitation waveforms based on the focused image data and generating refocused image data using the iteration of the excitation waveforms to drive the array of ultrasound transducer elements.

Various aspects of the present disclosure may relate to a dual mode ultrasound transducer imaging or therapy method that may include generating initial image data of a tissue volume in an imaging field of view using an array of ultrasound transducer elements. The array of ultrasound transducer elements may be configured to deliver multiband ultrasound energy to the tissue volume including a target region and to receive echo ultrasound energy from the tissue volume. The tissue volume may include an ultrasound distorting obstacle in the imaging field of view (that is, the target region may be disposed distal to the obstacle such that at least a portion of the ultrasound energy delivered to one or more target points in the target region must pass through the obstacle). The method may also include determining one or more critical points associated with the obstacle based on the initial image data. The critical points may be avoided when propagating focused ultrasound energy to the target region. The method may further include determining one or more transmission points associated with the obstacle. Each transmission point is different than any of the critical points. The transmission points may be used for propagating focused ultrasound energy to the target region. Further, the method may include generating focused image data of the tissue volume including the target region and the obstacle using the array of ultrasound transducer elements. The focused image data may include information associated with one or more of the transmission points for a plurality of different frequency bands within a bandwidth of the array of ultrasound transducer elements. Further still, the method may include determining one or more efficient frequency bands for one or more of the transmission points based on the focused image data and synthesizing excitation waveforms for delivering refocused ultrasound energy to the one or more target points in the target region based on one or more of the transmission points and one or more associated efficient frequency bands.

Various aspects of the present disclosure may relate to a dual mode ultrasound transducer imaging or therapy method that may include generating initial image data of a tissue volume in an imaging field of view using an array of ultrasound transducer elements. The array of ultrasound transducer elements may be configured to deliver multiband ultrasound energy to the tissue volume including a target region and to receive echo ultrasound energy from the tissue volume. The tissue volume may include an ultrasound distorting obstacle in the imaging field of view (that is, the target region may be disposed distal to the obstacle such that at least a portion of the ultrasound energy delivered to one or more target points the target region must pass through the obstacle). The method may also include determining one or more first virtual elements of a first virtual array associated with a distal surface of the obstacle based on the initial image data. The method may further include determining one or more second virtual elements of a second virtual array associated with a proximal surface of the obstacle based on the initial image data. Also, the method may include estimating a first propagation operator between the one or more of the target points in the target region and the one or more second virtual elements of the first virtual array. Further, the method may include estimating a second propagation operator between the one or more first virtual elements and the one or more second virtual elements based on the initial image data. Furthermore, the method may include estimating a third propagation operator between the one or more second virtual elements and one or more of the ultrasound transducer elements of the array. Further still, the method may include configuring the delivery of refocused ultrasound energy to the one or more target points in the target region by solving an optimization problem on a cascade of the first, second, and third propagation operators or solving an optimization problem for each of the first, second, and third propagation operators.

Various aspects of the present disclosure may relate to a dual mode ultrasound transducer system. The system may include an array of ultrasound transducer elements configured to deliver multiband ultrasound energy to a tissue volume including a target region and to receive echo ultrasound energy from the tissue volume. The tissue volume may include an ultrasound distorting obstacle in an imaging field of view of the array (that is, the target region may be disposed distal to the obstacle such that at least a portion of the ultrasound energy delivered to the target region must pass through the obstacle). The system may also include a control apparatus comprising at least one processor configured to execute any one of the imaging or therapy methods.

The above summary is not intended to describe each embodiment or every implementation of the present disclosure. A more complete understanding will become apparent and appreciated by referring to the following detailed description and claims taken in conjunction with the accompanying drawings.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIG. 8A is an algorithm for synthesis of multiple-focus patterns using multiband excitation waveforms.

FIG. 8B is another algorithm for refocusing ultrasound through an obstacle using multiband excitation waveforms.

FIG. 9 is an algorithm for generating a focused data matrix.

Figure 1:
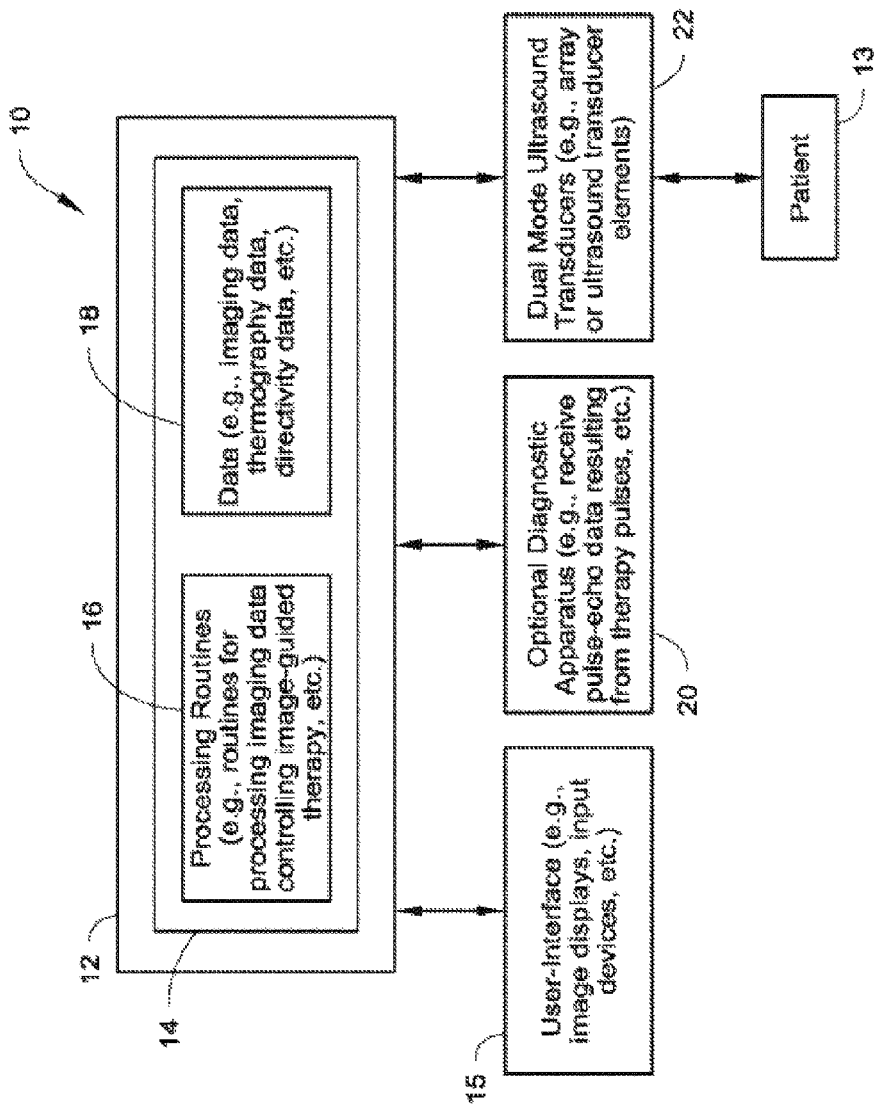
FIG. 1 is a block diagram of an ultrasound imaging or therapy system.

In the following detailed description of illustrative embodiments, reference is made to the accompanying figures of the drawing which form a part hereof, and in which are shown, by way of illustration, specific embodiments which may be practiced. It is to be understood that other embodiments may be utilized and structural changes may be made without departing from (for example, still falling within) the scope of the disclosure presented hereby.

DETAILED DESCRIPTION OF EXEMPLARY EMBODIMENTS

The present disclosure relates generally to ultrasound delivery apparatus or systems and methods for using ultrasound energy in imaging and therapy of tissue. The present disclosure further pertains to systems and methods that utilize ultrasound in various medical applications, such as imaging or therapy of brain tissue (for example, tumor or lesion), vasculature (for example, plaque growth), nerve structure (for example, denervation), cardiac tissue (for example, cardiac ablation), and drug delivery (for example, activation of drug in tissue). In particular, the present disclosure relates to focused ultrasound (FUS) imaging or therapy, such as transcranial focused ultrasound (tFUS), when the tissue volume includes a target region and an unavoidable obstacle between the ultrasound delivery apparatus and the target region.

In particular, the present disclosure relates to techniques for optimal refocusing of ultrasound energy that may compensate for beam distortion through tissue or other obstacles. These techniques may utilize ultrasound image data to characterize the transmission of ultrasound through tissue and obstacles in the path of the beam. In addition, these techniques may maximize efficacy and minimize downsides of using FUS in a variety of therapies. A dual-mode ultrasound imaging or therapy system may incorporate these techniques to provide real-time imaging or therapy.

The present disclosure may provide dual-mode ultrasound methods and related systems that provide ultrasound refocusing for ultrasound transducer arrays, particularly DMUAs, based on image data. The refocusing may be adaptive in nature and capable of refocusing in real-time for various applications, such as high-intensity focused ultrasound (HIFU) in which therapy shots utilize a plurality of therapy bursts and imaging feedback alternating between one another in the sub-millisecond range. In one or more embodiments, the method may utilize image data at a plurality of frequencies to evaluate FUS responses in the tissue volume including an obstacle. The multiband image data may be used to provide a refocused ultrasound wavefront for further imaging or therapy. In one or more embodiments, the method may utilize one or more transmission points used to deliver ultrasound energy through the obstacle. The transmission points may be used to determine efficient frequencies for transmitting ultrasound energy through the obstacle for further imaging or therapy. In one or more embodiments, the method may utilize one or more virtual arrays to characterize propagation through different regions of the tissue volume including the obstacle. The virtual arrays may be cascaded to provide a refocused ultrasound wavefront to be delivered to one or more target points for further imaging or therapy. In one or more embodiments, a dual mode ultrasound transducer system for imaging or therapy may implement any of the methods described herein.

In some embodiments, unfocused imaging may be used to generate unfocused image data or initial image data. Non-limiting examples of imaging modes used to generate initial image data include synthetic aperture (SA) or coded synthetic aperture (cSA) imaging.

In some embodiments, focused imaging may be used to generate focused image data or refocused image data. Non-limiting examples of imaging modes used to generate focused image data include single transmit-focus (STF), multiple transmit-focus (MTF), or coded multiple transmit-focus (cMTF) imaging.

In some embodiments, one or more propagation operators may be determined based on image data. The image data may be used to define or determine one or more structures, such as one or more control points, define one or more virtual arrays, or define one or more propagation operators. One or more of these structures may be used to synthesize the refocused ultrasound wavefront. Non-limiting examples of control points include targets points, critical points, transmission points, or virtual array points. Virtual arrays may be defined based on one or more surfaces of the obstacle. Propagation operators may describe complex transformations between two points within the tissue volume.

The image data may be used to solve a new optimization problem, which may be incorporated into a refocusing algorithm. The new optimization problem may utilize a multiband analysis of ultrasound propagation through a tissue volume. The algorithm may be used to synthesize optimized ultrasound beams based on the multiband analysis. The optimized ultrasound beams may be evaluated using image data for feedback. For example, any of echogenicity, heating, cavitation, or tissue displacement may be used. A higher response to FUS may be desirable in some areas of the tissue volume, whereas a lower response to FUS may be desirable in other areas of the tissue volume. Additional optimized excitation waveforms may be generated iteratively, if needed, to improve performance.

The success of tFUS intervention may help patients in several ways. For example, patients suffering from epilepsy may see benefits in response to: (1) limiting the therapeutic exposure to the targeted lesions thus making the referral easier, (2) potentially providing additional options for patients with bilateral lesions who are currently ineligible for surgery, and (3) providing nonablative treatment options for most patients by using sub-therapeutic tFUS exposures with and without drugs. These benefits are also applicable to cancer patients and others with focal brain lesions. In general, the techniques described herein may allow for greater clinical acceptance of tFUS as a promising treatment modality that may offer some hope for patients that are currently left without options.

Exemplary methods, apparatus, and systems shall be described with reference to FIG. 1 to FIG. 14. It will be apparent to one skilled in the art that elements or processes (for example, including steps thereof) from one embodiment may be used in combination with elements or processes of the other embodiments, and that the possible embodiments of such methods, apparatus, and systems using combinations of features set forth herein is not limited to the specific embodiments shown in the Figures and/or described herein. Further, it will be recognized that the embodiments described herein may include many elements that are not necessarily shown to scale. Still further, it will be recognized that timing of the processes and the size and shape of various elements herein may be modified but still fall within the scope of the present disclosure, although certain timings, one or more shapes and/or sizes, or types of elements, may be advantageous over others.

As used herein, the term "system" may refer to apparatus with a number of elements (for example, means, devices, etc.) specifically connected with each other by way of electrical connection and being adapted to the specific functions of each element as described herein.

As used herein, "therapeutic" ultrasound energy, beams, or waveforms (for example, energy formed of bursts, pulses, or other spectral content) may refer to energy used to provide therapy to a patient. The characteristics of therapeutic ultrasound energy may vary depending on the particular therapy application and the particular tissue to insonate. In some cases, therapeutic energy may have characteristics sufficient for ablation.

As used herein, "subtherapeutic" ultrasound energy, beams, or waveforms (for example, energy formed of bursts, pulses, or other spectral content) may refer to energy having characteristics that are below a therapeutic level, which may depend on particular tissue characteristics or therapy. For example, subtherapeutic ultrasound energy may have characteristics below those used for ablation therapy but sufficient for performing different functions. For example, subtherapeutic ultrasound energy may be high enough to create a bioeffect such as localized tissue heating, but the effect may be limited in terms of magnitude (for example, ~1 deg. C. temperature rise) and duration (~1 second). Any effect due to a subtherapeutic beam may be highly transient with the bioeffect being reversible. The time duration may be limited but large enough to cause significant bioeffects, for example, in neuromodulation or drug delivery applications, and the FUS intensity may be at the subtherapeutic levels.

As used herein, "imaging" ultrasound energy, beams, or waveforms (for example, energy formed of bursts, pulses, or other spectral content) may refer to energy used to image. In general, imaging ultrasound energy may be considered a subset of subtherapeutic ultrasound energy that is low enough to avoid all bioeffects. Imaging ultrasound energy may be used in conjunction with therapeutic or other subtherapeutic ultrasound energy. Imaging ultrasound energy may have characteristics below those used for ablation therapy but sufficient for performing imaging. In some cases, image data collected due to transmissions of imaging ultrasound energy (pulses) may be referred to as pulse-echo data or echo data.

As used herein, the term "coded imaging" or "coded excitation" or "multi-modal coded excitation" (MMCE) refers to using multiple simultaneous codes on transmit to insonate a region of interest (RoI). Echoes from the RoI may be separated in the receive chain using appropriate filtering to produce multiple image lines in parallel, which may increase frame rate.

As used herein, the terms "proximal" and "distal" refer to directions relative to the array of ultrasound transducer elements. Distal describes a direction further away from the array, and proximal describes a direction closer toward the array.

As used herein, the terms "associated," "corresponding," and "related" refer to two or more elements having some physical or functional relationship. For example, a point associated with an object may mean that the point is disposed within, on, adjacent to, or proximate to the object. As another example, image data associated with an excitation vector may mean that the image data was produced in response to transmitting ultrasound energy according to the excitation vector.

As used herein, the term "excitation vector" refers to parameters used to drive the DMUTs of an array to produce ultrasound energy, particularly in a narrow frequency band or at a discrete frequency. The excitation vector may be an array of elements, and each array element may correspond to a different DMUT of the array.

As used herein, the term "excitation waveform" refers to the characterization of the driving signal used to drive one DMUT to produce ultrasound energy for one transmission or measurement. That is, the excitation waveform may define the ultrasound beam delivered by the DMUT. The excitation waveform may be narrowband, wideband, or multiband. Wideband may refer to a continuous or discrete range of frequencies with the bandwidth of the DMUT. Multiband may refer to multiple frequency bands or multiple discrete frequencies within the bandwidth of the DMUT.

As used herein, the term "wavefront" refers to the characterization of the excitation waveforms used to collectively drive the DMUA to produce a wavefront of ultrasound energy. That is, the wavefront may characterize the sum of the ultrasound beams delivered by the DMUA. Wavefronts may be generated based on different types of imaging modes.

As used herein, the terms "determine," "estimate," "compute," "synthesize," and "generate" may be used interchangeably to refer generally to producing an output in response to, or based on, an input. However, these terms may also refer to more specific definitions depending on the context.

FIG. 1 shows an exemplary dual mode ultrasound transducer system 10 including control apparatus 12, which may include one or more processing apparatuses, and one or more dual-mode ultrasound transducer elements 22, which may be formed as an array of ultrasound transducers, such as a DMUA, to transmit of ultrasound energy waveforms, preferably multiband waveforms, and to receive ultrasound energy echoes for imaging (for example, in a pulse-echo mode) or to deliver ultrasound energy waveforms for therapy (for example, in a transmit mode). The control apparatus 12 may be operably coupled to the array of ultrasound transducers 22, for example, using a control channel for each of the ultrasound transducers in a multichannel configuration to facilitate providing imaging or therapy waveforms. The ultrasound transducers 22 may be configurable for operation, for example, with respect to phase/delay, amplitude, or spectral content. In a therapy mode, the operation of the ultrasound transducers 22 may be configured to produce at least one type of therapeutic responses, such as thermal, mechanical, or mixed therapeutic responses, in a tissue volume of a patient 13.

In particular, the array of ultrasound transducer elements 22 may be configured to deliver multiband ultrasound energy to the tissue volume including a target region and to receive echo ultrasound energy from the tissue volume. The tissue volume may include an ultrasound distorting obstacle in the imaging field of view. The target region may be disposed distal to the obstacle such that at least a portion of the ultrasound energy delivered to one or more target points the target region must pass through the obstacle.

The system 10 may use a multi-channel driver to drive the transducer elements 22 of the array. The system 10 may generate various types of image data using the dual-mode ultrasound array (DMUA) of transducer elements 22. For example, adaptive refocusing for improved imaging and therapy can be achieved using multiband focused data matrices generated based on image data. Further, coded excitation using multi-channel arbitrary waveform generators may be used to target multiple points within the tissue volume concurrently.

The array of ultrasound transducers 22 may include any suitable configuration. The array of ultrasound transducers 22 may be used to deliver ultrasound energy for imaging and optionally for therapy. The ultrasound transducers 22 may be configured to deliver ultrasound energy to at least a portion of a tissue volume including a target region and to receive ultrasound energy from the target region. The control apparatus 12 may be configured to control conveyance of ultrasound energy to one or more of the ultrasound transducers 22 and control reception of ultrasound energy (for example, ultrasound echoes).

In general, imaging utilizes one or more pulses of ultrasound energy waves, or wavefronts, to insonate a field of view and the echo of each pulse may be received as image data. The quality of DMUA images can be improved by the use of signal processing and reconstructive imaging. Imaging signals may be conveyed according to one or more imaging modes. Furthermore, despite the limited fractional bandwidth, coded excitation may be used to improve the signal to noise and spatial resolution of a DMUA. Non-limiting examples of imaging modes include synthetic aperture (SA) imaging or B-mode imaging, coded synthetic aperture (cSA) imaging, M2D-mode strain imaging, quadratic B-mode (QB-mode) imaging, inverse scattering reconstruction, thermal imaging, single transmit focus (STF) imaging, multiple transmit-focus (MTF) imaging, or coded multiple transmit-focus (cMTF) imaging.

In some cases, the system 10 may be capable of reporting frame rates of up to about 1000 frame per second (fps) in STF imaging or even higher. High frame rate capability may be beneficial for performing refocusing adaptively (for example, in real-time), which may allow for generating and testing hundreds of focusing patterns within a fraction of a second. This adaptive refocusing may allow for corrections due to aberrations of ultrasound-distorting obstacles, such as a skull, as well as almost instantaneous corrections due to changes in the imaging field of view.

The system 10 may be used to perform one or more therapeutic operations or produce one or more therapeutic responses (for example, with respect to a patient 13). The therapy may be thermal or non-thermal. The therapy may be invasive or non-invasive. In particular, the system 10 may be used in non-invasive FUS therapy that produces responses in one or more target regions of a patient 13, such as tFUS therapy that produces responses in the brain tissue of the patient. Non-limiting other examples of FUS therapy include applying ultrasound energy to vasculature (for example, to treat plaque growth by thermally treating the base of plaque on a vessel wall, thrombolysis, or varicose veins), the nervous system (for example, denervation of at least portions of one or more nerves, such as in the renal region), tumors or cancerous tissue (for example, ablation of tissue or lesion formation using a high intensity focused ultrasound beam cardiac tissue (for example, cardiac ablation), for drug delivery (for example, activation of drug provided in tissue), or for treating uterine fibroids.

The control apparatus 12 may be configured to generate therapy signals to drive one or more of the plurality of ultrasound transducers of the array 22 to deliver a plurality of sequential therapy bursts of ultrasound energy to the tissue volume. The control apparatus 12 may be configured to generate control image data (for example, directivity data, high resolution image data, mechanical response data such as displacement and/or strain data, test pattern data, thermal response data, cavitation and boiling activity data, etc.) The control image data generated following delivery of a therapy burst may be used to generate therapy signals to drive one or more of the plurality of ultrasound transducers to deliver subsequent ultrasound energy (for example, the definition of the subsequent ultrasound energy takes into consideration the control image data, or in other words, takes into consideration image data that reflects the response of the tissue to previous ultrasound energy). A therapy burst may be part of a shot of therapy. Each shot of therapy may include a plurality of therapy bursts. In one or more embodiments, control image data may be generated after the delivery of each therapy burst such that the following therapy burst in the sequence of therapy bursts (for example, the next therapy burst in the therapy shot) is defined based at least in part on the response caused by the prior therapy burst. In this manner, each therapy burst of ultrasound energy (at least after the first therapy burst) can be guided based on the control image data generated due to the previous therapy burst. The relationship between therapy shots and bursts is described in U.S. application Ser. No. 13/702,813, published as U.S. Publication No. 2013/144165, entitled DUAL MODE ULTRASOUND TRANSDUCER (DMUT) SYSTEM AND METHOD FOR CONTROLLING DELIVERY OF ULTRASOUND THERAPY.

The system 10 may be configured for both imaging and therapy, for example, when delivering therapy using real-time imaging feedback. Real-time intensity modulation (or generally beam resynthesis, which may include adjustment of phase/delay, amplitude, or spectral content of the ultrasound energy waveforms) may be performed based on image data with millisecond time resolution.

The ultrasound energy delivered by the ultrasound transducers 22 may be therapeutic or subtherapeutic. For example, assuming a 1-second therapy beam can generate a thermal lesion at intensity $I_O$, then a beam with the same duration and spatial pattern, but with focal intensity $I_O/20$ is likely to cause temperature change at the focus by a few degrees centigrade (C). This may be a reversible change and may be unlikely to cause any permanent lesion. Consequently, this beam may be considered and described as subtherapeutic. This subtherapeutic beam can serve as a test beam for measuring responses at one or more control points. Likewise, a beam (for example, for use in cavitation therapy) with the same focal intensity, but with a duration in the range of about 10 microseconds to less than about 1 millisecond (for example, sub-milliseconds) may not form thermal lesions, but can serve as a test subtherapeutic beam for cavitation activity.

Focusing gain may be determined based on delivering ultrasound energy to the tissue volume and measuring a response at one or more control points. Focusing gain may describe the amount of ultrasound energy delivered to a control point. For example, focusing gain may represent a measurement of echogenicity, heating, cavitation, or tissue displacement at a control point. Measuring heating or heating rate may be useful in determining a control point's response to therapy ultrasound energy. In some cases, focusing gain may be a relative measure, such as a ratio between ultrasound energy received based on a focused excitation waveform compared to an unfocused excitation waveform.

Control points may include target points, critical points, transmission points, and virtual array points. In particular, subtherapeutic ultrasound energy or imaging ultrasound energy may be used to provide image data to evaluate focusing gain. The feedback from the ultrasound energy may be measured to provide an indication of focusing gain at one or more control points. Non-limiting types of measurements that may facilitate determining focusing gain include: echogenicity (for example, using image data), heating using ultrasound thermography (such as tUST), cavitation using bubble oscillations or cavitation noise, or tissue displacement using speckle tracking.

Echogenicity indicates the reflection of ultrasound energy within the tissue volume. In some cases, reduced echogenicity at a location may be indicative of a reduction in incident power. Reducing echogenicity may be useful to avoid excessive heating at those locations.

Subtherapeutic ultrasound energy may be used to cause localized heating by delivering ultrasound energy for a duration on the order of tens of milliseconds. For example, the subtherapeutic ultrasound energy may be delivered for a duration from about 10 milliseconds to about 100 milliseconds to produce localized heating in the tissue volume, and heating may be measured using ultrasound thermography at one or more control points (for example, at or near a target point).

Also, the subtherapeutic ultrasound energy may be used to cause localized cavitation by delivering ultrasound energy for a duration on the order of tens of microseconds. For example, the subtherapeutic ultrasound energy may be delivered for a duration from about 10 microseconds to about 100 microseconds to produce localized cavitation in the tissue volume, and cavitation may be measured using bubble oscillations or cavitation noise at one or more control points (for example, at or near a target point).

Further, the subtherapeutic ultrasound energy may be used to cause tissue displacement by delivering ultrasound energy for a duration on the order of hundreds of microseconds. For example, the subtherapeutic focused ultrasound energy may be delivered for a duration from about 100 microseconds to about 1000 microseconds to provide acoustic radiation force to produce tissue displacements in the tissue volume, and tissue displacement may be measured using speckle tracking at one or more control points (for example, at or near a target point).

In some applications, in which therapy ultrasound energy is to be configured and delivered based on the focusing gain, the control apparatus 12 may measure heating, particularly at critical points.

The control apparatus 12 may include data storage 14. Data storage 14 may allow for access to processing programs or routines 16 and one or more other types of data 18 that may be employed to carry out the various functionality of the system 10 as described herein.

For example, processing programs or routines 16 may include programs or routines for performing computational mathematics, matrix mathematics, compression algorithms (for example, data compression algorithms), calibration algorithms, image construction algorithms, inversion algorithms, signal processing algorithms, standardization algorithms, comparison algorithms, vector mathematics, or any other processing required to implement one or more functions as described herein. Non-limiting examples of functions that may be carried out by the control apparatus 12 include to: synthesize excitation waveforms for DMUTs, provide multiple modes of imaging, provide therapy, perform pattern test processes, perform fusion of data resulting from multiple modes of imaging, generate a graphical user interface to allow a user to input commands, carry out motion tracking or speckle tracking, identify critical points, specify virtual thermometry probes (for example, based on ultrasound thermometry), or modulate therapy bursts (for example, amplitude and/or duration). Exemplary mathematical formulations/equations that may be used in the systems and methods described herein are more specifically described herein.

Data 18 may include, for example, sampled pulse-echo information, control image data such as directivity data, image data which may be generated in response to various synthetic aperture imaging or transmit focus imaging, thermal response data, mechanical response data including displacement/strain data associated with the target region such as measurements of tissue characteristics, results from one or more processing programs or routines employed according to the disclosure herein, or any other data that may be necessary for carrying out the one or more processes or methods described herein. The pulse-echo information may be sampled or collected using the one or more transducer elements 22.

In one or more embodiments, the system 10 may be implemented using one or more computer programs executed on programmable computers, such as computers that include, for example, processing capabilities (for example, computer processing units (CPUs), graphical processing units (GPUs), data storage (for example, volatile or non-volatile memory and/or storage elements), input devices, and output devices. Program code and/or logic described herein may be applied to input data to perform functionality described herein and generate desired output information. The output information may be applied, or otherwise used, as input to, or by, one or more other devices and/or processes as described herein.

The program(s) or routine(s) used to implement the processes described herein may be provided using any programmable language, for example, a high-level procedural and/or object orientated programming language that is suitable for communicating with a computer system. Any such programs may, for example, be stored on any suitable device, for example, a storage media, readable by a general or special purpose program, computer, or a processor apparatus for configuring and operating the computer (such as a microprocessor) when the suitable device is read for performing the procedures described herein. In other words, at least in one embodiment, the system 10 may be implemented using a computer readable storage medium, configured with one or more computer programs, where the storage medium so configured causes the computer to operate in a specific and predefined manner to perform functions described herein.

Likewise, the system 10 may be configured at a remote site (for example, an application server) that allows access by one or more users via a remote computer apparatus (for example, via a web browser), and allows a user to employ certain functionality according to the present disclosure (for example, user accesses a graphical user interface associated with one or more programs to process data).

The control apparatus 12, may be, for example, any fixed or mobile computer system (for example, a personal computer or minicomputer, for example, with CPUs, GPUs, etc.). The exact configuration of the computing apparatus is not limiting and essentially any device capable of providing suitable computing capabilities and control capabilities may be used. Further, various peripheral devices, such as a computer display, mouse, keyboard, memory, printer, scanner, etc. are contemplated to be used in combination with the control apparatus 12, such as for visualization of imaging results.

Further, in one or more embodiments, any output (for example, an image, image data, an image data file, a digital file, a file in user-readable format, etc.) may be analyzed by a user, used by another machine that provides output based thereon, etc.

As described herein, a digital file may be any medium (for example, volatile or non-volatile memory, any tangible memory medium, etc.) containing digital bits (for example, encoded in binary, trinary, etc.) that may be readable and/or writeable by control apparatus 12 described herein.

Also, as described herein, a file in user-readable format may be any representation of data (for example, ASCII text, binary numbers, hexadecimal numbers, decimal numbers, audio, graphical) presentable on any medium (for example, paper, a display, sound waves, etc.) readable and understandable by a user.

Generally, the methods and systems as described herein may utilize algorithms implementing computational mathematics (for example, matrix inversions, substitutions, Fourier transform techniques, etc.) to reconstruct the images described herein (for example, from pulse-echo data).

In view of the above, it will be readily apparent that the functionality as described in one or more embodiments according to the present disclosure may be implemented in any manner as would be known to one skilled in the art. As such, the computer language, the computer system, or any other software/hardware which is to be used to implement the processes described herein shall not be limiting on the scope of the systems, processes, or programs (for example, the functionality provided by such systems, processes or programs) described herein.

One will recognize that a graphical user interface 15 may be used in conjunction with the embodiments described herein. The user interface may provide various features allowing for user input thereto, change of input, importation or exportation of files, or any other features that may be generally suitable for use with the processes described herein. For example, the user interface may allow default values to be used or may require entry of certain values, limits, threshold values, or other pertinent information. Any input devices (for example, as part of a graphical user interface) to the system may be used that allow a user of the therapy system 10 to input commands, or input any other information (for example, to select target points or critical points). For example, a key pad, a mouse, a touch screen, or any other input device may be used.

The methods described in this disclosure, including those attributed to the systems, or various constituent components, may be implemented, at least in part, in hardware, software, firmware, or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, image processing devices, or other devices. The term "control apparatus," "controller," "processor," or "processing circuitry" may generally refer to any of the foregoing circuitry, including processing circuitry, alone or in combination with other logic circuitry, or any other equivalent circuitry.

Such hardware, software, and/or firmware may be implemented within the same device or within separate devices to support the various operations and functions described in this disclosure. In addition, any of the described components may be implemented together or separately as discrete but interoperable logic devices. Depiction of different features, for example, using block diagrams, etc., is intended to highlight different functional aspects and does not necessarily imply that such features must be realized by separate hardware or software components. Rather, functionality may be performed by separate hardware or software components, or integrated within common or separate hardware or software components.

When implemented in software, the functionality ascribed to the systems, devices and methods described in this disclosure may be embodied as instructions on a computer-readable medium such as RAM, ROM, NVRAM, EEPROM, FLASH memory, magnetic data storage media, optical data storage media, or the like. The instructions may be executed by one or more processors to support one or more aspects of the functionality described in this disclosure.

Optional diagnostic apparatus 20 may be used in imaging. For example, the optional diagnostic apparatus 20 may include apparatus for receiving pulse-echo data resulting from the delivery of therapy pulses. For example, although imaging described herein is generally performed using the array 22 (for example, generating imaging pulses and receiving echoes as a result thereof), a diagnostic apparatus may be used to receive pulse-echo data that results from the application of ultrasound energy to the tissue volume. For example, a separate apparatus (for example, separate from the array 22), which may include a linear array imaging probe, may receive or capture pulse-echo data in response to delivering ultrasound imaging energy waveforms using the array. It will be recognized that any such additional diagnostic apparatus may be used to capture such data.

In the case of capturing pulse-echo data resulting from the delivery of ultrasound energy pulses, such captured data may be used to characterize the ultrasound energy waveform's focusing quality at the target location. In some embodiments, two acquisitions for imaging can be separated by time or frequency, for example, 400 microseconds. The two echoes can be correlated near an ultrasound energy pulse to produce tissue displacements at the focus, which may be characteristic of the local mechanical tissue response to the therapy beam at diagnostic level (for example, thermal expansion pulse). Alternatively, QB-mode imaging can be applied to characterize cavitation activity resulting from short-duration ultrasound energy waveforms.

Figure 2A:
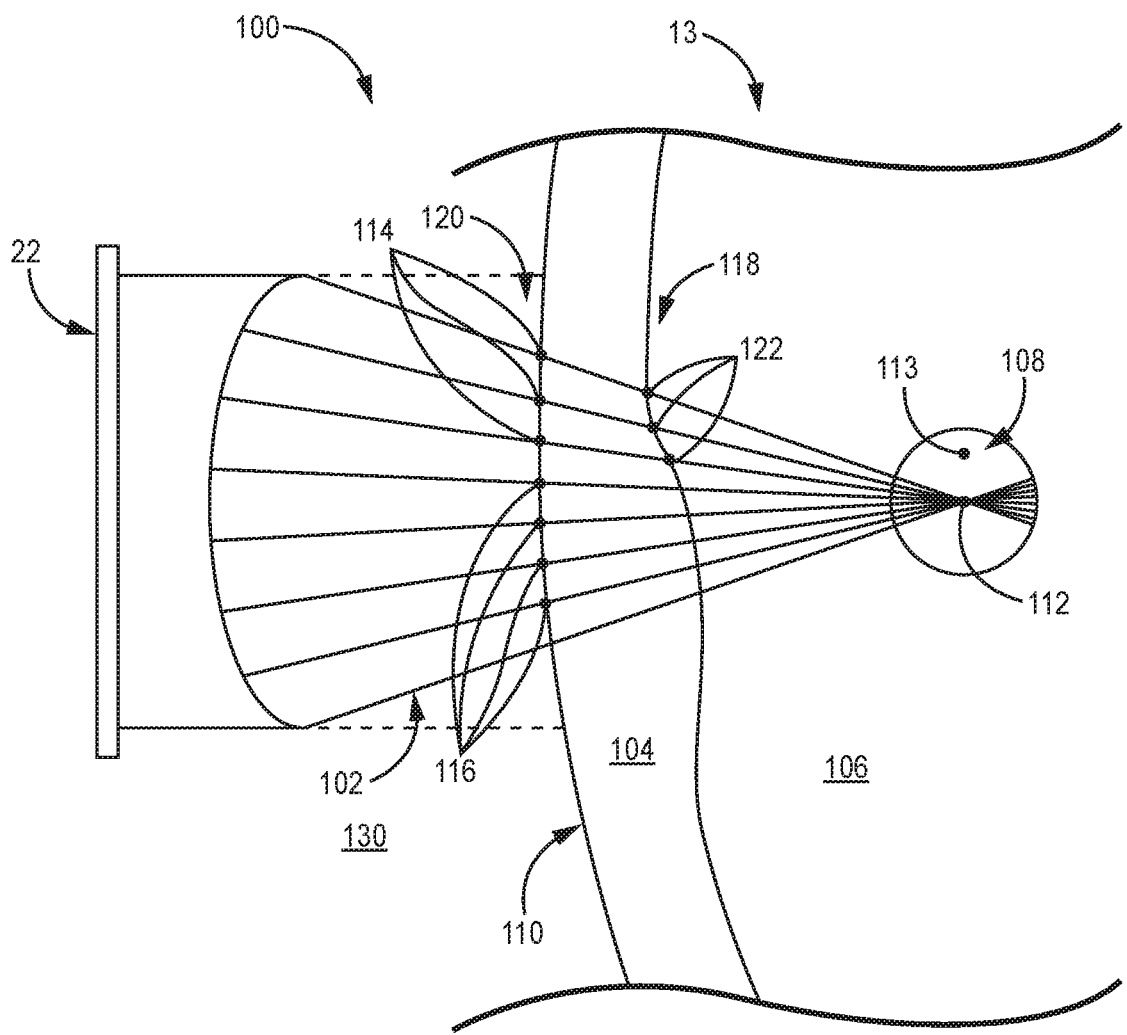
FIG. 2A is a top-down view of an ultrasound imaging or therapy system used with a patient.

FIG. 2A shows a top-down view illustrating an ultrasound transducer array 22 directing beams of ultrasound energy 102 into a patient 13 having a tissue volume 110. The tissue volume 110 may include a target region 108 (for example, a region of tissue in the brain), an obstacle 104 (for example, a skull, a rib cage, a spinal vertebra, or a surgical scar), and other regions associated therewith, such as regions 106, 130 in the path of the ultrasound beams from the array 22 to the target region 108. The obstacle 104 may also be described as a second propagation region. In various applications, the obstacle 104 may not be avoidable when transmitting ultrasound energy 102 between the array 22 and the target region 108, particularly the target points 112, 113. As illustrated, the beam of ultrasound energy 102 is focused on only target point 112, but a multiple transmit technique may be used to focus on both target points 112, 113 simultaneously. Brain tissue may define a first propagation region 106. The array 22 may be positioned as close to the obstacle 104 as possible, but a distance may be present between the array 22 and the obstacle 104. The region between the obstacle 104 and the array 22 may be described as a third propagation region 130.

The obstacle 104 may be non-uniform in terms of ultrasound energy response, for example, due to changes in thickness, shape, or composition. In other words, the obstacle 104 may be an ultrasound distorting obstacle and may have non-uniform ultrasound propagation characteristics.

As illustrated, for example, some portions of the obstacle 104 are thicker or thinner than other portions. The beam of ultrasound energy 102 may need to pass through such uneven or non-uniform portions of the obstacle 104, particularly in some non-invasive applications (such as transcranial focused ultrasound).

The array may be used to generate initial image data to identify one or more control points of the tissue volume 110, such as one or more target points 112, 113 within the target region 108 (for example, the one or more target points may be selectable by the user interface), one or more critical points 116 associated with the obstacle 104 (for example, at or near a thick portion of the skull), or one or more transmission points 114 associated with the obstacle 104 (for example, at or near a thin portion of the skull). The initial image data may be generated using a wide field of view. Subsequently, focused image data may be generated using a smaller or narrower field of view.

One or more target points within the target region may be identified (for example, target points on a brain tumor to be treated) in image data generated based on pulse-echo data received by one or more of the plurality of ultrasound transducers of the array 22 (for example, SA imaging may be used to produce image data for use in identifying one or more target points). As is further defined herein, other control points may be identified, such as critical points related to an obstacle between the target points and the array 22. In one example, an image may be presented on a user interface allowing a user to select one or more control points, such as a critical point known to the user (such as a nerve in the path to the target region). In another example, one or more critical points may be determined according to an algorithm to automatically add, or at least suggest adding, critical points based on image data (for example, non-target points exceeding focusing gain thresholds).

Each of the transmission points 114 and critical points 116 may correspond to a point in a geometric point spread function of the array 22. For example, the transmission points 114 and critical points 116 may be selected from the group of points that lie on the lines, or adjacent or proximate to the lines, that define the paths of the ultrasound beam 102. The transmission points 114 and critical points 116 may be associated with the obstacle 104 but need not lie within the volume of the obstacle. More specifically, in some embodiments, the transmission points 114 are associated with the surfaces of the obstacle 104. One or more of the critical points 116 may be located distal to the obstacle 104, within the obstacle, or even proximal to the obstacle.

The transmission points 114 may be used for propagating ultrasound energy 102 to the target region 108 because the transmission points may be efficient at transmitting ultrasound energy to the one or more target points 112, 113. In contrast, the critical points 116 may be avoided when propagating ultrasound energy 102 to the target region 108. The critical points may be inefficient at transmitting ultrasound energy to the one or more target points 112, 113 or may cause undesirable effects, such as heating. In other words, the transmission points 114 may be associated with higher focusing gain compared to focusing gain for the critical points 116. In general, ultrasound energy 102 may be maximized at the target points 112, 113 and minimized at the critical points 116 using various optimization techniques described herein. Although the transmission points 114 and the critical points 116 may be defined as on or inside the volume of the obstacle 104, these control points may also be positioned proximal or distal to the obstacle.

In some embodiments, focused image data may be used to evaluate efficient frequency bands for transmitting ultrasound energy through the selected transmission points 114. For example, transmission points 114 may be associated with are associated with higher focusing gain compared to focusing gains for the critical points 116.

An efficient frequency band for a selected set of transmission points 114 and/or critical points 116 may be determined based on the focusing gain at target points 112, 113 and critical points 116. When a high focusing gain is present at the target points 112, 113 and a low focusing gain is present at the critical points 116 for a particular frequency band, that frequency band may be deemed an efficient frequency band.

Excitation waveforms may be synthesized for the delivery of refocused ultrasound energy to the target points based on the efficient frequency bands and their associated transmission points 114. In particular, when the excitation waveforms are synthesized (for example, for imaging or therapy), the efficient frequency bands may be present in the spectral content of the excitation waveforms (at least a higher amplitudes) instead of inefficient frequencies. Inefficient frequencies may result in lower focusing gains at the target points or higher focusing gains at the critical points.

The initial image data may also be used to define one or more virtual arrays 118, 120. The virtual arrays 118, 120 may represent points along paths of beams of ultrasound energy 102 emitted from the array 22 into the tissue volume 110. For example, the first virtual array 118 may include control points 122, which represent the intersection of certain beams of ultrasound energy 102 at or near a distal surface of the obstacle 104. However, the control points 122 need not be limited to the distal surface of the obstacle 104 (for example, may be positioned in the brain tissue). The second virtual array 120 may include control points 114, which as illustrated, also correspond to transmission points 114. However, control points and transmission points need not correspond to one another and may be different. In some cases, the control points 122 for the first and second virtual arrays 118, 120 are disposed on opposite sides of the obstacle.

Various imaging modes may provide unfocused or focused wavefronts within an imaging field of view. For example, SA and cSA provide unfocused wavefronts, whereas STF, MTF, and cMTF provide focused wavefronts. Focused wavefronts may allow for targeting one or more points within the imaging field of view. Among imaging modes providing focused wavefronts, some modes may allow for focusing on a single point, or one point, within the field of view, such as STF. Other modes may allow for focusing on multiple points, or two or more points, such as MTF or cMTF. One example of synthesizing wavefronts for multiple focus points, for example, using a single frequency, is described in Ebbini and Cain, "Multiple-focus ultrasound phased array pattern synthesis—Optimal driving signal distributions for hyperthermia," IEEE TRANSACTIONS ON ULTRASONICS FERROELECTRICS AND FREQUENCY CONTROL, vol. 36, no. 5, pp. 540-548, (September 1989).

Throughout the disclosure, many references to SA can be generalized to include cSA. Similarly, many references to STF can be generalized to include MTF and cMTF.

The application of ultrasound energy, such as tFUS, may be synchronized with STF imaging, which may benefit from refocusing algorithms described herein. The imaging transmit beam may utilize the same delay pattern used for the therapy beam, but use sub-microsecond waveforms at a diagnostic level of energy. This may allow for the formation of images that characterize the interactions between the tissue volume and one or more iterations of therapy beams at sub-therapeutic or nondestructive levels. Any obstacles can be identified and accounted for in optimal refocusing. STF imaging may be much faster than SA imaging while maintaining a high level of sensitivity and specificity to tissue changes at the target point. The high transmit focusing gain may allow for using STF in nonlinear imaging applications that provide high contrast imaging of HIFU-induced lesions and ultrasound thermography, as described respectively in E. S. Ebbini, H. Yao, and A. Shrestha, "Dual-mode ultrasound arrays for image-guided surgery," Ultrasonic Imaging, 28:65-82, April 2006 and Alyona Haritonova, Dalong Liu, and Emad S Ebbini, "In Vivo application and localization of transcranial focused ultrasound using dual-mode ultrasound arrays. 62:2031-2042, 2015," which are all incorporated entirely herein by reference. In these applications, the use of an imaging beam with the same size as the therapeutic HIFU beam may maximize the sensitivity to tissue changes (e.g. harmonic generation or temperature change) within the focal region of the therapy beam.

Refocused image data may be beneficial even for ultrasound energy guided by other types of imaging. For example, the benefits of using refocused ultrasound energy in guidance and monitoring may be beneficial in magnetic resonance (MR)-guided tFUS. In particular, refocused ultrasound energy may be useful in temperature imaging where STF frame rates may allow for temperature feedback with millisecond resolution. This quick temporal resolution may facilitate avoiding skull or scalp heating when forming lesions using short tFUS exposures (for example, in the order of 1 second). Conventional MR guidance systems may not provide this level of temporal resolution.

Beams of ultrasound energy 102 may be characterized by a wavefront. A desired wavefront can be specified by a finite number of control points, each related to a distinct waveform (e.g. chirp) detectable in pulse-echo data. When the specified waveforms are orthogonal within the bandwidth of the transducer array 22, the wideband wavefront may be free from interference patterns at points other than the intended control points. In therapeutic applications, interference patterns may lead to hot spots away from the intended targets.

Various imaging modes may provide coded wavefronts, such as cSA and cMTF. In general, coded wavefronts utilize arbitrary waveform generation to transmit coded wavefronts. The coded wavefronts may allow for focusing on (for example, targeting or interrogation) multiple points of interest within the field of view simultaneously or concurrently or may allow for using multiple codes to target the same points. Targeting multiple points, such as target points 112, 113 may allow for tracking fast moving targets, such as cardiac ablation, cardiac pacing, etc. Targeting the same points may allow for improving the robustness of refocusing.

In other words, multiple points may be targeted in one delivery of ultrasound energy or ultrasound energy pulse. The use of cMTF in pulse-echo mode may be used to transmit or receive different waveforms, which may be orthogonal waveforms, such as prolate spheroidal wave functions (PSWFs), from discrete focal points.

Coded wavefronts may be generated by multi-modal coded excitation imaging algorithms for DMUAs to enhance imaging resolution and signal to noise in a region of interest together with improving the frame rates. Further, multi-modal coded excitation may be beneficial for improving the focusing gain at the desired target location (or locations when multiple-focusing is used). A broadband waveform can be synthesized at the target location where its frequency components add up coherently within a pillbox (for example, target) with dimensions determined by the coherence length (inverse of the bandwidth) and shaped by the focusing aperture. Outside this volume, wavelets from individual elements may add up almost incoherently when the elements are sufficiently separated in space. This results in array focusing gains much larger than their single-frequency counterparts.

For example, one or more illustrative examples of coded excitation ultrasound which may be used in combination with the imaging method and/or systems described herein are provided in Shen et al., "A New Coded-Excitation Ultrasound Imaging System—Part I: Basic Principles," *IEEE Transactions on Ultrasonics, Ferroelectrics, and Frequency Control*, vol. 43, no. 1, pp. 131-140, January 1996); Shen et al., "A New Coded-Excitation Ultrasound Imaging System—Part II: Operator Design," *IEEE Transactions on Ultrasonics, Ferroelectrics, and Frequency Control*, vol. 43, no. 1, pp. 141-148, January 1996); and Shen et al., "Filter-Based Coded-Excitation System for High-Speed Ultrasound Imaging," IEEE Transactions on Medical Imaging, vol. 17, no. 6, pp. 923-934, December 1998), which are all entirely incorporated herein by reference.

The different waveforms used in coded wavefronts may be orthogonal, but may not need to be completely orthogonal. In general, wavefronts that have an acceptable 2D or 3D spatial correlation function may be synthesized for use in pulse-echo imaging, and spatial-temporal filters may be used to decorrelate the received waveforms (for example, using beamforming). Beamforming or spatial-temporal filtering may be used to provide directional signal transmission or reception. Elements in the array 22 may be combined such that some signals experience constructive interference and other signals experience destructive interference. Beamforming may be applied to transmitted signals (pre-beamforming), received signals (post-beamforming), or both to achieve spatial selectivity. The ability to improve spatial selectivity may be described as the directivity of the array 22, which measures the power density the array radiates in the direction of its strongest emission versus an omnidirectional array using the same total power.

Ultrasound energy may be delivered from the array 22 at one or more frequency bands or discrete frequencies. An excitation vector may be used to describe the phases and amplitudes of the driving signals to each of the elements of the array 22 at a particular frequency band or discrete frequency. A multiband excitation waveform may be synthesized from one or more excitation vectors. The excitation waveform may be used to describe the phases and amplitudes of multiple frequency bands or multiple discrete frequencies. Excitation waveforms may be used to define transmit pulses and may be synthesized as a sum of modulated sinusoids with well-defined time-bandwidth products.

In some embodiments, the bandwidth of an individual frequency band may be in the range from about 100 kHz to about 200 kHz. The system bandwidth may contain between about 10 and about 20 frequency bands, or discrete frequencies, within the bandwidth of the transducer array 22, which may be used to transmit or receive ultrasound energy.

A potential problem with using a transducer array 22 for imaging or therapy is that the ultrasound energy may insonate non-target locations within the tissue volume. For example, it may be desirable to use ultrasound energy to produce a response at one or more target points while avoiding undesirable responses at one or more other control points, such as the critical points. Thus, the goal of using the transducer array 22 for imaging or therapy may be described as maximizing the response at target points while minimizing the response at critical points. In general, FUS may be utilized to increase responses at target points while reducing responses at critical points.

The first step to utilizing FUS to produce desired responses within the tissue volume may be to model the transducer array 22, the tissue volume, and the desired responses at various locations within the tissue volume. The transducer array 22 may be described as having N elements n, which may operate at one or more frequencies. The array 22 may be configured to focus ultrasound energy at M control points m, which may include the target points (typically, M<N). In the case of using narrowband ultrasound energy, assuming a homogeneous half space as a propagation medium, the complex pressure at the mth control point due to the array 22 may be given by Equation 1, where $u_n$ is the complex particle velocity at the surface of element n, $S_n$ is the surface of the element n, and c, $\rho$, $\lambda$ denote the speed of sound, density, and the wavelength, respectively, and $\omega_0$ denotes the operating frequency used for the array 22. The vector form of Equation 1 may be represented by Equation 2.

$$p(\vec{r}_m) = \frac{j\rho c}{\lambda} \sum_{n=1}^{N} u_n \int_{S'_n} \frac{e^{-jk|\vec{r}_m - \vec{r}'_n|}}{|\vec{r}_m - \vec{r}'_n|} dS'_n = \sum_{n=1}^{N} u_n h_n(\vec{r}_m), \quad (1)$$

$$p = Hu, \quad (2)$$

The entries of the propagation operator, H, may account for the effects of propagation and diffraction from the surface of element n to the control point m. An example of a formula to describe the propagation operator H is provided in Equation 3. This narrowband model equation may be valid even for inhomogeneous propagation medium, as long as the medium satisfies the reciprocity property. In practice, the elements of H can be computed, measured, or estimated.

$$H(m,n) = \frac{j\rho c}{\lambda} \int_{S'_n} \frac{e^{-jk|\vec{r}_m - \vec{r}'_n|}}{|\vec{r}_m - \vec{r}'_n|} dS'_n. \quad (3)$$

An inverse solution for Equation 2 can be found based on an appropriate optimality criterion to find excitation vector $u_{opt}$ in terms of the specified complex pressure values p at $\{\vec{r}_m\}_{m=1}^{M}$. One example of the inverse solution is Equation 4, which is in the form of a weighted minimum-norm least squares (MNLS) solution where $(\cdot)^H$ is the Hermitian transpose, W is an invertible weighting matrix and $\gamma$ is a regularization parameter. The general solution of Equation 4 may be used in a variety of ways to regularize the solution to the optimization problem, for example, to provide a method to avoid direct exposure to discontinuous obstacles (for example, the ribs in transthoracic refocusing) or to minimize exposure to continuous obstacles (for example, the skull in transcranial refocusing).

$$u_{opt} = W^{-1}H^H(HW^{-1}H^H + \gamma I)^{-1}p \quad (4)$$

Figure 2C:
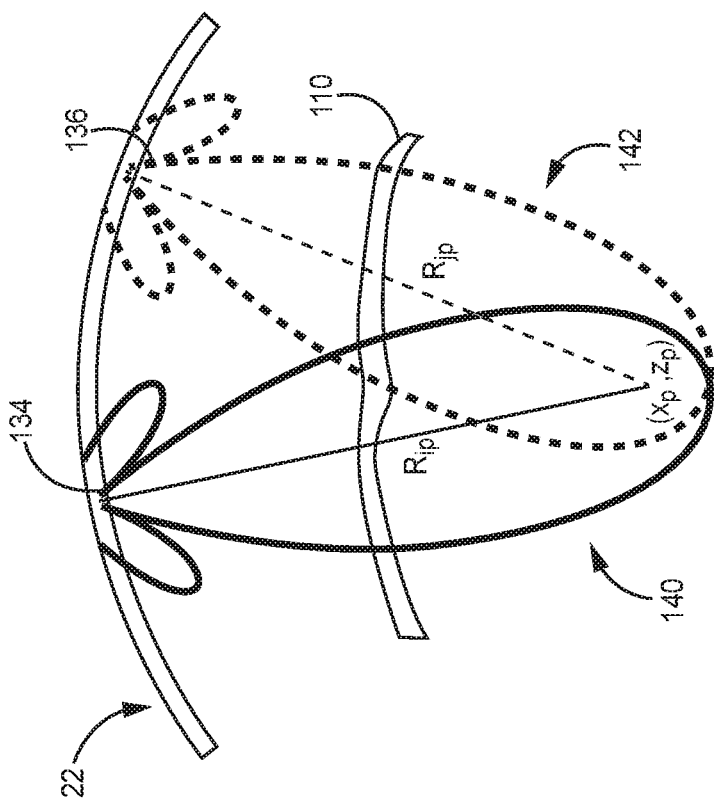
FIGS. 2B and 2C are an isometric view and a top-down view, respectively, of an ultrasound imaging or therapy system used with a patient.
Figure 2B:
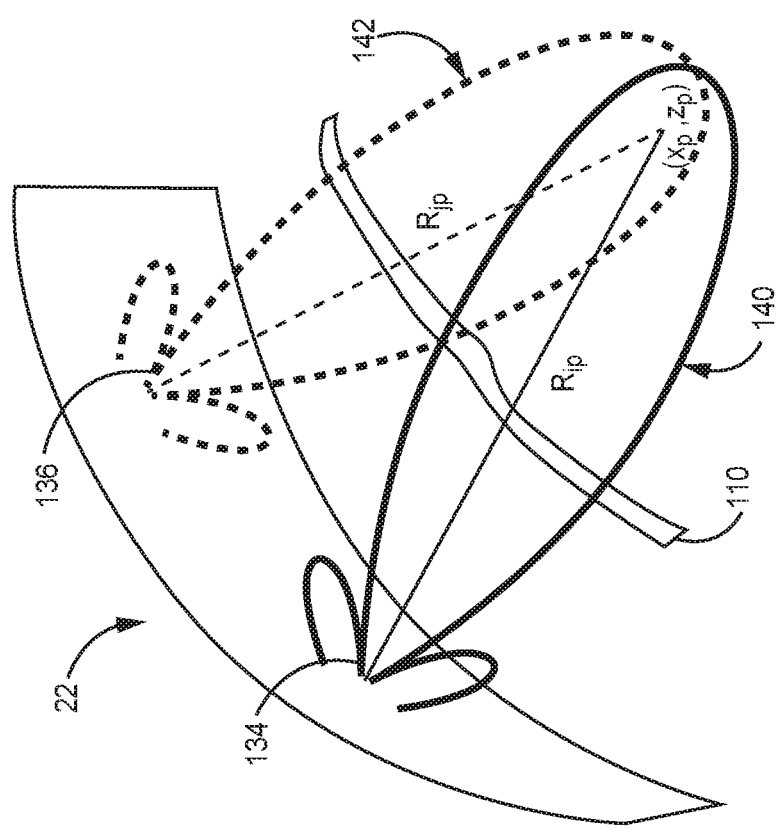

FIGS. 2B and 2C show an isometric view and a top-down view illustrating an example of a transducer elements in the form of an array, or transducer array 22, for use in transcranial focusing or refocusing. The directivity patterns 140, 142 of two elements 134, 136 are shown together with the geometric distances R to a target point P at $(x_p, z_p)$. Due to the presence of the skull, the echoes from this point may arrive at the receiving element with envelope distortion, as well as delay errors, compared to the geometric delays in a homogeneous medium. The location of the elements 134, 136, the target point P, and the geometric distances therebetween R are used to define values of the initial propagation operators $H_T^{(0)}$ (to the target point P) and $H_C^{(0)}$ (to any critical points) assuming a homogeneous medium.

An optimal value of the array excitation vector $u_{opt}$ may be found for the current values of $H_T^{(0)}$ and $H_C^{(0)}$ using Equation 5. This optimal solution uses weighting matrix $W_C$, to produce an excitation vector $u_{opt}$ that may minimize incident power at any critical points associated with the operator $H_C$ while maintaining or increasing the exposure level at any target point associated with $H_T$. For reference, Equation 5 was further described in Y. Y. Botros, J. L. Volakis, P. VanBaren, and E. S. Ebbini, "A hybrid computational model for ultrasound phased-array heating in presence of strongly scattering obstacles," IEEE Transactions on Biomedical Engineering, vol. 44, no. 11, pp. 1039-1050, November 1997.

$$u_{opt}^{(i)} = W_C^{-1} H_T^H (H_T W_C^{-1} H_T^H)^\dagger p_T \quad (5)$$

Transmit focus imaging, such as STF, MTF, or cMTF, may utilize the excitation vector $u_{opt}$ to synthesize optimized excitation waveforms for driving the transducer elements of the array 22 that take into account the one or more target points and one or more critical points. The optimized excitation waveforms may be used to deliver ultrasound energy and generate focused image data of the treatment region, or target region. The focused image data may include information associated with one or more target points, one or more critical points, or one or more transmission points.

Received channel data may be used to provide the focused image data. A focused data matrix $X_m$ for each control point may be formed from the channel data and may also be used as the focused image data. One examples of a focused data matrix $X_m$ is a narrowband focused data matrix $X_m$ formed using a Hilbert transform as shown in Equation 6. The focused data matrix $X_m$ may include L samples for N elements n to provide an L×N matrix. In some embodiments, the focused image data may include measurements in a plurality of different frequency bands using the ultrasound transducer elements (see, for example, Equation 7).

$$X_m(:,n) = \mathcal{H}\left\{ RF_n\left(\left\lceil\frac{2*R_{m,n}^{min}*F_s}{c}\right\rceil : \left\lceil\frac{2*R_{m,n}^{max}*F_s}{c}\right\rceil\right)\right\} \quad (6)$$

The focused image data may be used to evaluate tissue responses due to delivering ultrasound energy based on the optimized excitation waveforms. For example, focusing gains may be determined based on the focused image data. The focusing gains may include at least a target focusing gain associated with one of the target points and a critical focusing gain associated with one of the critical points. The response may be characterized by echogenicity, localized heating, localized cavitation, or tissue displacement.

Evaluating the focusing gains may include a comparison to various thresholds. For example, in response to determining that both a target focusing gain is no less than a minimum threshold and that a critical focusing gain is no greater than a maximum threshold, ultrasound energy based may be delivered to the tissue volume for imaging or therapy based on the optimized excitation waveforms.

On the other hand, in response to determining that either the target focusing gain is less than the minimum threshold or that the critical focusing gain is greater than the maximum threshold, an iteration of the optimized excitation waveforms may be synthesized by updating the propagation operators $H_T^{(i)}$ and $H_C^{(i)}$ based on the focused image data. Synthesizing an iteration of the excitation waveforms may be configured to increase target focusing gain associated with the one or more target points and reduce critical focusing gain associated with the one or more critical points. For example, the focused data matrix $X_m$ may be used to update propagation operators $H_T^{(i)}$ and $H_C^{(i)}$. Further optimized excitation waveforms may be synthesized based on the updated propagation operators $H_T^{(i)}$ and $H_C^{(i)}$ to generate refocused image data. In some cases, focusing gain may be evaluated based on refocused image data, for example, if the focusing gains do not meet the evaluation criteria and further iterations of the excitation waveforms are synthesized.

As discussed herein in more detail, the algorithms described in the present disclosure may differ from the geometric refocusing algorithm described in J R Ballard, A J Casper, Y Wan, and E S Ebbini, "Adaptive Transthoracic Refocusing of Dual-Mode Ultrasound Arrays," IEEE TRANSACTIONS ON BIOMEDICAL ENGINEERING, 57(1):93-102, January 2010, in that the present refocusing algorithms may use channel data, or particularly, a channel data matrix, to apply aberration correction on transmit. The present disclosure may also differ from the method described in Claire Prada, Sebastien Manneville, Dimitri Spoliansky, and Mathias Fink, "Decomposition of the time reversal operator: Detection and selective focusing on two scatterers," J. Acoust. Soc. Am, 99:2067-2076, 1996, in that the present refocusing algorithms may employ STF imaging, may utilize the refocused beams to generate forming STF images for testing the improvement in terms of the focusing gain at the target and critical points, may allow for minimizing exposure to critical points, and may be suitable for use with tissue volumes without dominant scatterers (for example, in brain tissue). The present disclosure may further differ from the technique described in G. F. Pinton, J. F. Aubry, and M. Tanter, "Direct phase projection and transcranial focusing of ultrasound for brain therapy," IEEE Transactions on Ultrasonics, Ferroelectrics, and Frequency Control, 59(6):1149-1159, June 2012, in that the present refocusing algorithms utilize the DMUA imaging guidance and feedback and may utilize wideband optimization.

Figure 3:
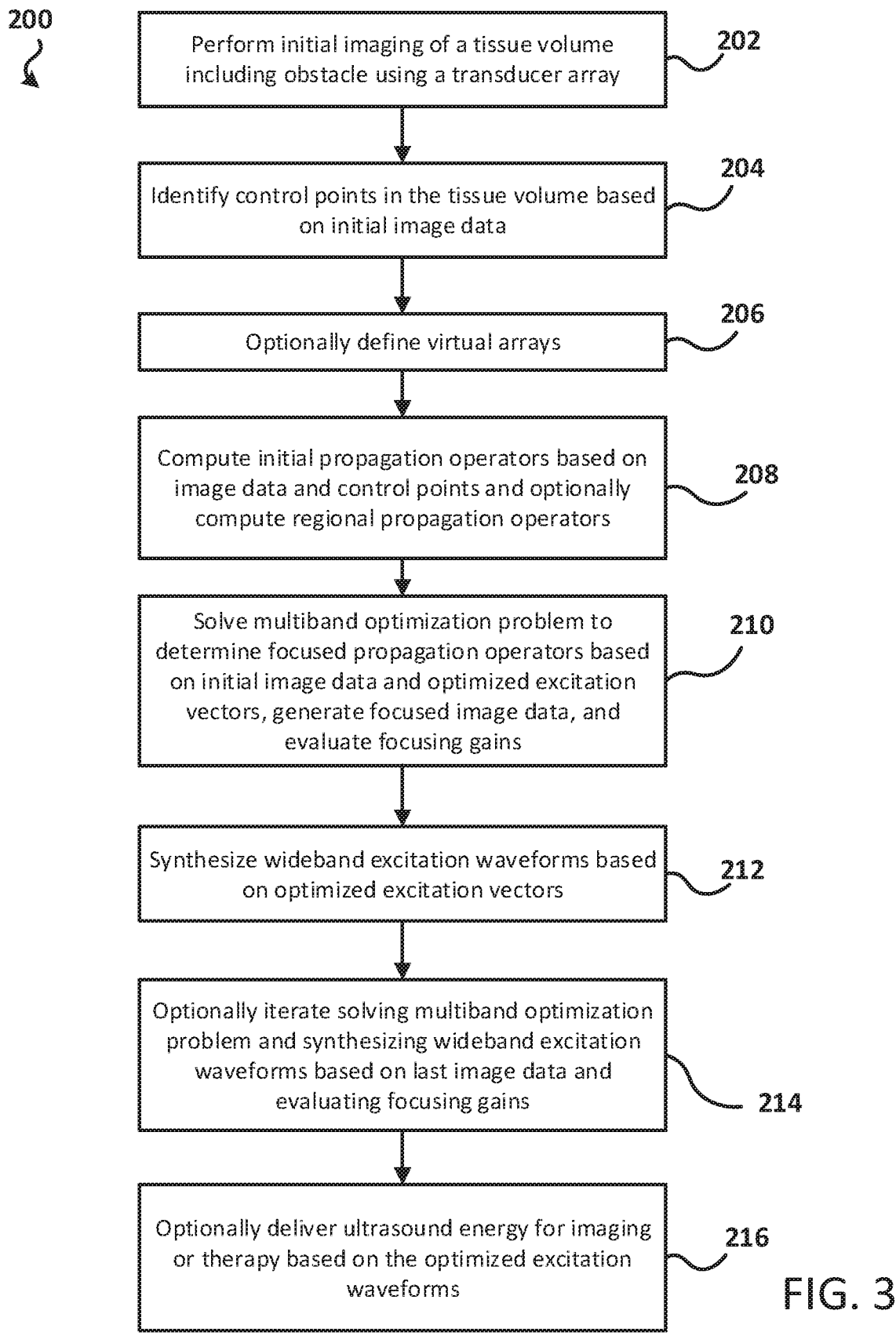
FIG. 3 is a flowchart of a method for refocusing ultrasound.

FIG. 3 shows one example of a method 200 for providing a refocused wavefront of ultrasound energy to the tissue volume, particularly in the presence of an unavoidable, ultrasound-distorting obstacle (such as the skull).

In process 202, initial imaging of the tissue volume including the obstacle may be performed using a transducer array, such as a DMUT or DMUA. Initial imaging may utilize a wide field of view to capture the tissue volume. Unfocused imaging may be used to generate the initial image data. Non-limiting examples of unfocused imaging to gather initial image data include SA or cSA imaging. Initial imaging may be performed using a narrowband or wideband wavefront. A narrowband wavefront may include waveforms in one narrow frequency band or at a discrete frequency. A wideband wavefront may include waveforms in a plurality of frequencies. In some embodiments, each waveform may comprise a plurality of frequencies.

Waveforms for wideband imaging may occupy some or all the bandwidth of the DMUA or DMUT. In some embodiments, wideband imaging may occupy most of the bandwidth. Preferably, the full available bandwidth of the transducer array may be used. Some element waveforms may have reduced energy in certain frequency bands if those bands contribute more at the critical point(s) than at the target point(s). In some embodiments, the fractional bandwidth (for example, the bandwidth of the device divided by the center frequency) may about 60 percent.

Figure 4:
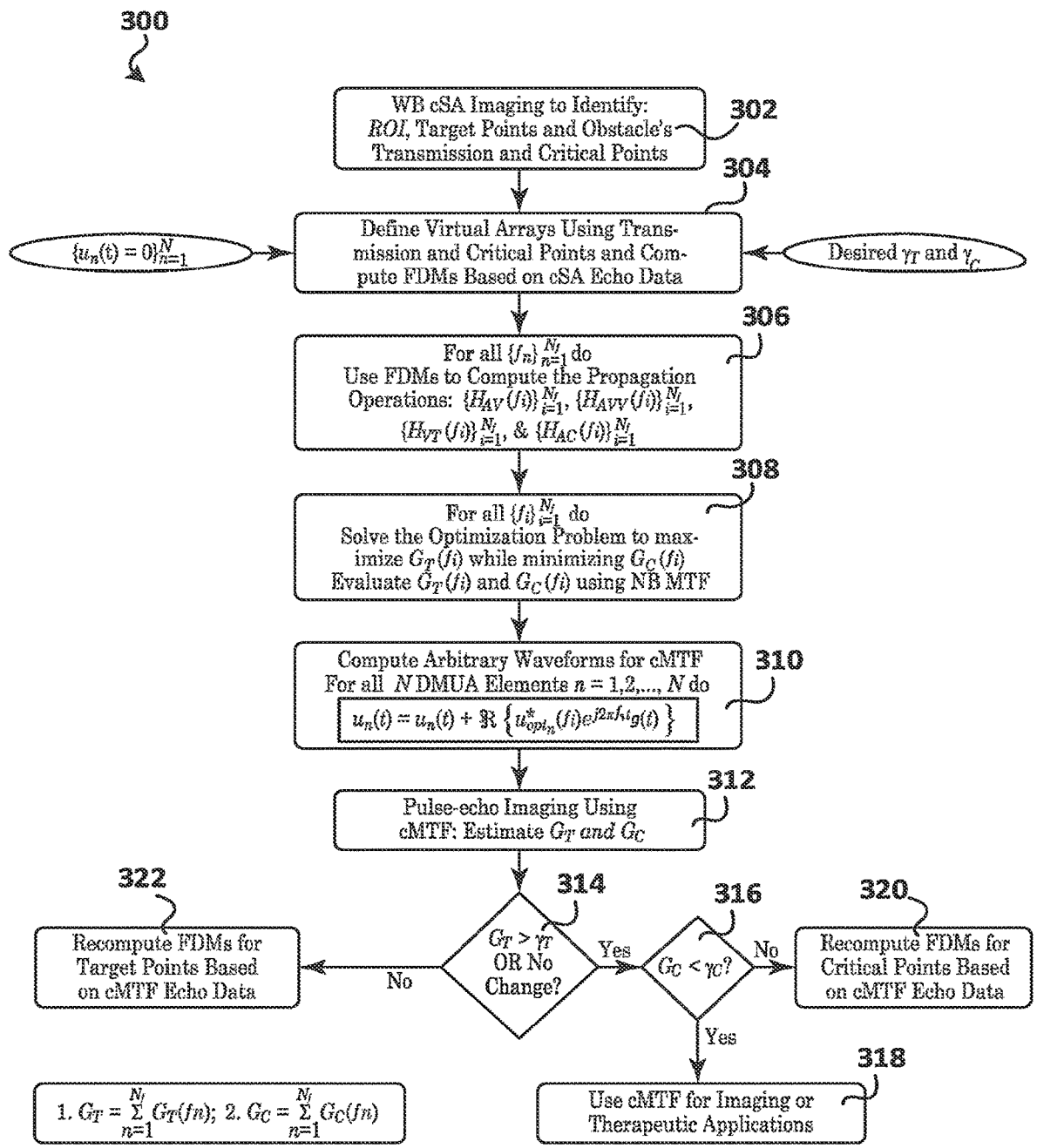
FIG. 4 is a flowchart of another method for refocusing ultrasound.
Figure 10:
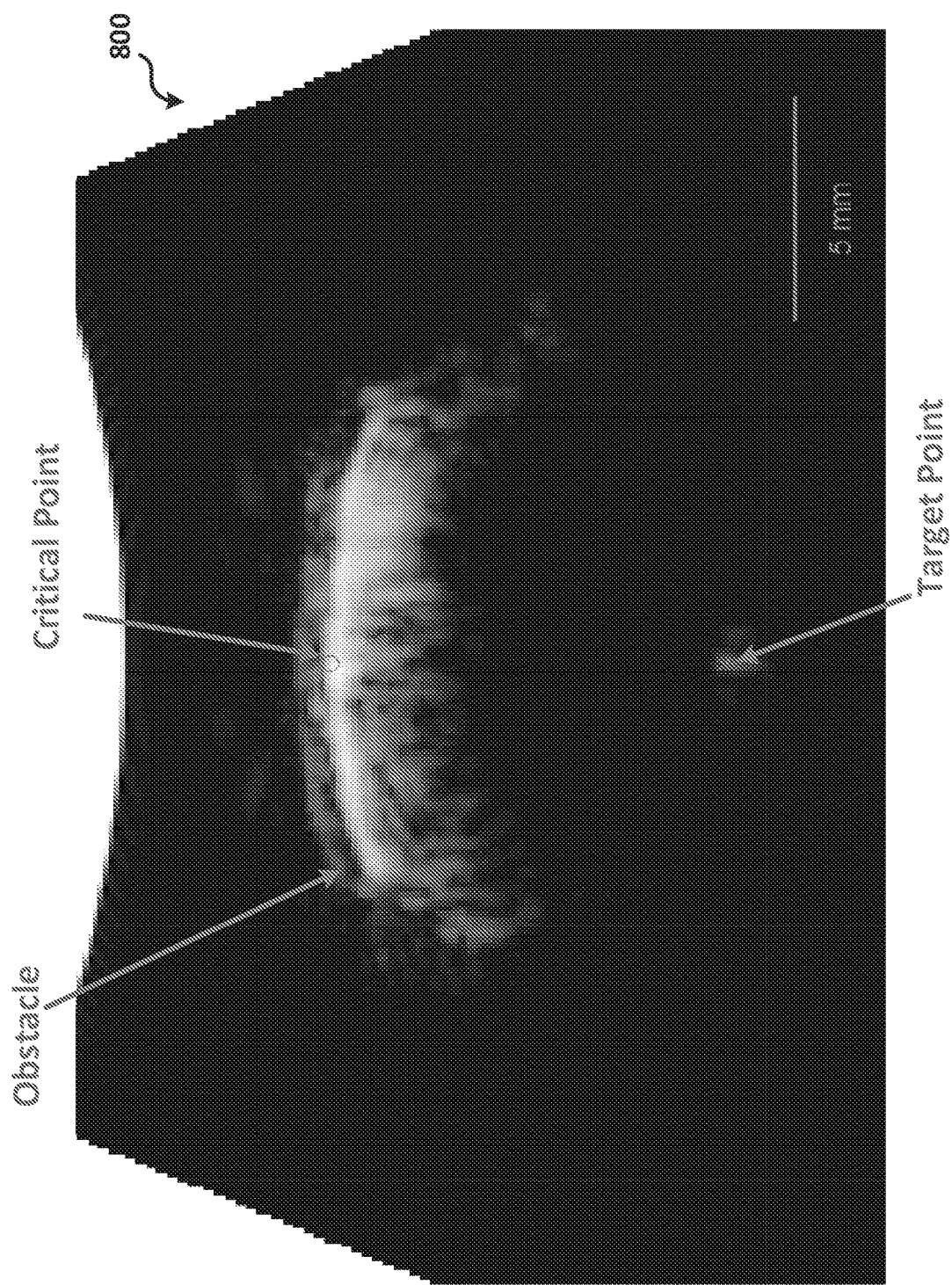
FIG. 10 is an ultrasound image generated by synthetic aperture imaging of an in vitro system.

Examples of process 202 may relate to other processes or structures described herein. In FIG. 4, initial image data is generated in process 302 using wideband cSA imaging. In FIG. 8A, algorithm 700 initializes using SA Imaging. In FIG. 8B, algorithm 701 initializes using SA imaging. In FIG. 10, SA image 800 may be formed form initial image data.

Figure 14:
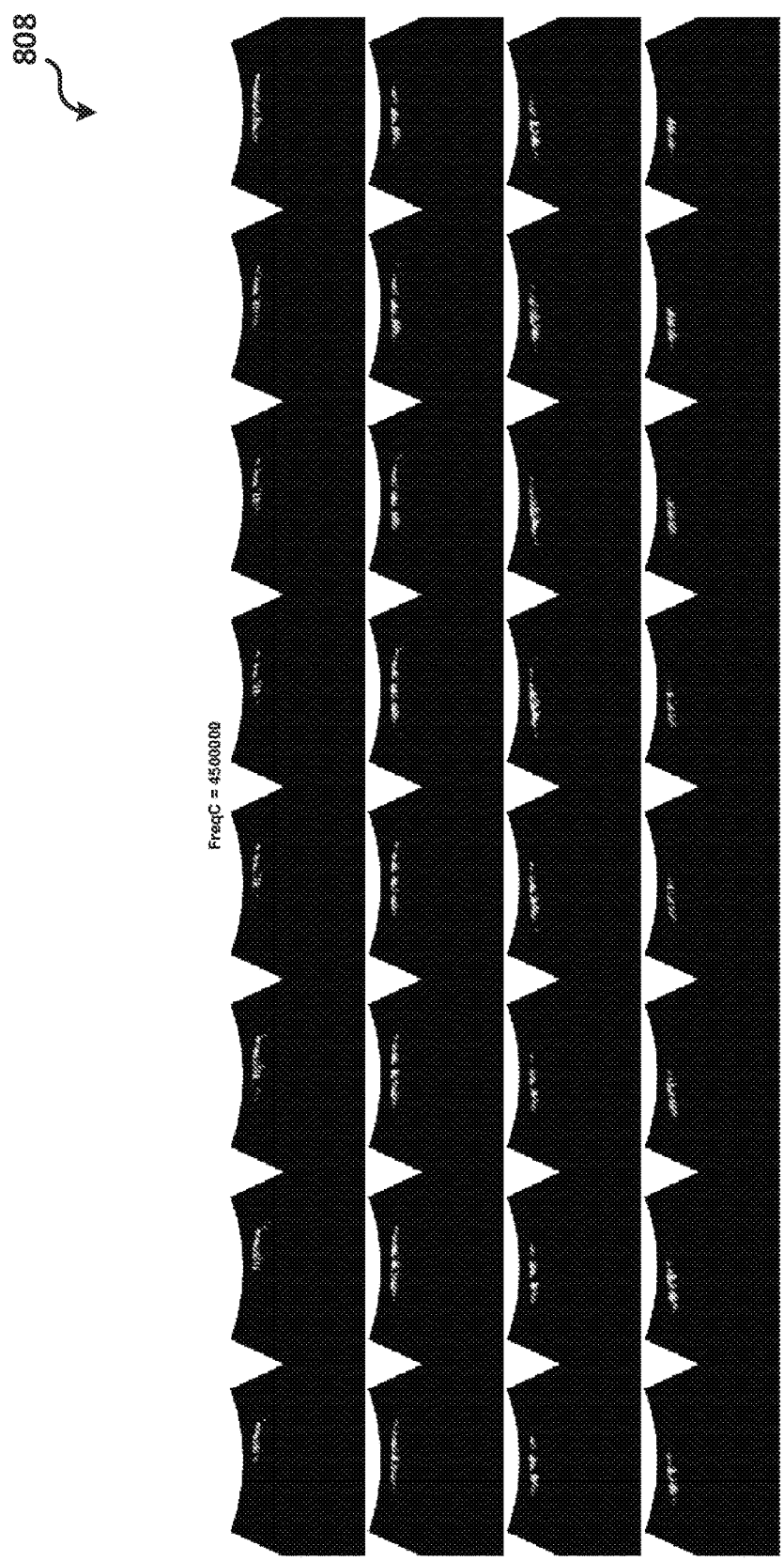
FIG. 14 is a montage of ultrasound images generated from single-element transmissions to identify transmission points through the obstacle (the image data corresponding to the ultrasound image of FIG. 10).

In process 204, the initial image data may be used to identify control points in the tissue volume based on the initial image data. Non-limiting examples of control points include target points, transmission points related to the obstacle, and critical points related to the obstacle. The transmission points and critical points may be selected points within the path of ultrasound beams from each of the DMUTs that also pass through the obstacle. In other words, the transmission points and critical points may be selected from the point spread function of the DMUA at one or more distances from the DMUA. In some embodiments, the critical points may be selected first, and the transmission points may be automatically selected from the remaining points on the proximal surface of the obstacle in the path of the beam. These points can be identified from SA (or cSA) data by forming images from single-element transmission as shown in image 808 (FIG. 14). For example, all points not deemed a critical point may be treated as a transmission point.

Examples of process 204 may relate to other processes or structures described herein. In FIG. 4, control points are identified in process 302. In FIG. 8A, one or more target points and one or more critical points are identified based on initial SA imaging. In FIG. 8B, one or more target points are identified, as well as the obstacle's transmission and critical points. The transmission points may be candidate transmission points, which may be modified upon receive additional image data in algorithm 701. In FIG. 10, an obstacle, a critical point, and a target point are identified in the SA image.

In process 206, one or more virtual arrays may be defined. The virtual arrays may be defined by one or more virtual array points. In some embodiments, the virtual array points may be selected from one or more transmission points. In some embodiments, at least two virtual arrays may be defined. In some embodiments, two virtual arrays may be used in an application that defines at least one target point, a distal obstacle surface, a proximal obstacle surface, and a DMUA surface. Each virtual array may correspond to one of the opposing surfaces of the obstacle. For example, one virtual array may correspond to a proximal side of a skull, and the other virtual array may correspond to a distal side of the skull.

One or more regions may be defined based on at least one of the array, the tissue volume, the obstacle, and the control points. Non-limiting examples of regions include a region of interest (which may be coextensive with the tissue volume), a target region (which may include target points), a tissue or distal region (generally between the target points and the obstacle), an obstacle (a region defined generally between two surfaces of the obstacle), and a non-tissue or proximal region (generally between the obstacle and the DMUA).

Examples of process 206 may relate to other processes or structures described herein. In FIG. 4, virtual arrays are defined in process 306 based on the transmission points and critical points. In FIG. 14, various SA images 808 are used to define virtual array points.

In process 208, initial propagation operators may be computed based on image data and control points and, if applicable, regional propagation operators may be computed. A propagation operator may correspond to one control point within the tissue volume. The propagation operator may also correspond to only one DMUT in the array. An example of the propagation operator is provided by Equation 3. In general, the propagation operator may describe the transformation of ultrasound energy that is delivered by the DMUT and arrives at the control point.

In some embodiments, the initial image data may be generated from raw channel data. The channel data may be filtered, for example, spatially filtered. A focused data matrix may be generated from the channel data, for example, according to Equation 6. The focused data matrix may represent channel data that has been aligned and truncated. The focused data matrix may be used to compute the initial propagation operators using, for example, SVD.

Regional propagation operators may be computed based on the transducer array, the one or more virtual arrays, the one or more target points, or the initial propagation operator. The initial propagation operator may define a full propagation operator (from the DMUA to a target point or critical point). A regional propagation operator may characterize the transmission of ultrasound energy through a corresponding region. For example, a first propagation operator may be computed between a target point and points of the distal virtual array. A second propagation operator may be computed between points of the distal virtual array and points of the proximal virtual array. Then, a third propagation operator may be computed between points of the proximal virtual array and the DMUTs. The regional propagation operators may be cascaded (for example, in matrix form) to provide the full propagation operator (from the DMUA to a target point or critical point).

Figure 5:
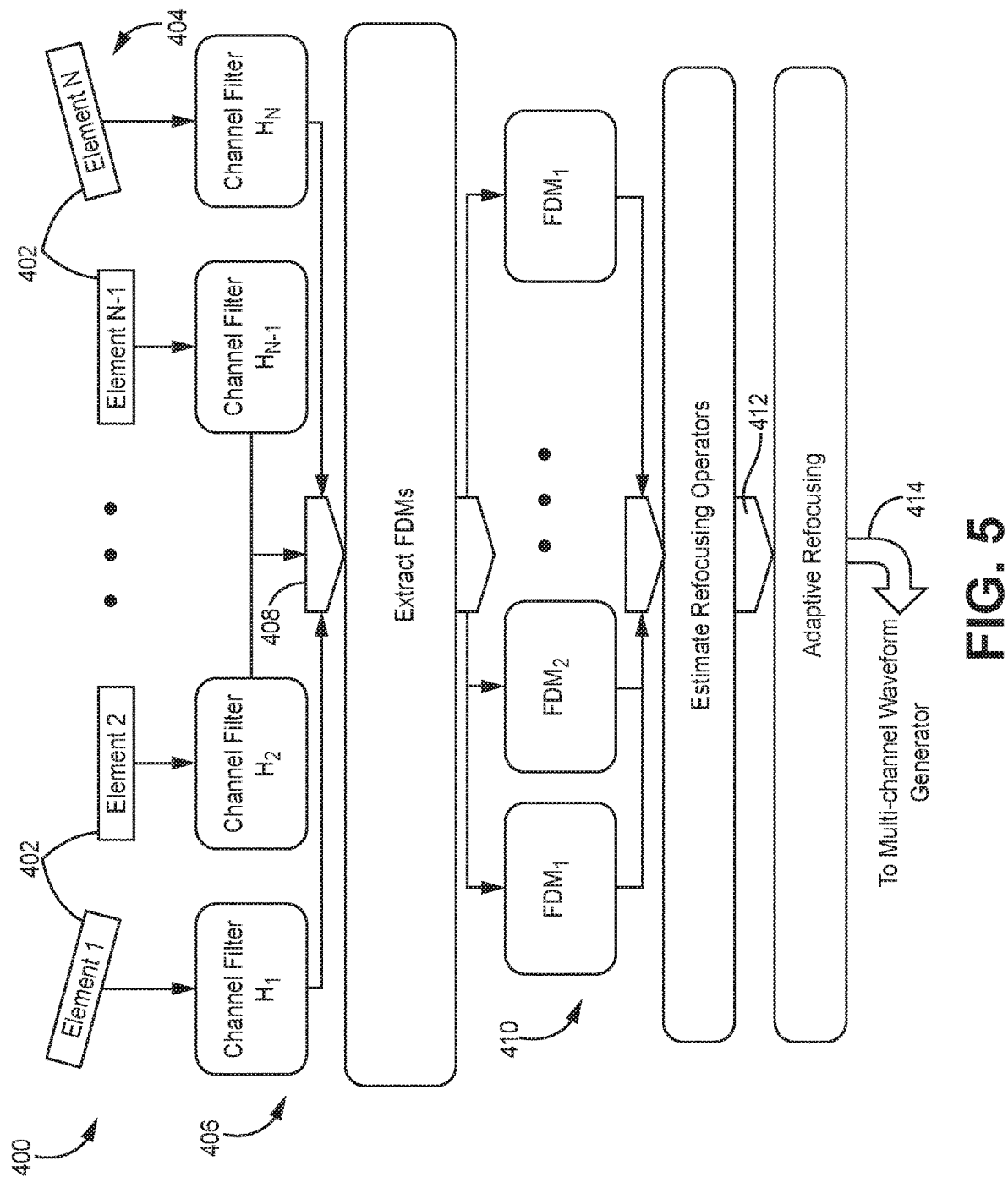
FIG. 5 is a block diagram of a system capable of multi-modal imaging for refocusing ultrasound.
Figure 6:
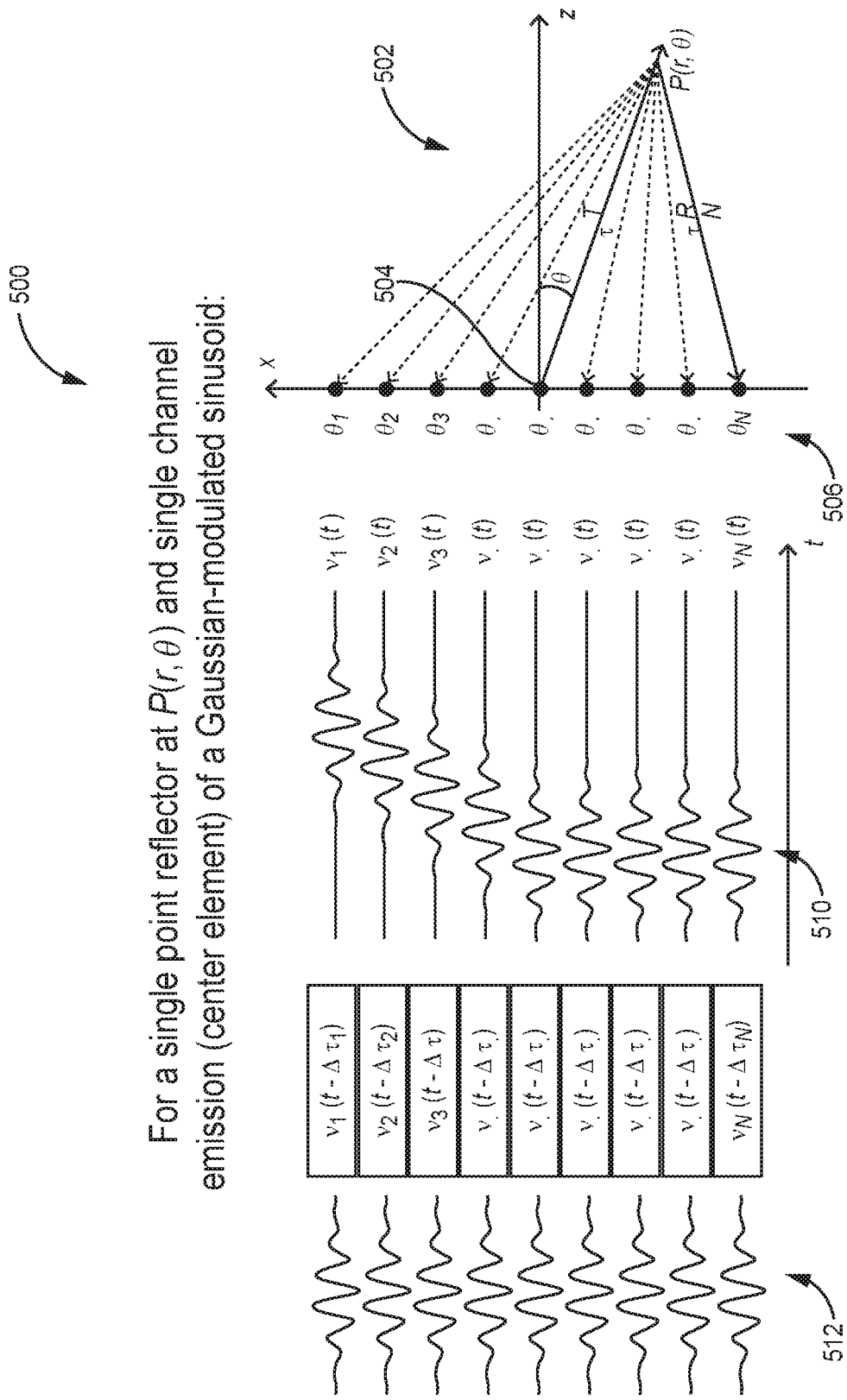
FIG. 6 is a plot of simulated pulse-echo data received by the ultrasound imaging or therapy system.

Examples of process 208 may relate to other processes or structures described herein. In FIG. 4, focused data matrices are computed based on cSA echo data in process 304. Regional propagation operators may be computed based on the focused data matrices in process 306. In FIG. 5, focused data matrices 410 are generated based on channel data 408 that has been filtered by a filter bank, or bank of channel filters 406. The propagation operators 412, which may include regional propagation operators, may be generated based on the focused data matrices 410. In FIG. 6, the waveforms shown in graph 512 in a focused data matrix may be generated from waveforms in channel data shown in graph 510. In FIG. 8A, initial propagation operators may be determined in algorithm 700 after initializing SA imaging. In FIG. 8B, regional propagation operators may be computed in algorithm 701, for example, in lines 3 and 4, for a plurality of frequencies. In FIG. 9, a focused data matrix is computed according to algorithm 702 using a set of complex narrowband filters.

In process 210, a multiband optimization problem may be solved to determine focused propagation operators based on the image data. One or more optimal excitation vectors to drive the array may be computed based on the focused propagation operators using, for example, Equation 5.

In some embodiments, solving the multiband optimization problem may include solving multiple narrowband optimization problems at different frequencies, for example, at some or all frequency bands within the bandwidth of the transducer array. In particular, the solution to each narrowband optimization problem may produce an optimized excitation vector for a particular frequency band so that each optimal excitation vector corresponds to one frequency.

The solution to the optimization problem may produce an excitation vector that weights away from critical points (by minimizing complex pressures at critical points) and increases or maintains complex pressure at target points.

Once generated, the excitation vectors may identify the most efficient frequencies for transmitting through the obstacle (through the transmission points), for each DMUT, while potentially maximizing ultrasound energy at frequencies that cause desirable effects at the target points and minimizing ultrasound energy at frequencies that cause undesirable effects at the critical points.

Focused image data may be generated using narrowband focused imaging based on the excitation vectors. Non-limiting examples of focused imaging to test multiband optimization include STF or MTF imaging. Preferably, focused imaging to test multiband optimization may use a narrowband wavefront.

Focused image data may be generated from raw multiband channel data due to the focused imaging. In particular, the focused image data may include focused data matrices, for example, according to Equation 7, based on the raw multiband channel data. The focused data matrices may be used to compute focused propagation operators. In some embodiments, the focused propagation operators may be recomputed using regional propagation operators based on the virtual arrays defined in process 206.

Measurements at one or more control points, such as focusing gains at target points and critical points, may be determined based on the focused propagation operators. The focusing gains may be evaluated using a comparison to a threshold focusing gain. For example, focusing gain at the target points may need to meet a minimum threshold, whereas focusing gain at the critical points may need to meet a maximum threshold. However, any suitable manner of evaluating focusing gains may be used.

Virtual arrays and regional propagation operators may provide flexibility in solving the optimization problem of the refocusing algorithm. The virtual arrays may provide a practical solution that may capture the inhomogeneity of the tissue volume (for example, due to the obstacle) in the refocusing problem. Virtual arrays may be used in determining propagation operators between the physical array, the virtual arrays, and one or more control points (for example, target points). The propagation operators may be used in a one-step or multi-step optimization algorithm. In a one-step optimization algorithm, the multiple propagation operators may be cascaded, and one optimization problem may be solved based on the cascaded propagation operators. For example, for two virtual arrays, three propagation operators may be determined based on imaging feedback and using cSA and/or cMTF focused data matrices. In a multi-step optimization algorithm, an optimization may be performed on each of the propagation operators. In other words, the optimization problem may be solved for each region of propagation. For example, when two virtual arrays are defined, the multiband optimization problem may be performed in three steps to optimize for each of the three defined regions between the DMUA and the target points. The synthesis problem can be solved by optimizing the driving waveforms to: 1) the distal virtual array, 2) the proximal virtual array, and 3) the physical array. Both the one-step or multi-step optimization algorithms may give, fundamentally, the same results. The multi-step optimization algorithm may be more useful for regularizing inverse solutions.

Figure 12:
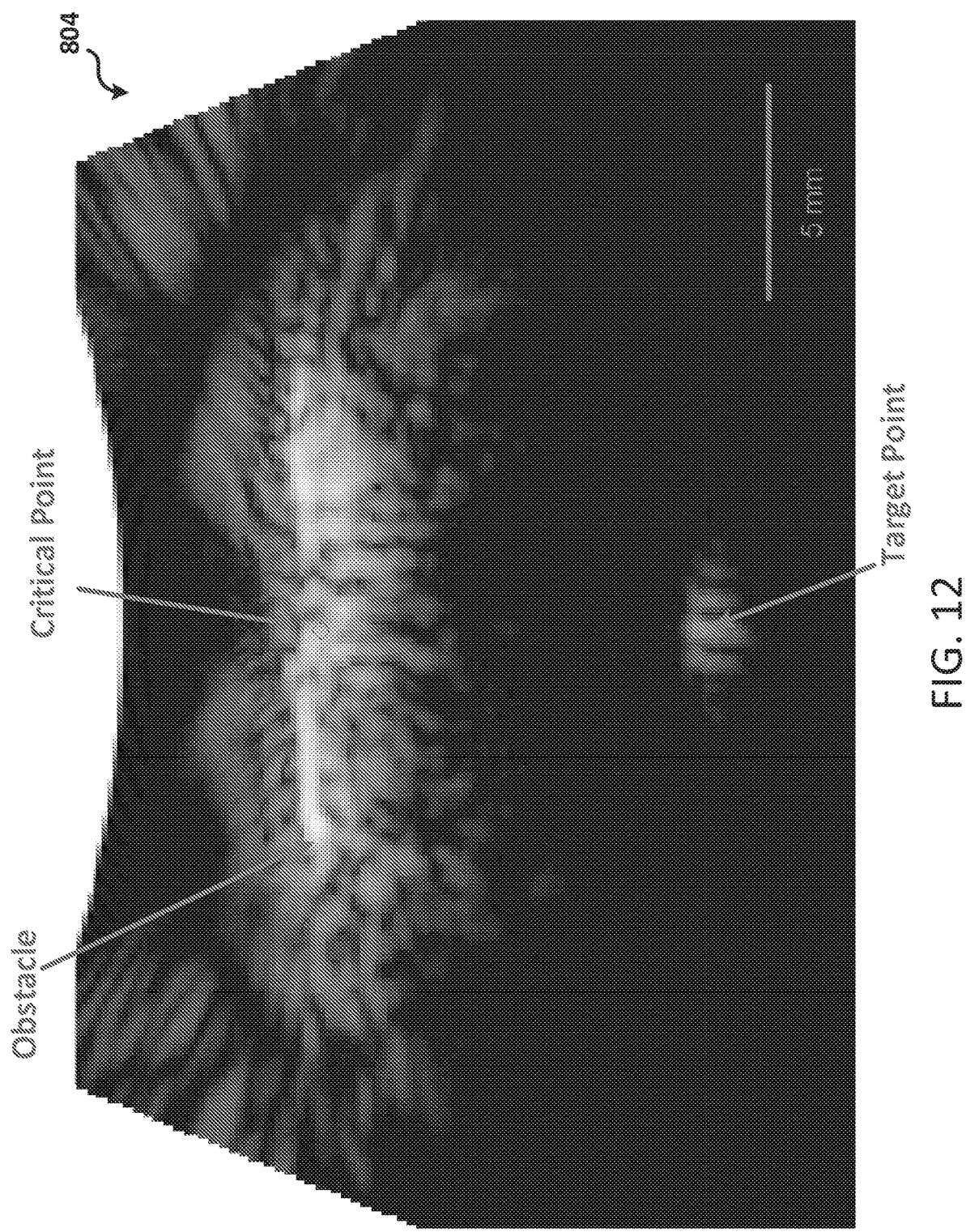
FIG. 12 is a refocused ultrasound image generated by single transmit focus imaging of the system of FIG. 10.

Examples of process 210 may relate to other processes or structures described herein. In FIG. 4, based on the regional propagation operators, the multiband optimization problem may be solved to maximize target point focusing gain and minimize critical focusing gain in process 308. The excitation vector generated by multiband optimization may be used to generate focused image data using narrowband MTF. Channel data may be used to determine focusing gain, which may be evaluated. In FIG. 5, the propagation operators 412 may be used to solve the optimization problem to compute excitation vectors 414. In FIG. 8A, based on the initial propagation operators, the multiband optimization problem may be solved to maximize target point focusing gain and minimize critical focusing gain in algorithm 700. The solution to multiband optimization may be used to generate focused image data using narrowband STF imaging at a plurality of discrete frequencies, for example, at lines 1 and 2. The focused image data may be used to calculate propagation operators for evaluating focusing gains at each of the plurality of frequencies. In FIG. 8B, based on the regional propagation operators, the multiband optimization problem may be solved using three steps to reduce focusing gain at critical points and maintain or increase focusing gain at target points in algorithm 701, for example, in lines 6 to 9. The solution to the multiband optimization may be used to generate focused image data using narrowband MTF imaging a plurality of discrete frequencies, for example, in lines 10 to 12. In FIG. 12, narrowband STF imaging may be performed based on the solution to the multiband optimization problem to produce refocused image 804.

In process 212, wideband excitation waveforms may be synthesized based on the optimized excitation vectors. Each excitation waveform may be defined by various parameters including one or more phases or delays, amplitudes, or spectral content (for example, various frequency bands having center frequencies) to produce desirable focusing gain at one or more points in the tissue volume. In some embodiments, if the focusing gains based on focused image data generated by the excitation vectors meet the evaluation criteria, wideband excitation waveforms may be synthesized for each of the DMUTs. If the focusing gains do not meet the evaluation criteria, solving the multiband optimization problem may be iterated until criteria are met or the focusing gains converge.

Because the optimized excitation vectors identify the most efficient frequencies for each DMUT, the waveforms synthesized for each DMUT may utilize those efficient frequencies. For example, the element of each excitation vector associated with a particular transducer element may be coherently added to provide an optimized excitation waveform for said transducer element.

The optimized excitation waveforms for all transducer elements may be used to drive the transducer array to generate new focused image data using wideband imaging. Non-limiting examples of imaging modes used to generate wideband focused image data include STF, MTF, or cMTF. In some embodiments, the wideband excitation waveforms may be arbitrary waveforms, which may form a coded ultrasound wavefront.

The wideband focused image data may be used to evaluate focusing gains at the various control points. The focusing gains at the target points and the critical points, for example, may be evaluated by comparison to a threshold focusing gain. The new image data may be generated using focused imaging.

Examples of process 212 may relate to other processes or structures described herein. In FIG. 4, arbitrary waveforms for cMTF are computed in process 310 and pulse-echo imaging using cMTF is used to generate wideband focused image data in process 312. Then, the focusing gains at the target points are evaluated in process 314, and the focusing gains at the critical points are evaluated in process 316. In FIG. 5, the optimized excitation vectors 414 are provided to a multi-channel waveform generator to provide wideband excitation waveforms. In FIG. 8A, wideband excitation waveforms are synthesized in algorithm 700, for example, in lines 10 and 11. The waveforms may be used to generate wideband focused image data using wideband STF, for example, in line 12. Focusing gains based on the wideband focused image data may be evaluated, for example, in line 13. In FIG. 8B, wideband excitation waveforms may be synthesized in algorithm 701, for example, in lines 13 and 14. The waveforms may be used to generate wideband focused image data using wideband cMTF, for example, in line 15. Focusing gains based on the wideband focused image data may be evaluated, for example, in line 16.

In process 214, the solving the multiband optimization problem and the synthesis of wideband waveforms may be iterated based on the last focused image data generated if the evaluation of the focusing gains does not meet the evaluation criteria (for example, focusing gain thresholds). For example, if the measurements (for example, focusing gain) do not meet the criteria, additional focused image data may be iteratively generated until the criteria are satisfied. In other words, the method 200 may continue to repeat processes 210 and 212 until the focusing gains meet the evaluation criteria. In some embodiments, iterations may continue until both the target focusing gain is no less than the minimum threshold and the critical focusing gain is no greater than the maximum threshold.

In some cases, it may be determined that the focusing gains cannot meet the criteria and the method 200 may terminate. A user could be alerted that the desired focusing gain cannot be achieved. In other cases, it may be determined that the focusing gains do not meet the criteria but have converged and may be acceptable, for example, for imaging but not therapy. In particular, iterations may continue until one or both of the target focusing gain and the critical focusing gain converge in consecutive iterations.

Examples of process 214 may relate to other processes or structures described herein. In FIG. 4, if the focusing gains at any target point does not meet evaluation criteria in process 314, focused data matrices for at least the failing target points may be recomputed based on the wideband focused image data in process 322 to produce new excitation vectors. If the focusing gains at any critical points do not meet evaluation criteria in process 316, focused data matrices for at least the failing critical points may be recomputed based on the wideband focused image data in process 320.

In process 216, ultrasound energy for imaging or therapy based on the optimized excitation waveforms synthesized in process 212. Once the evaluation criteria are met, the optimized excitation waveforms may be used to drive the array of transducer elements for imaging or therapy in an efficient and optimized manner. In some embodiments, the optimized excitation waveforms may also be used to measure focusing gains for additional verification, refinement, or reporting, for example, during imaging or therapy.

FIG. 4 is another example of a method 300 for focusing ultrasound energy at one or more target points. Method 300 may be considered one embodiment of method 200 (FIG. 3) or a variant of method 200. Method 300 may begin with process 302, in which wideband cSA imaging is performed to generate initial image data and to identify a tissue volume (or region or interest, ROI), target points, and transmission and critical points of the obstacle.

The method 300 may continue on to process 304, in which virtual arrays are defined using the transmission and critical points determined in process 302. In particular, a proximal virtual array and a distal virtual array may be defined. A focused data matrix (FDM) may be computed for each target point based on the initial image data (for example, cSA image data). Also, as indicated, process 304 may also include determining or receiving a desired threshold focusing gain $\gamma_T$ and a desired critical gain $\gamma_C$.

For example, the focusing gain at the target, $G_T$, may be required to be higher than the threshold focusing gain $\gamma_T$, for example, in order to achieve an efficacious exposure level at the target (for example, a therapeutic gain). Additionally, or alternatively, the focusing gain at the critical point, $G_C$, may be required to be smaller than the threshold critical gain $\gamma_C$ in order to mitigate potential heating to the skull and scalp, which may be determined before ablative tFUS is applied. Failure to achieve either of these two goals may require that the corresponding propagation operator be remeasured in a new iteration towards finding an optimal solution that satisfies the treatment objectives.

In process 306, for each frequency in the bandwidth of the array, the FDMs computed in process 304 are used to compute regional propagation operators associated with the target points, such as regional propagation operator $H_{AV}$ (between the transducer array to a proximal virtual array), regional propagation operator $H_{VV}$ (between the proximal and distal virtual arrays), and regional propagation operator $H_{VT}$ (between the distal virtual array and the target points). In other words, a target point propagation operator $H_{AT}$ may be broken up into three regional propagation operators. $H_{AC}$ (between the transducer array and the critical points) may also be determined. In some cases, $H_{AC}$ may also be broken up into regional propagation operators if desirable (for example, when the critical point is located distal to the obstacle).

In process 308, for each frequency in the bandwidth of the array, an optimization problem is solved to maximize target focusing gain $G_T$ (related to complex pressure at a target point) while minimizing critical focusing gain $G_C$ (related to complex pressure at a critical point). Using the solution to the optimization problem to generate focused image data, $G_T$ and $G_C$ may be measured, for example, using narrowband MTF.

In process 310, arbitrary waveforms for cMTF may be computed for all N elements of the transducer array. In process 312, pulse-echo imaging may be performed using cMTF to estimate focusing gains $G_T$ and $G_C$. The estimated focusing gains may be measured at each frequency in the bandwidth of the array.

The estimated target focusing gain $G_T$ may be compared in process 314 to the threshold target focusing gain $\gamma_T$. If the $G_T$ is greater than $\gamma_T$ or there is no significant change between $G_T$ and at least one previous measurement of $G_T$, then the method 300 continues on to process 316.

In process 316, $G_C$ may be compared to $\gamma_C$. If $G_C$ is greater than $\gamma_C$, then the method 300 may continue to process 318, in which cMTF may be used for imaging or therapy. If $G_C$ is not greater than $\gamma_C$, then method 300 may recompute FDMs for the critical points based on the cMTF echo data in process 320. Then, the method 300 may repeat process 306.

In process 314, if the $G_T$ is not greater than $\gamma_T$ and there is a significant change between $G_T$ and at least one previous measurement of $G_T$, then the method 300 may continue on to process 322. In process 322, the FDMs may be recomputed for the target points based on the cMTF echo data. Then, method 300 may repeat process 306.

Method 300 may be useful for synthesizing broadband coded multiple-focus (cMTF) wavefronts using ultrasound arrays. The method 300 may utilize multichannel arbitrary waveform generation with wideband linear amplifier technology. The synthesis approach may be based on specifying the desired waveforms at a set of control points in the field. Each of these control points may be associated with an independent code with sufficient time-bandwidth product to meet a desired imaging and/or therapeutic performance criterion, such as focusing gain for intensity. The synthesized wavefronts may facilitate production of interference free, or almost interference free, multiple-focus patterns. In therapeutic applications, this may result in improved localization of the therapy by concentrating the energy at various target points. In imaging, this may allow for the increase of the frame rate and/or the signal-to-noise ratio (SNR) while minimizing the clutter.

Method 300 may be used to synthesize M pressure waveforms $p(\vec{r}_m, t) = g_m(t)$ at distinct control points $m=1, 2, \ldots, M$ and $\vec{r}_m = (x_m, y_m, z_m)$ using an array of N transducer elements. The function $g_m(t)$ represents the complex pressure value at the mth control point. The pressure waveforms may be synthesized by decomposing each $g_m(t)$ into its Fourier components and using, for example, a pseudoinverse pattern synthesis method at each frequency component $\{f_i\}$ to produce an excitation vector $u(f_1)$ using Equation 5A. One example of a pseudoinverse pattern synthesis method is described in E S Ebbini and C A Cain, "Multiple-focus ultrasound phased array pattern synthesis—Optimal driving signal distributions for hyperthermia," IEEE TRANSACTIONS ON ULTRASONICS FERROELECTRICS AND FREQUENCY CONTROL, vol. 36, no. 5, pp. 540-548, September 1989, which is incorporated entirely herein by reference.

$$u(f_i) = H^H(f_i)(HH^H(f_i))^\dagger p(f_i) \quad (5A)$$

The vectors $u(f_i)$ and $p(f_i)$ are N×1 and M×1, respectively. Each element $u_n(f_i)$ of the vector $u(f_i)$ represents the complex particle velocity driving the nth element of the array. Also, $(\bullet)^H$ denotes the Hermitian transpose, $(\bullet)^\dagger$ denotes the pseudoinverse, or the Moore-Penrose inverse, $H(f_i)$ is the propagation operator from the array aperture to the one or more control points. The propagation operator $H(f_i)$ may be computed or measured for, and thus may correspond to, a given array geometry and propagation medium. Each matrix element $H_{m,n}(f_i)$ represents the complex pressure at the control point m, or at $\vec{r}_m$, due to array element n driven by a unit particle velocity. In other words, $H_{m,n}(f_i)$ represents the directivity of element n and control point m.

The narrowband or continuous wave solution to Equation 5A may be an optimal minimum-norm least squares (MNLS) solution provided by the pseudoinverse. The pseudoinverse may be implemented based on singular value decomposition (SVD) of the propagation operator $H(f_i)$, such as an eigenvalue decomposition. A weighted MNLS solution based on a set of target points $M^T$ and a set of critical points $M^C$ may be linked to the transmit or receive beamforming through the propagation operators $H_T$ or $H_C$, respectively. The critical propagation operator $H_C$ may serve to define a weighting matrix $W_C = (H_C^H H_C + \gamma_C I)$, with $\gamma_C > 0$, which may be used to compute a weighted MNLS that minimize exposure at the critical points.

Narrowband multiple-focus synthesis may become ill-conditioned when spacing between control points approaches the dimensions of the array point spread function in a given direction. The criteria for optimal placement of control points may apply at all frequency components within the transducer bandwidth and may be considered in wavefront synthesis. Although the distribution of target points may depend on the application, the SVD-implemented MNLS solution may degrade when the number of control points is increased, the spacing between neighboring control points approaches the dimensions of the array point spread function, or both.

Wideband pattern synthesis may be performed by Equation 5A at a discrete set of frequencies within the bandwidth B of the desired waveforms. The bandwidth B may match the bandwidth of the transducer elements of the array. The number of frequency samples needed to capture the frequency contents of the temporal waveforms may be the same as that of the discrete Fourier transform (DFT) of sampled data. An assumption may be made that the sampling frequency may be chosen appropriately so that the Nyquist criterion is satisfied for bandlimited signals. An assumption may also be made that each frequency $f_i$ is associated with a waveform $g_m(t, f_i) = g(t) \cos(2\pi f_i t) = g(t)\Re\{e^{j2\pi f_i t}\}$, where $g(t)$ is a standard window function, such as a raised cosine, of duration $T^g$. For element n, the wideband synthesis problem may result in a driving waveform $u_n(t) = g(t) \sum_{m=1}^{M} \sum_{i=1}^{I} A_{imn} \cos(2\pi f_i t + \phi_{imn})$, where I are the number of discrete frequencies used in the synthesis process. The amplitude and phase coefficients may be obtained from the vector u in Equation 5A, where $A_{imn} = |u_n(f_i)|$ and $\phi_{imn} = \angle u_n(f_i)$.

The window function $g(t)$ may be selected to providing well-behaved waveforms for the proper synthesis of coded wavefronts, such as cMTF patterns. A standard window function with desirable time-frequency distribution may be used. In one example, the following raised cosine window described by Function 6A may be an appropriate choice:

$$g(t) = \begin{cases} 1, & |t| < \dfrac{T_g}{2} - t_x \\ \dfrac{1}{2}\left[1 - \sin\pi\left(\dfrac{t - T_g/2}{2t_x}\right)\right], & \left|t - \dfrac{T_g}{2}\right| < t_x \\ 0, & |t| > \dfrac{T_g}{2} + t_x \end{cases} \quad (6A)$$

with its Fourier transform given by $$G(f) = T_g \frac{\cos 2\pi t_x f}{1 - (4t_x f)^2} \frac{\sin \pi T_g f}{\pi T_g f}$$

In Function 6A, $0 \leq t_x \leq T_g/2$ controls the smoothness of the window. When $t_x = 0$, the Function 6A may provide a rectangular window and a corresponding sinc spectrum. On the other extreme, when $t_x = T_g/2$ the Function 6A may produce a classic Hanning window. The smoothness parameter $t_x$ may be chosen to reduce the leakage due to time gating. The zeroes of $G(f)$ occur at $f_n = \pm n/T_g$, which may provide a criterion for the window design, for example, relating to the spacing between the I carrier frequencies within the transducer bandwidth. Other criteria for the gating window design may include the geometric point spread function of the array at the different control points. One may choose $T_g$ large enough so that all the differences in time of arrival can be interpreted as phase lags, thus allowing the Function 6A to be used in the given form. This may affect the sampling of the transducer bandwidth at $\{f_i\}_{i=1}^{I}$.

FIG. 5 illustrates a functional diagram of a dual mode ultrasound transducer system 400. The system 400 may include a plurality of ultrasound transducer elements 402 forming an array 404. Each of the elements 402 may be configured to transmit and receive ultrasound energy. A bank of channel filters 406 may be coupled to the elements 402. Each element 402 may be coupled to one channel filter 406.

Received ultrasound energy may be used to generate channel data, which may be stored in the form of a channel data matrix 408. Focused data matrices 410 may be extracted from the channel data. Each focused data matrix 410 may correspond to a control point or a volume around the control point, which may also include other control points. In other words, each focused data matrix 410 may be associated with one or more control points. The focused data matrices 410 may be used to estimate propagation operators 412, for example, between the array 404 and the target points. The estimated propagation operators 412 may be used in the refocusing algorithm to generate excitation vectors at one or more frequencies to achieve desired focusing gains at one or more target points and one or more critical points. The excitation vectors 414 may be used to generate excitation waveforms, for example, by a multi-channel waveform generator, and which may be used to drive the ultrasound transducer array 404.

The channel data matrix 408 may represent spatially filtered data. For example, the channel filters 406 may include an axi-lateral filter derived from the excitation waveforms used to generate the measurements. For example, a pre-beamforming matched filter may be applied to the received pulse-echo data from all elements 402 (for example, a bandpass filter). The matched filter may utilize a time-reversed transmit waveform (such as an MTF or cMTF waveform). In some cases, a pseudoinverse filter may be used instead of the matched filter, which may improve decorrelation of different waveforms. Using the axi-lateral filter may provide axial compression. In some cases, spatial filtering may include matched or regularized inverse filtering of channel data pre-beamforming or after full or sub-aperture beamforming (e.g., post-beamforming of the full aperture or a sub-aperture). In some embodiments, axi-lateral filtering of channel data, pre-beamforming or after full or sub-aperture beamforming, may be used to compress channel data and improve axial resolution, lateral resolution, or both.

In contrast to systems performing ultrasound axial compression with one waveform, pre- or post-beamforming, the system 400 may utilize multiple matched filters, one for each transmitter. Each channel filter 406 may include one or more filters, each filter identifying a different waveform. The system 400 may utilize axi-lateral filtering for "wavefront compression" before evaluating a focused data matrix. Axi-lateral filtering may be used to improve resolution in one or both or the axial and lateral dimensions.

For illustrative purposes, the channel filters 406 may be used in the following manner. Transmit arbitrary waveforms may be focused at one or more target points. Waveforms may be obtained using a broadband wavefront synthesis. The excitation waveforms may be designed to produce a 2-focus cMTF with foci spaced by 1.2-mm axially (+/−0.6 mm from the geometric center of the DMUA. Additionally, or alternatively, excitation waveforms may be designed to produce a 2-focus cMTF with one focus at the geometric center and another placed 0.6 mm laterally. The coded waveforms may be multifrequency in nature. Echoes from the excitation waveforms may be recorded from each receive array element. A spatial filter, such as an axi-lateral filter, may be derived from the excitation waveforms and may be applied to channel data to obtain axial compression. The compressed channel data can be beamformed to extract one or more focused data matrices associated with one or more target points of interest. Due to the proximity of the target points, a single focused data matrix can be extracted from either the raw or compressed echo data. The compressed channel data may produce focused data matrices with better resolution of multiple targets.

A channel data matrix 408 may represent samples of one or more measurements using the array 404 (for example, raw or compressed). The columns may correspond to measurements made by each element 402. A measurement may correspond to pulse-echo data received after one excitation waveform. For example, a first set of columns may correspond to measurements by a first element 402, a second set of columns may correspond to measurements made by a second element 402. Each of the columns may correspond to one measurement. Each row may correspond to consecutive samples collected in each measurement. The number of rows may correspond to a physical depth of field of the image data.

In one example of a channel data matrix 408, an array 404 having 32 elements 402 may take 32 measurements and 4000 samples for each measurement. Each measurement may correspond to one of the elements 402 transmitting a pulse (for example, in succession), which is received by each of the elements of the transducer array 404. In one arrangement of the channel data matrix 408, the first 32 columns generated may correspond to the measurements made by the first element 402 based on transmissions made by each of the elements of the array 404. The measurements may be arranged in chronological order. The matrix may have 4000 rows, representing the 4000 samples by each element 402 for each measurement. The rows may be arranged in chronological order. Overall, the channel data may be represented by a 4000 by 1024 channel data matrix 408.

The channel data matrix 408 may be modified by post-beamforming, such as SA beamforming to generate image data. Each focused data matrix 410 may be a truncated version of the channel data matrix 408 after coarse beamforming (see FIG. 6 and related description). Compression of the channel data by the channel filters 406 (for example, axi-lateral filtering) may be used to produce better resolution of multiple control points in each focused data matrix 410.

Each focused data matrix 410 may be associated with one or more control points. The image data associated with the one or more control points in the focused data matrix 410 may be estimated, for example, using SVD, such as an eigenvalue decomposition of the associate covariance $X^H X$, where X is the focused data matrix 410 and $[\bullet]^H$ is the Hermitian transpose (transposition and complex conjugation). The decomposition of each focused data matrix 410 may produce a directivity vector, which may be the same size as the array 404 and include amplitude information describing the sensitivity of each element 402 and phase information describing the degree of misalignment of the waveforms at the control point being targeted. The directivity vector may be used to refocus the image data in the focused data matrix 410. Each directivity vector may be associated with a particular frequency band or discrete frequency.

The directivity vector and the focused data matrix 410 may be used to compute an excitation vector for each control point associated with the focused data matrix. The excitation vector may be generated using one or more regional propagation operators, which describe propagation between the array 404, the virtual arrays, and the target points.

The excitation vectors 414 may be used to generate a set of excitation waveforms. In particular, the excitation vectors 414 may be associated with single frequency bands. Each excitation vector may generate a set of raised cosine waveforms with phase lags or delays obtained using the selected synthesis method. Raised cosine waveforms from different excitation vectors may be summed (for example, on an element-by-element basis) to generate the set of excitation waveforms.

The excitation waveforms may be used to generate arbitrary waveforms for a cMTF imaging mode. The excitation waveforms may be used to generate focused image data. Focusing gain at the target points and the critical points may be determined. If the focusing gain does not converge and does not meet certain criteria, then focused image data may continue to be iteratively generated. Otherwise, if focusing gain converges or meets certain criteria, the result may be used for ultrasound imaging or therapy or may be otherwise provided, for example, in a report to the user of the system 400.

FIG. 6 illustrates an example of pulse-echo data 500. Graph 502 illustrates a control point P, which is an ultrasound reflector. Using the central ultrasound transducer element 504, a Gaussian-modulated sinusoid may be transmitted and reach the control point P. The ultrasound energy may be reflected off control point P to the ultrasound transducer array 506 including central element 504. Graph 510 represents the waveforms of the reflected ultrasound energy received by various elements of the array 506 (for example, pulse-echo data) when transmitted through a homogeneous medium. As can be seen, the modulated sinusoids in graph 510 are not aligned because the arrival times are different for each element of the array 506 due to the different distances between each element and the control point P. In the case of an inhomogeneous medium, the arrival times would vary even further from these nominal values in a homogeneous medium. The channel data may represent the waveforms in graph 510. Beamforming or spatial-temporal filtering may be used to align the waveforms. For example, a different delay may be applied to data received by each of the elements of the array 506 (or channels). A focused data matrix may be used to truncate the aligned channel data (for example, a time window), as shown in graph 512, to isolate the aligned echoes and minimize echo components from other regions. Using a focused data matrix may provide better data, for example, compared to using a raw channel data matrix.

Figure 7:
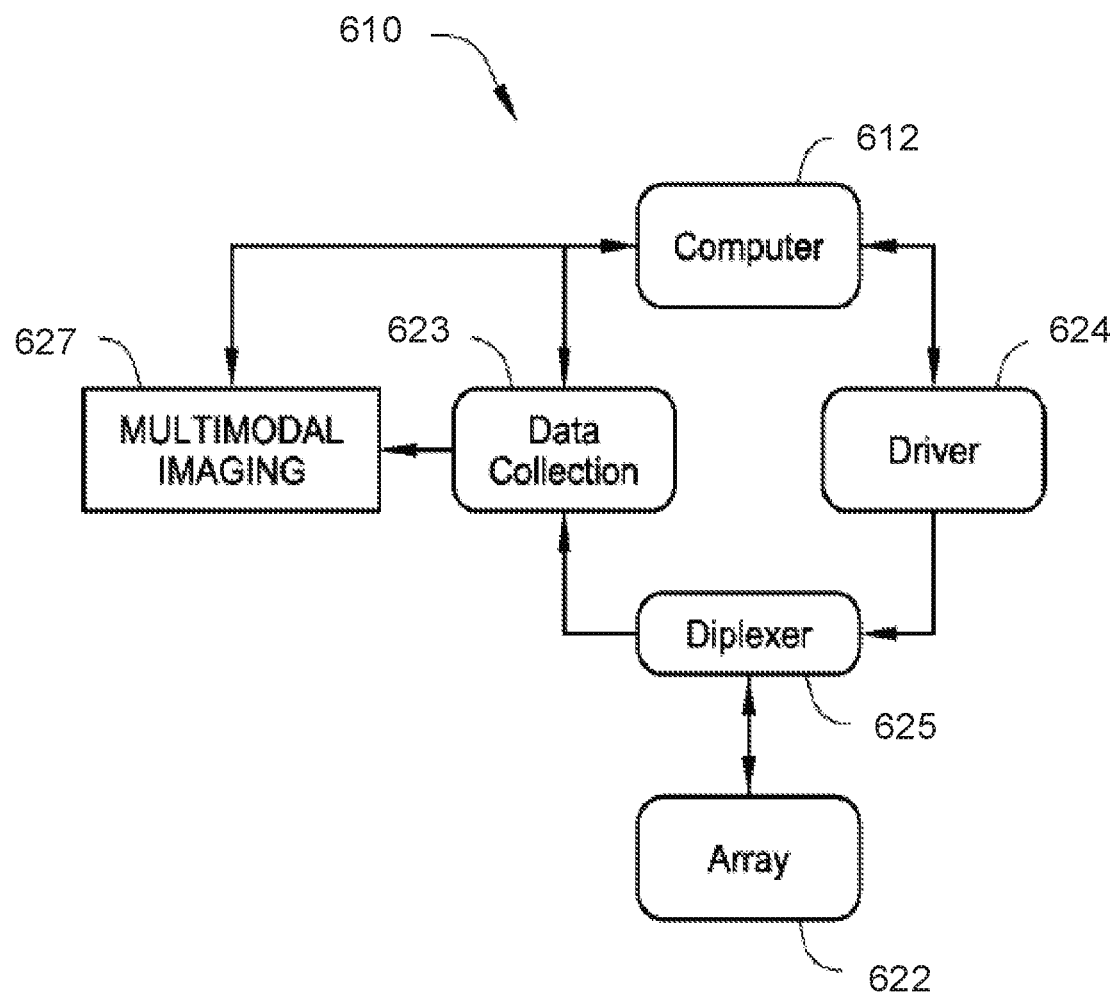
FIG. 7 is a block diagram of a system for refocusing ultrasound.

FIG. 7 illustrates a block diagram of one exemplary implementation of therapy system 10 (FIG. 1) which uses a dual mode ultrasound array (DMUA) for providing therapy; as well as for use in control of such therapy using imaging by way thereof. The therapy system 610, includes dual mode ultrasound array (DMUA) 622, computer 612 (for example, control apparatus of FIG. 1), multi-modal imaging 627, data collection 623 (for example, signal acquisition), driver 624 (for example, DMA driver), and diplexer apparatus 625 (for example, a configurable diplexer; such as a diplexer for each control channel associated with each transducer of the array 622).

The ultrasound transducer array 622 may be any apparatus (for example, transmitting, receiving components, etc.) capable of delivering therapeutic and subtherapeutic ultrasound energy and sampling/collecting ultrasound echo energy contemplated to be used in ultrasound imaging systems and/or therapy systems. As used herein, such transducers may include a transmitting portion, for example, to deliver ultrasound energy, and a receiving portion, for example, to sample/collect echo or reflected energy, which may or may not be the same portion. During the ultrasound imaging of a target (for example, a tumor, a vessel, etc.), the transducer array 622 may be positioned relative to the target so as to be capable of delivering energy to the target resulting in reflected energy (also known as the resultant pulse-echo or echo energy) and also sampling the echo energy. Further, the transducers of array 622 may be capable of delivering therapeutic bursts (for example, forming and delivering a therapeutic beam of ultrasound energy over time).

In one of more embodiments, the dual mode ultrasound array 622 is an array with multiple transducers (for example, each drivable through a separate control channel). The array 622 may use any suitable number of transducers to provide the desired resolution and performance. In some embodiments, the array 622 includes thousands of transducers, or hundreds of transducers (for example, using coded excitation). The number of transducers, the DMUA geometry (for example, typically concave, but which may be of any other suitable geometry) and the transducer distribution may be determined by the nature of the target (for example, as defined by depth and volumetric dimensions, such as axial depth and lateral width) and the presence of obstacles in the path of the therapeutic beam (for example, the skull).

Once a DMUA is designed, it may be characterized by the DMUA's imaging field of view (IxFOV) and optionally the DMUA's therapeutic operating field (ThxOF). For example, a 32-element DMUA operating at 3.5 MHz that is designed for tissue therapy may have an elliptically shaped ThxOF around its geometric center extending by about 1.6 cm axially and about 0.8 cm laterally. The DMUA's IxFOV may be nearly twice the size of the DMUA's ThxOF. Further, for example, another DMUA prototype operating at 1 MHz may be a 64-element DMUA with a concave array having an elliptically shaped ThxOF with dimensions 5 cm axially and 3 laterally with an IxFOV roughly twice that size.

The ThxOF may be defined as the volume around the geometric center of a target where the focusing gain of the array (for example, for an electronically steered focus) does not fall by more than 3 dB. At least in one embodiment, an effective array design may balance the efficiency (which typically calls for larger elements) with the need for sufficiently large ThxOF (which typically calls for smaller elements). This may also be governed by other factors like the aperture size, operating frequency, cross coupling characteristics of the transducer, etc. Power efficiency considerations almost surely dictate element dimensions in the $1.5\lambda$-$3\lambda$ range, where $\lambda$ is the wavelength. This coarse sampling of the array aperture may be the cause of the grating lobe phenomenon. Grating lobes may potentially create hot spots away from the intended target location in therapy modes. In imaging modes, grating lobes may limit imaging contrast and may create artifacts.

In some embodiments, hardware and software platforms that allow for real-time image formation and signal processing of DMUA echo data for characterization of the tissue response to HIFU exposure may be used. For example, refocusing/resynthesis based on imaging feedback with millisecond latency may be implemented. This may be enhanced by the use of multi-channel drivers with real-time arbitrary waveform generation on different DMUA channels.

Further, for example, various imaging modes may be used to further improve the specificity of the DMUA imaging to HIFU-tissue interactions, both at the therapeutic and subtherapeutic levels. For example, such imaging modes may be designed to capture the thermal, viscoelastic, and non-linear response to HIFU beams, especially in the subtherapeutic range. In addition, imaging modes for estimation of cavitation threshold and tissue absorption in situ may be used.

Coded wavefronts using arbitrary waveform generation may be designed to be largely orthogonal to each other. In general, for example, depending on the geometry of the transmitting array 622, the number of elements, and the depth of the waveform memory, coded transmit beamforming can be used to generate multiple focal points where the spatial-peak, temporal-average intensity ($I_{SPTA}$) is sufficient to produce measurable effects, such as heating or other effects.

The focusing and the pulse repetition frequency (PRF) of the transmit pattern may allow for control of the $I_{SPTA}$ at the desired control points to produce the measurable effects. For example, the $I_{SPTA}$ may be designed to be maximized at target points and minimized at the critical points. Non-thermal therapeutic effects can be achieved by synthesizing transmit patterns with spatial-peak, temporal-peak intensity ($I_{SPTP}$) levels at the target points to maximize cavitational or shearwave generation with minimal heating. One advantage of using arbitrary waveform generation and coded excitation in synthesizing therapeutic array patterns is that interference patterns outside the target points have $I_{SPTA}$ and $I_{SPTP}$ levels that can be much lower than their conventional counterparts (for example, interference patterns resulting from continuous wave or conventional pulse wave excitation). The therapy system 610 may allow for the use of coded excitation in therapeutic mode as well as in imaging mode.

High frame-rate DMUA imaging may allow for the reliable estimation of tissue motion and deformation through speckle tracking and similar methods. This may also allow for the measurement of 2D or 3D flow. As such, this may provide a reliable approach to estimate the localized tissue response to the ultrasound energy beam, even when delivered subtherapeutically.

The computer 612 (for example, control apparatus) may serve as a platform for a wide array of real-time signal processing operations. The computer 612 may control multimodal analysis of image data to expand on conventional imaging to expose tissue dynamics as they happen. The computer may be configured to present results to a user in real-time, allowing for instant feedback and control.

The computer 612 may be provided with data from data collection 623 (for example, image data from an analog to digital converter) and may provide an output to driver 624 (for example, configured as a FPGA for receiving therapy signals and imaging signals to drive the array 622).

The computer 612 may include multiple CPUs and GPUs for processing data to reconfigure the array 622 to generate ultrasound energy based on generated image data. GPU and Core i7 represent specific processors configured to execute the instructions for carrying out functionality as described herein. For example, multi-modal imaging 627 is illustrated as part of the computer 612 and can include a variety of data and signals. Multi-modal imaging may include a bandpass filter, a module to provide SA beamforming (for example, serial excitation of sensor elements and detection by non-excited elements), a module to provide coded SA beamforming, a module to provide STF beamforming, a module to provide MTF beamforming, a module to provide cMTF beamforming, a module to provide a Hilbert Transform module, and an envelope detection and log compression modules. Each of these modules can provide data for use by the multi-modal imaging module for use in analyzing the image data and refocusing the array. For example, the multi-modal imaging module can be configured to perform one or more different imaging analysis, which may not be limited to ultrasound energy beam mapping (for example, to control beam refocusing), echogenicity measurements (for example, to determine focusing gain), cavitation detection (for example, to detect cavitation, such as bubbles), acoustic radiation force measurements (for example, to produce tissue displacements and measuring tissue displacement using speckle tracking), and tomographic imaging (for example, to image using reconstruction techniques for identifying targets or use in controlling therapy). User input through a user interface may include decision making by the user and user control.

On the CPU side, data can be come from a network stack (for example, experimental mode, where data is streamlined from SonixRP scanner or another diagnostic scanner with a research interface) or data file (for example, review mode). The processed result can be visualized with a designed UI system (OpenGL based) or exposed to other commercial software for further analysis (for example, Matlab). The CPU result can be used to provide feedback control of the therapeutic beam. For example, upon selection of control points, calculations may be carried out to generate therapy signals for communication to driver 624.

Further, each of the ultrasound transducers of the array 622 may be coupled to the rest of the system 610 by a control channel, which may include a diplexer 625 for each element or any other operable coupling (for example, a diplexer or switch to manage the coupling of signals between the driver 624 and the array 622 (for example, therapeutic and subtherapeutic signals) and between data collection 623 and the array 622. In other words, a multi-channel control to/from the array 622 may be implemented. For example, an array of A/D convertors may be coupled to the transducers of the array 622 (for example, in a one to one relationship, or multiple transducers per converter, etc.). Signal levels at the array during therapeutic operation may be in the range of 100's of volts, whereas signal levels at the array during imaging operations may be in the range of millivolts. As such, one or more configurations of the diplexer may be more beneficial over others.

Signal acquisition for data collection 623 (for example, pulse-echo image data) may be performed in any suitable manner. For example, a transducer signal may be sampled at 40 MHz, 12 bits, full scale range 1V (for example, the element samples approximately 1 MHz, and the 40 MHz sampling rate is far in excess of that required by the Nyquist principal); each channel may have an independent digital filter and reconfigurable down-sampler; the data may be filtered in real-time and stored in memory; and the data may be communicated to the computer for further processing.

A DMUA element may provide an analog signal that may be translated into a digital signal read in by the computer though some standard interface (USB, Ethernet, etc.). A single channel for data collection 623 between a transducer of an array 622 and the computer 612 may include an analog to digital convertor (ADC) for sampling the signal from the transducer of the array 622. A single channel of a multi-channel data acquisition system may be implemented, for example, using an FPGA. The ADC may be continuously converting the analog signal at its input, for example, into a digitized word. A triggering unit may control when this data is read into the FPGA including A-line storage. Once triggered, the FPGA may latch the data into the device and route it through a DSP processes (for example, a decimator and any filtering). The FPGA may then store contiguous samples (for example, A-line storage). Once stored in the FPGA, the computer 612 can then download the data and commence further processing.

The DMUA driver 624 may include a multichannel driver configured to drive the DMUA elements with independent waveforms in both therapeutic and image modes. Further, the DMUA driver 624 may be configured to store and control the signals (for example, therapy and image signals) to be used by the DMUA elements to generate ultrasound energy. The driver 624 may be any suitable maging. In some embodiments, the driver 624 may be capable of SA imaging or cSA imaging and may also capable of STF imaging or cMTF imaging.

Multimodal imaging 627 may be coupled to the data collection 623 and computer 612. Multimodal imaging 627 represents circuitry and programming suitable for performing one or more modes of imaging, such as for use in control of the ultrasound energy waveforms (for example, for use in analyzing movement of the subject and other tissue dynamics or response).

Image data may include thermal response data for feedback after ultrasound energy is delivered (for example, such as in the use of power reallocation amongst the elements of the array). Image data may include data indicative of cavitation. Such data indicative of cavitation may be used to control the focused beam in any number of ways. For example, such data may be used to define the ultrasound energy waveforms such that the subtherapeutic burst produces reduced heat at regions where cavitation is appearing but is undesirable, to increase at target points where cavitation is desired but not occurring, etc.

For example, such data indicative of cavitation may include the detection of bubble activity on tissue. For example, such bubble activity may be detection using image data and algorithms described in U.S. Pat. No. 6,951,540 to Ebbini et al., entitled "Ultrasound imaging system and method using non-linear post-beamforming filter" and H. Yao, et al., "Enhanced lesion visualization in image-guided noninvasive surgery with ultrasound phased arrays," in *Proc. 23rd Annu. Int. Conf. IEEE Eng. Med. Biol. Soc.*, October 2001, vol. 3, pp. 2492-2495, which are all incorporated entirely herein by reference.

Image data may include tissue displacement/strain data (or any other mechanical response data associated with the target region, such as temperature change data, cavitation activity data, etc.). Such displacement/strain data may be used to control the focused beam in any number of ways. For example, such data may be used to identify oscillations indicative of cavitation at the target points, as well as other points in the path of the beam. Further, for example, such data may be used guide the beam with respect to the target points as the target points are displaced. In other words, for example, in one or more embodiments, pulse-echo data suitable to provide displacement fields in flow and/or tissue may be used to generate control image data. For example, such displacement/strain data may be used to refocus the beam to the target points based on the displacement/strain data.

It will be recognized that multiple types of image data may be used to synthesize excitation waveforms. For example, thermal response data may be used with directivity data, displacement data may be used with thermal response data, or any other combination of image data may be used.

FIG. 8A illustrates an example of an algorithm 700 (Algorithm 3) for carrying out a method of multiband transcranial refocusing. Algorithm 700 may be considered one algorithm used to carry out method 200 (FIG. 3) or a variant of method 200. The algorithm 700 optimizes focusing gains in the multiband or wideband case. In particular, the algorithm 700 seeks an optimal solution that minimizes the exposure to certain points (for example, on the skull) that are deemed to be inefficient (for example, critical points).

The algorithm 700 may begin with initializing synthetic aperture imaging. Propagation operators to one or more target points and to one or more critical points may be estimated. STF imaging may be performed at each frequency in the bandwidth of the array (i=1, . . . , $N_F$). The propagation operators to each target point and to each critical point may be measured at each frequency. Based on the measured propagation operators, the focusing gain at each target point and at each critical point may be evaluated at each frequency.

An optimization problem may then be solved based on the measured propagation operators to determine an optimal excitation vector at each frequency. Optimization may utilize a Lagrange multiplier, or a minimum-norm least-squares (MNLS), solution or another optimization algorithm based on the defined operators.

One example of optimization may avoid each critical point and treat the rest of the points in the path of the beam as friendly for transmission. For example, a critical point may be around a point with the highest reflectivity around a known strong reflector, such as the median of a skull (for example, the median plane). Avoiding the critical points may improve focusing gain and tighter focusing. However, this form of optimization may not capture the different characteristics of propagation in different regions of the tissue volume.

Another example of optimization may utilize one, two, or more virtual arrays created based on the SA image data to characterize different regions of the tissue volume. One virtual array may be related to a distal surface of an obstacle and another virtual array may be related to a proximal surface of the obstacle. Each virtual array may be defined in terms of a point spread function of the transducer array or a sub-aperture of the transducer array at the surface of the obstacle. In other words, the lateral dimensions of the beam produced by the transducer array at or near the corresponding obstacle surface may define the size of the virtual array element at said surface. Points or elements of the virtual array need not contiguous. In some cases, only their maximum extent is necessary for the formulation of the refocusing problem.

Further, an excitation vector may be synthesized based on STF image data by, first, modeling a homogeneous propagation between the distal virtual array and each target point, which may be characterized as a first propagation operator. This may presume that the tissue region between the distal virtual array and the target point is generally homogeneous. Backpropagating a complex wavefront from the distal virtual array to the proximal virtual array based on estimated transmission coefficients based on the STF image data, which may be characterized as a second propagation operator. Third, modeling a homogeneous propagation between the proximal virtual array and the transducer array, which may be characterized as a third regional propagation operator, to find an optimal excitation vector.

Testing the focusing quality of the optimal solution may use various techniques and may be done in real-time (for example, between bursts or pulses in HIFU), such as measuring echogenicity, measuring heating, measuring cavitation, or measuring tissue displacement. Measuring heating may be particularly relevant to evaluating the therapeutic gain of the refocused beam.

Transmit pulses for testing the focusing quality of the optimal solution may be synthesized using a sum of modulated sinusoids with well-defined time-bandwidth products, as shown on line 10 of algorithm 700 of FIG. 8A, where g(t) has a narrowband Fourier transform, for example, G(f)≈0 for

|f|>W, where W is a predefined bandwidth (e.g. 100 kHz) within the transducer bandwidth, and W<<$f_i \forall$ i=1, 2, ..., $N_f$. Each carrier frequency may be associated with the narrowband wave packet with a group delay defined by the system (for example, the transducer element and the transmission medium) frequency response for the particular carrier frequency.

When utilizing algorithm 700, which utilizes multiband optimization, the transmission efficiency and the therapeutic gain may utilize some or all the available bandwidth. Transmission efficiencies through an ultrasound distorting obstacle, such as the skull, may be evaluated using STF.

At least with respect to algorithm 700, all references to SA can be generalized to include cSA. Similarly, all references to STF can be generalized to include MTF and cMTF.

FIG. 8B illustrates an example of an algorithm 701 (Algorithm 1) for carrying out optimization of transmit waveforms for cMTF synthesis. Algorithm 701 may be considered one algorithm used to carry out method 200 (FIG. 3) or a variant of method 200. Given a specified set of control points and corresponding waveforms $g_m(t)$, algorithm 701 shows procedures used in a cMTF pattern synthesis.

In the initialization stage, wideband SA imaging may be used to identify one or more target points, the obstacle, and one or more critical points. Candidate transmission points on the obstacle may also identified at this stage.

The algorithm 701 may then proceed to find and test the narrowband excitation vectors $N_F$ at the set of frequencies $\{f_i\}_{i=1}^{N_F}$ within the transducer bandwidth using, for example, narrowband SA. For each frequency, the operators $H_T(f_i)$ and $H_C(f_i)$ may be measured based on the identified obstacle and candidate transmission points. The transmission points may define the virtual arrays proximal and distal to the obstacle. Once the virtual arrays are identified, the propagation operator $H_T(f_i)$ from the array to the target point(s) may be constructed from a cascade of three propagation operators: $H_{AV}(f_i)$ from the physical array to the proximal virtual array, $H_{VV}(f_i)$ from the proximal virtual array to the distal virtual array, and $H_{VT}(f_i)$ from the distal virtual array to the one or more target points.

If one or more of the critical points is located distal to the obstacle, then the associated propagation operator $H_C(f_i)$ can be computed similarly to $H_T(f_i)$. Otherwise, computing $H_C(f_i)$ may be computed as the propagation operator from the physical array to the critical point(s) on the proximal side of the obstacle.

Algorithm 701 may be used with either one-step or three-step optimization. In one-step optimization, the algorithm 701 may determine propagation operators based on virtual arrays and cascade the propagation operators before performing optimization. In particular, the algorithm 701 may find a single regularized solution to the cascade of the three propagation operators $H_C(f_i)$, $H_T(f_i)$, and $H_C(f_i)$. In three-step optimization, the algorithm 701 may solve three optimization problems, one for each of the three regions defined by the propagation operators. As illustrated in FIG. 8B, a one-step optimization is shown.

Once any cascaded propagation operators $H_T(f_i)$ and $H_C(f_i)$ are defined, the optimization problem may be solved using the appropriate criterion to provide an optimal solution $u_{opt}^{(i)}$. In general, the algorithm 701 may find a single regularized solution to the cascade of three propagation operators. The three-step algorithm may solve three optimization problems, one for each of the three regions.

The optimal solution $u_{opt}^{(i)}$ may then be tested as a narrowband MTF by evaluating the focusing gains at the target and critical point(s). Depending on the measured focusing gains, the optimal solution can be iterated $u_{opt}^{(i+1)}$ by using the results of the narrowband MTF to refine the estimates of the propagation operators and, possibly, change the virtual array configuration. For compactness, the iteration step is not shown in FIG. 8B.

At least with respect to algorithm 701, all references to SA can be generalized to include cSA. Similarly, all references to STF can be generalized to include MTF and cMTF.

FIG. 9 illustrates an example of an algorithm 702 (Algorithm 4) for carrying out a method of defining a focused data matrix $X_m$. A focused data matrix $X_m$ may be formed from channel data around any given point, such as a control point. In particular, algorithm 702 defines a focused data matrix $X_m$ based on the number of elements in the transducer array, echo data from STF imaging at each frequency $f_i$ (or within a narrow frequency band including the frequency) in the bandwidth of the transducer array, the coordinates of the control point $r_m$, and a region of interest RoI within a radius R around the control point. A set of narrowband filters may be used to isolate the echo data for each frequency from the channel data. Preferably, the narrowband filters provide precise control of phase and magnitude response, which may allow for real-time combining of different frequency bands. Combining different frequency bands in this manner may maximize their coherency. In general, radius R around the control point $r_m$ should be larger than the correlation length of the imaging pulse, larger than the expected variation in arrival times due to obstacle distortion, or both. Each focused data matrix $X_m$ may include rows L that represent sample data and columns N that represent the elements of the transducer array.

At least with respect to algorithm 702, all references to SA can be generalized to include cSA. Similarly, all references to STF can be generalized to include MTF and cMTF.

Equation 7 may be used to generate the focused data matrix. The columns of the focused data matrix may be formed from transducer element echo data by a crude beamforming operation combined with narrowband filtering at frequency $f_i$. The index n identifies a transducer element n, and index i identifies the frequency. The beamforming may be based on approximate delays associated with target or critical point m. The index m identifies the control point (for example, a target or critical point).

$$X_m(:,i,n) = \mathcal{F}_{fi}\left\{RF_n\left(\left[\frac{2 * R_{m,n}^{min} * F_s}{c}\right] : \left[\frac{2 * R_{m,n}^{max} * F_s}{c}\right]\right)\right\} \quad (7)$$

The focused data matrices $X_m$ at selected points on the obstacle surface may be used to define the elements of virtual arrays as well as the transmission coefficients between them. Specifically, the singular modes of the focused data matrix $X_m$ at a given location on the obstacle may reveal information about the transmission coefficients in the region of interest RoI determined by the focused data matrix $X_m$. The focused data matrix $X_m$ may also be back projected (toward the transducer array) to estimate the size of the corresponding virtual array element centered at the same point.

The narrowband filtering for Equation 7 may be performed using infinite impulse response (IIR) filters, in either analog or digital forms. Preferably, a low order Butterworth filter for each frequency band would be preferred. For example, a low order IIR filter may be a $2^{nd}$ order IIR filter, such as a biquad. The narrowband filtering may also be performed using a sliding Discrete Fourier Transform (DFT) filter, such as one described in International Application Publication No. WO2015013196A2, filed Jul. 21, 2013, entitled ULTRASOUND IMAGE FORMATION AND/OR RECONSTRUCTION USING MULTIPLE FREQUENCY WAVEFORMS. The output of the narrowband filtering may be a complex output that represents a trace in the time-frequency plane of the echoes received by an element of the transducer array.

In some cases, the IIR filter may be more computationally efficient than conventional finite impulse response (FIR) digital filters. The IIR filter in analog form may be particularly suitable, for example, when implemented with one or more monolithic integrated circuits (ICs), which may allow for the analog filter to be programmable. A digital narrowband filter, such as an IIR or FIR filter, may be implemented using FPGA technology.

In some cases, filtering may be implemented using one or more of a digitally programmable analog filter, a surface acoustic wave device, and a mixed analog-digital transmit-receive network.

Once a focused data matrix $X_m$ is determined, an eigenvalue decomposition may be performed on the associated covariance matrix, $X_m^H X_m$, as shown by Equation 8. The eigenvector corresponding to the maximum eigenvalue is the eigenvector that produces the maximum alignment between the channel waveforms represented by the columns of the focused data matrix $X_m$.

$$X_m^H X_m = E\Lambda E^H, \Lambda = \text{diag}\{\lambda_1, \lambda_2, \ldots, \lambda_N\},$$
$$X_m^H X_m e_i = \lambda_i e_i. \quad (8)$$

When assuming a narrowband model, the estimated propagation operators may be modified, or iteratively updated, according to Equation 9. In other words, the elements of the propagation operator vectors $H_T$ and $H_C$ may be updated according to Equation 9.

$$h^{(i+1)}(\vec{r}_m) = [h_1(\vec{r}_m)e_{i1}, h_2(\vec{r}_m)e_{i2}, \ldots, h_N(\vec{r}_m)e_{iN}] \quad (9)$$

Figure 15:
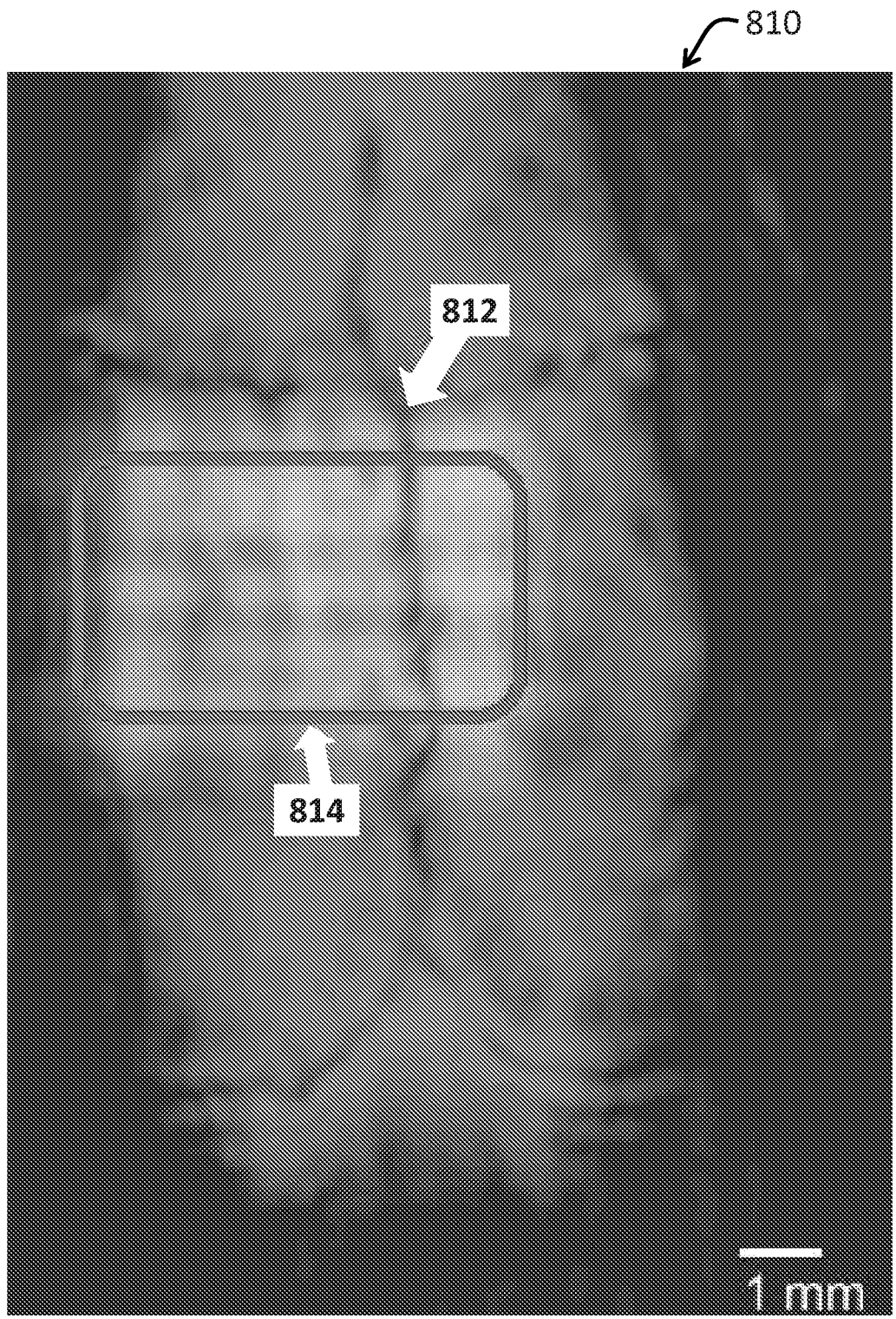
FIG. 15 is top view image of a skull surface rendered from 3D DMUA imaging data that shows suture lines. The arrow points to the intersection of bregma and medial suture lines. The highlighted region within the rectangle represents a portion of a skull in the path of a tFUS beam.

FIG. 15 is a top view image 810 of a skull surface rendered from 3D DMUA imaging of a live animal. The image 810 represents one example of the ability to define a virtual array using DMUA imaging of an obstacle. The surface of the obstacle may be characterized using 3D DMUA imaging. The surface characterization may be used to identify anatomical markers such as the suture lines. In the image 810, to the intersection 812 of bregma with medial suture lines. The highlighted region 814 within the rectangle may contain all the possible elements of virtual arrays to be used in the synthesis of refocused tFUS beams. The elements of a virtual array may be defined within this region 814.

Figure 16:
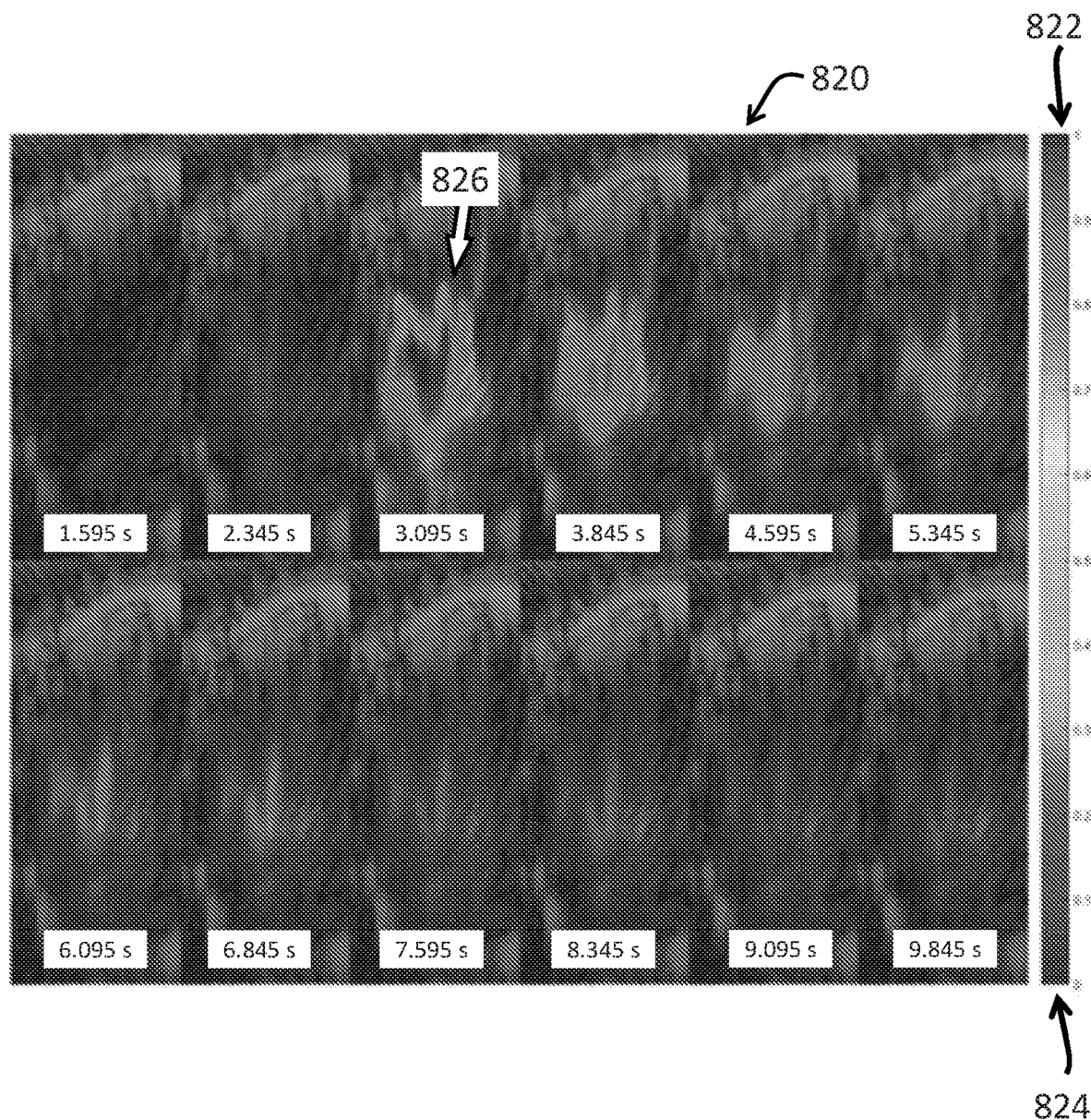
FIG. 16 are images of real-time ultrasound thermography used to visualize subtherapeutic heating patterns for evaluating focusing gain.

FIG. 16 are images 820 of real-time ultrasound thermography, which may be used to identify subtherapeutic heating patterns for evaluating focusing gain. The montage of images 820 shows temperature profiles before, during, and after the application of a 1-sec subtherapeutic tFUS heating pattern in vivo. The false color map shows the maximum heating in red colors 822 and zero temperature change in blue colors 824. The profiles in the images 820 demonstrate the localized heating, such as localized heating area 826, with a certain level of distortion which is indicative of the defocusing due to the skull obstacle.

While the present disclosure is not so limited, an appreciation of various aspects of the disclosure will be gained through a discussion of the specific examples provided below. In particular, the examples provided below show that wideband transducer and driver technologies together with the real-time implementation of refocusing algorithms may allow for adaptive imaging and refocusing to automatically perform broadband refocusing based on real-time user selection of the target and critical points on real-time SA imaging of the treatment region, or target region. The use of 3D guidance may also allow for a high degree of repeatability of outcomes. The results demonstrate the advantages of refocusing at every available frequency throughout the transducer bandwidth. The use of real-time site-specific refocusing allows for synthesizing refocused tFUS beams with the maximum operating bandwidth available by the transmission characteristics of the skull to the target point(s). Various modifications of the examples, as well as additional embodiments of the disclosure, will become apparent herein.

Example 1

The equipment used in this example was based on the equipment described in U.S. application Ser. No. 13/702,813, published as U.S. Publication No. 2013/144165, entitled DUAL MODE ULTRASOUND TRANSDUCER (DMUT) SYSTEM AND METHOD FOR CONTROLLING DELIVERY OF ULTRASOUND THERAPY, but modified as discussed in the present disclosure to enable various refocusing functionality.

A trans-skull refocusing experiment in vitro was performed using SA image for guidance and STF imaging with geometric focusing and with multiband refocusing. The obstacle was a skull and at least partially distorted ultrasound energy.

The dual mode ultrasound array (DMUA) of transducer elements was used in synthetic-aperture (SA) imaging mode for guidance and in single-transmit-focus (STF) mode for monitoring. These imaging modes are described in E. S. Ebbini, H. Yao, and A. Shrestha, "Dual-mode ultrasound arrays for image-guided surgery," Ultrasonic Imaging, 28:65-82, April 2006 and YWan and E S Ebbini, "Imaging with concave large-aperture therapeutic ultrasound arrays using conventional synthetic-aperture beamforming," IEEE Trans. UFFC, 55(2):368-383, February 2008, which are all incorporated herein by reference. The STF imaging used is akin to plane wave imaging, but the transmit beam of ultrasound energy used here was focused at the target point using imaging pulses of ultrasound energy having a duration on the order of sub-microseconds. Dynamic receive beamforming was also applied throughout the field of view.

In particular, SA imaging employed focusing, on both transmit and receive, for every pixel to provide very high contrast and dynamic range. For an array with N elements, each imaging frame used N different transmissions, each transmission using one transmit element and N simultaneous receiving elements. The $N^2$ channel data sets for each SA frame was transferred to a graphics processing unit (GPU)-equipped workstation using gigabit Ethernet. Beamforming was applied in real-time. This system supported real-time SA frame rates of approximately 30 fps, as described in A. J. Casper, D. Liu, J. R. Ballard, and E. S. Ebbini, "Real-time Implementation of a Dual-Mode Ultrasound Array System: In Vivo Results," Biomedical Engineering, IEEE Transactions on, Pre-publication, May 2013(99):1-1, 2013. The adaptive refocusing algorithms described below utilized raw channel data from the system.

Image data was captured, and echogenicity was displayed using a grayscale 40-dB dynamic range to demonstrate the relative visibility of the target point compared to the critical point in the different imaging modes. The coordinates of the target point X were at (x, z)=(0, 40) mm, and the coordinates of the critical point O were at (x, z)=(0, 31.2) mm. The target point was selected to be near a hydrophone location, and the critical point was selected to be at the median of the skull surface. The results herein are narrowband in nature and should be improved with multiband pre- and post-beamforming.

FIG. 10 illustrates an SA image 800, or initial image data, that was generated. The SA image was used to identify the target point in a target region and to identify the critical point.

Figure 11:
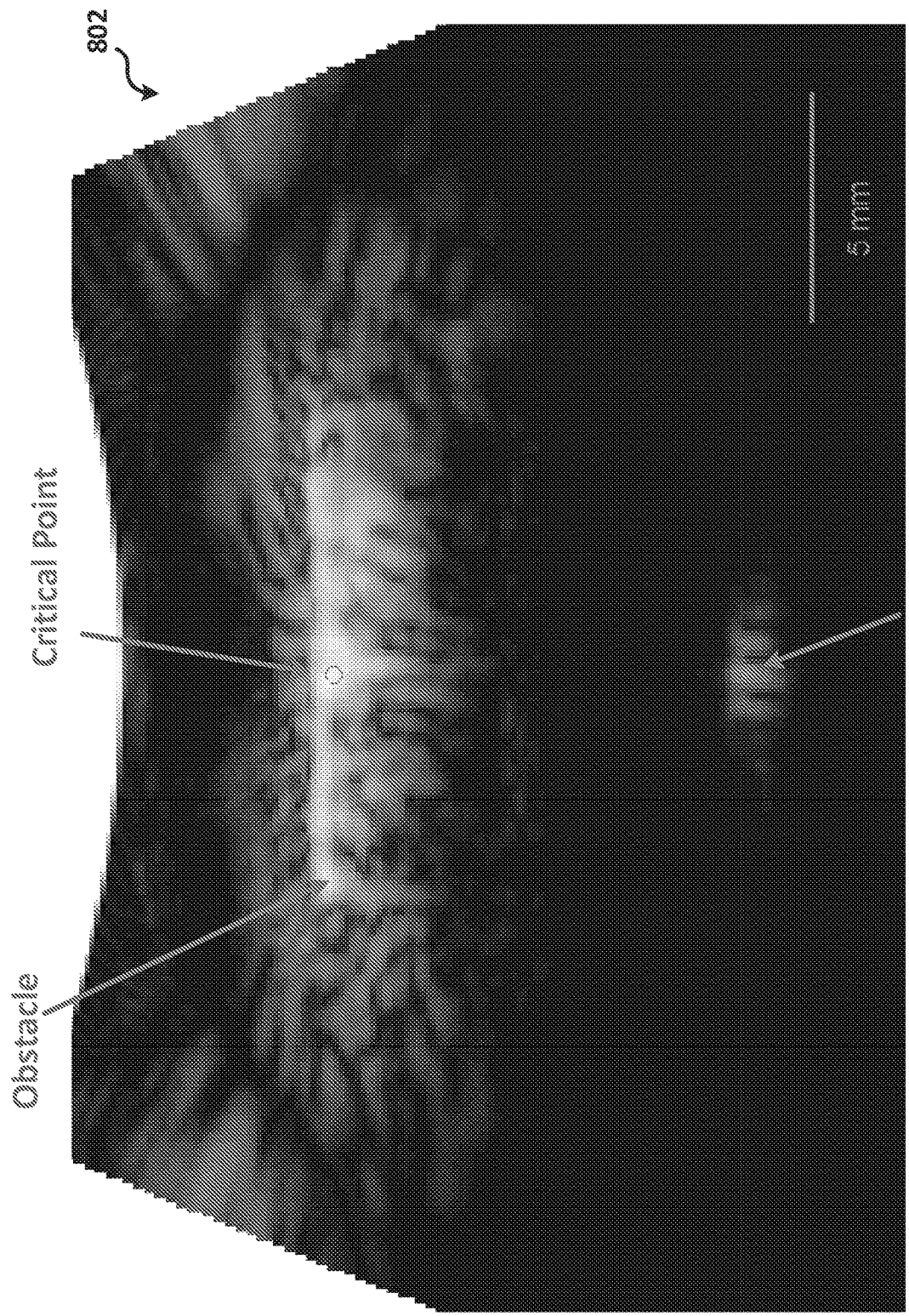
FIG. 11 is a geometrically focused ultrasound image generated by single transmit focus imaging of the system of FIG. 10.

FIG. 11 illustrates a first STF image 802 generated from an STF beam geometrically focused using the target point and critical point locations identified in the SA image. The geometric focusing algorithm ignored aberrations due to the obstacle in generating the first STF image 802. The echogenicity of the first STF image 802 was characterized at the target and critical points.

Compared to the SA image of FIG. 10, the first STF image 802 appears brighter (−20.4 dB versus −25.9 dB). The comparison shows that geometrically-focused STF imaging can enhance the relative echogenicity of the target point in the target region in the same dynamic range compared to SA imaging. The echogenicity in the skull region appeared to be proportional to the incident power caused by the transmit focus. The reflection from the median of the skull appeared to be dominant with the maximum echogenicity at x=−0.2 mm (in the lateral direction) with a range of [−6, 0] dB for x∈[−0.65, 0.9] mm.

Initial propagation operators $H_T^{(0)}$ and $H_C^{(0)}$ were computed based on geometric focusing and used to initiate a refocusing algorithm. For example, a focused data matrix was estimated from the channel data of the first SA image 802, and eigenvalue decomposition was used to determine the initial propagation operators. An initial optimal solution $u_{opt}^{(0)}$ was generated, for example, by Equation 5 and was tested using STF imaging. Additional optimal solutions $u_{opt}^{(i)}$ may be generated iteratively based on channel data from such additional imaging.

FIG. 12 illustrates a second STF 804 image after one iteration of the refocusing algorithm (or one iteration of solving the optimization problem). The echogenicity at the target point was improved slightly to −18.9 dB (compared to brighter −20.4 dB versus −25.9 dB of geometrically focused STF imaging and SA imaging, respectively). The echogenicity near the median of the skull, x∈[1.4, 2.1] mm, was dramatically reduced with an average of −11.2 dB compared to a maximum at x=−3.1 mm.

Figure 13:
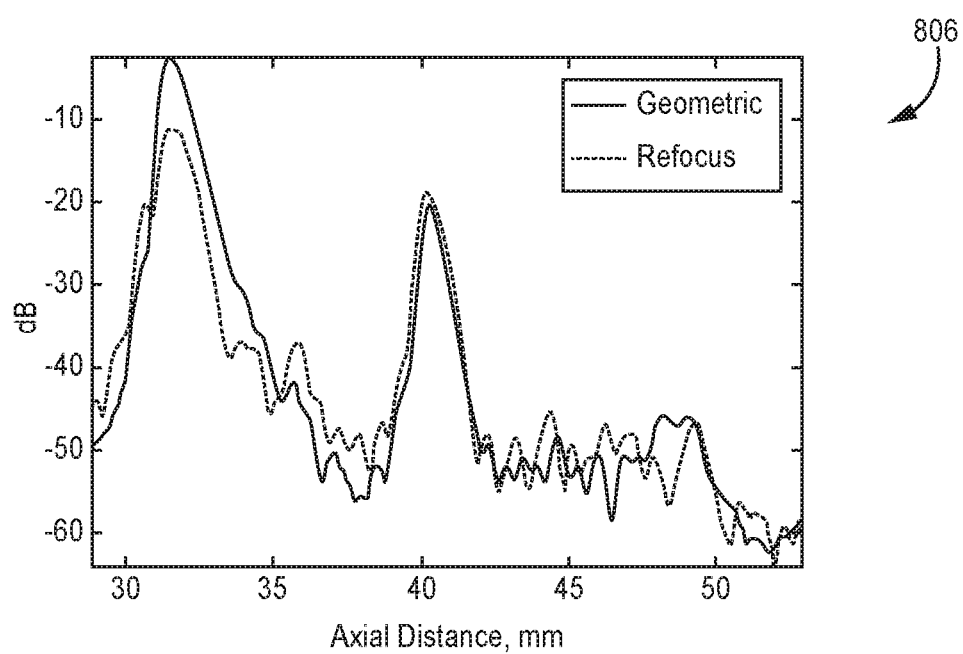
FIG. 13 is a plot of pulse-echo data comparing image data of the ultrasound images of FIG. 11 and FIG. 12.

The differences in echogenicity of the skull in the first and second STF images 802, 804 may be appreciated by the plot 806 of FIG. 13, which illustrates echogenicity along an axial line that passes through the target point in the first STF image 802 (geometric) and in the second STF image (refocus) 804. Change in echogenicity upon refocusing can be indicative of a change in incident power from the transmit beam, as discussed in J R Ballard, A J Casper, Y Wan, and E S Ebbini. "Adaptive Transthoracic Refocusing of Dual-Mode Ultrasound Arrays," IEEE TRANSACTIONS ON BIOMEDICAL ENGINEERING, 57(1):93-102, January 2010, which is incorporated herein by reference. For therapeutic tFUS, the refocused beam of ultrasound energy should have improved heating rate at the target point while reducing the heating rate at and around the median of the skull.

Various SA images 808 were generated to show one manner of providing control points for the virtual arrays as shown in FIG. 14, which provides a montage of grayscale images with a 10 dB dynamic range formed from the same SA channel data used to form the first SA image 802 (FIG. 10). Each of the images 808 was formed from 1 element transmitting and all 32 elements receiving 32 transmissions (Element 1 (top left), . . . , Element 32 (bottom right)). The dynamic range was reduced compared to first SA image 802 to allow for a visual demonstration of the virtual element (array) concept. For each transmitting element, the bright region highlights the segment of the skull that intersects with the transmit pattern. The extent of each of these regions defines two virtual elements on either side of the skull surface. As illustrated by the images 808, these regions can be extracted easily and used in defining the propagation operators needed by a 3-step algorithm utilizing virtual arrays.

The bright regions shown in the images 808 appear to be consistent with the intersections between the directivity patterns and the skull shown in FIGS. 11 and 12.

Example 2

Ex vivo experiments to verify the operation of an image-based wideband transcranial refocusing algorithm were conducted. A dual-mode ultrasound array (DMUA) prototype and supporting real-time imaging platform were used for the acquisition and processing of refocusing beams through ex vivo skull samples. The algorithm utilized pre-beamforming DMUA echo data to perform optimal refocusing in multiple frequency bands within the transducer bandwidth based on user selection of the target and any critical points on the skull where the exposure was to be minimized. Hydrophone measurements were performed in a water tank with and without the skull in the path of the beam. The focusing gain had non-monotonic frequency dependence for any target point. Moreover, the focusing gain profiles varied considerably between different target points. In the former case, the measurements were performed with and without refocusing. Additional experimental verification was obtained using ex vivo skull samples embedded in tissue-mimicking phantoms. Transient temperature rises at the target location (thermocouple junction) were recorded with and without optimal refocusing. The results from both setups demonstrated the increase in focusing gain at the target location and its frequency dependence. Real-time, site-specific refocusing allowed for synthesizing refocused tFUS beams with the maximum operating bandwidth allowable by the transmission characteristics of the skull to the target point(s).

Ex vivo results are shown that characterize the broadband transmissions of the tFUS beam through rodent skull samples, which demonstrated that different target points had significantly different transmission profiles. Refocusing profiles in the frequency range of 1.9-5 MHz are shown, which demonstrate the restoration of focusing gain exhibiting strong frequency dependence.

Materials and Methods

Dual-Mode Ultrasound Array System. The geometry and details of the DMUA prototype used are described in Alyona Haritonova, Dalong Liu, and Emad S Ebbini, "In Vivo application and localization of transcranial focused ultrasound using dual-mode ultrasound arrays," IEEE Trans. UFFC., vol. 62, pp. 2031-2042, 2015, which is incorporated by reference herein in its entirety. The DMUA prototype was used to image and deliver tFUS beams in the frequency range of 1.9 to 5.0 MHz. Two DMUA imaging modes were used:

1) Synthetic Aperture Imaging: Images are formed using a full synthetic aperture technique with two-way (transmit/receive) dynamic focusing as described in Y Wan and E S Ebbini, "Imaging with concave large-aperture therapeutic ultrasound arrays using conventional synthetic-aperture beamforming," IEEE Trans. UFFC, vol. 55, no. 2, pp. 368-383, February 2008. The current system is capable of collecting and real-time beamforming of SA echo data at approximately 30 fps. It also provides real-time access to pre-beamformed SA data for refocusing.

2) Single-Transmit Focus Imaging: This mode as described in E. S. Ebbini, H. Yao, and A. Shrestha, "Dual-mode ultrasound arrays for image-guided surgery," Ultrasonic Imaging, vol. 28, pp. 65-82, April 2006, allows for the use of the candidate tFUS therapy beam at diagnostic exposure levels, i.e., sub-μsec pulses and MI values consistent with diagnostic beams. It provides nondestructive feedback of focusing gain and possible interactions with tissues in the path of the tFUS beam, such as the skull portion in the path of tFUS to the target in this case.

Image-guided Application of tFUS. The 3D imaging mode based on SA-mode DMUA imaging as described in D. Liu, K. Schaible, W. Low, and E. S. Ebbini, "Three-dimensional image guidance for transcranial focused ultrasound therapy," in 2017 IEEE 14$^{th}$ International Symposium on Biomedical Imaging (ISBI 2017), April 2017, pp. 916-919, was used. In this imaging mode, the DMUA was used to collect SA frames while mechanically moving the imaging slice using a synchronized 3-axis motor. Rendering of the collected 3D data allowed for the identification of important landmarks on the surface of the skull. In particular, the bregma, lambda and medial suture lines where seen exquisitely in C-mode images. This allowed for placing the DMUA repeatedly at any target location with respect to the bregma and medial suture lines. This capability facilitated carrying out the validation experiments, which were run over hours and on different days to complete the data sets.

Figure 17A:
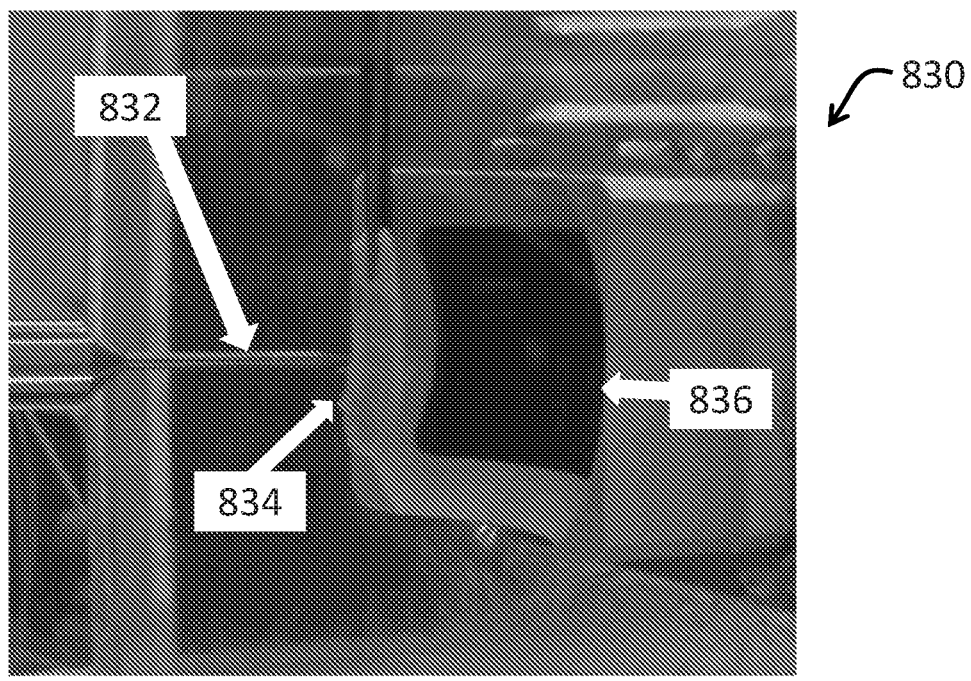
FIGS. 17A-B are an image and a diagram, respectively, showing experimental setups of a water tank (A) and tissue-mimicking phantom (B) experiments.

Water Tank Experiments. A Wideband 0.2 mm needle hydrophone 832 (Onda Corp, Sunnyvale, Calif.) of operating frequency range from 0.5 to 20 MHz was used to characterize the tFUS beam transmission through the skull 834 as shown in photo image 830 of FIG. 17A. The tFUS beams were generated at a set of 32 discrete frequencies within the transducer bandwidth of the DMUA 836, covering the frequency range of 1.9-5.0 MHz. At every operating frequency, single point hydrophone measurements were performed at different target locations distal to the skull. In addition, hydrophone scans were performed in a plane parallel to the surface of the array (40 mm from its apex). These scans were performed with and without the skull in the path of the beam. With the skull present, the scans were repeated with and without refocusing for the various target points.

Figure 17B:
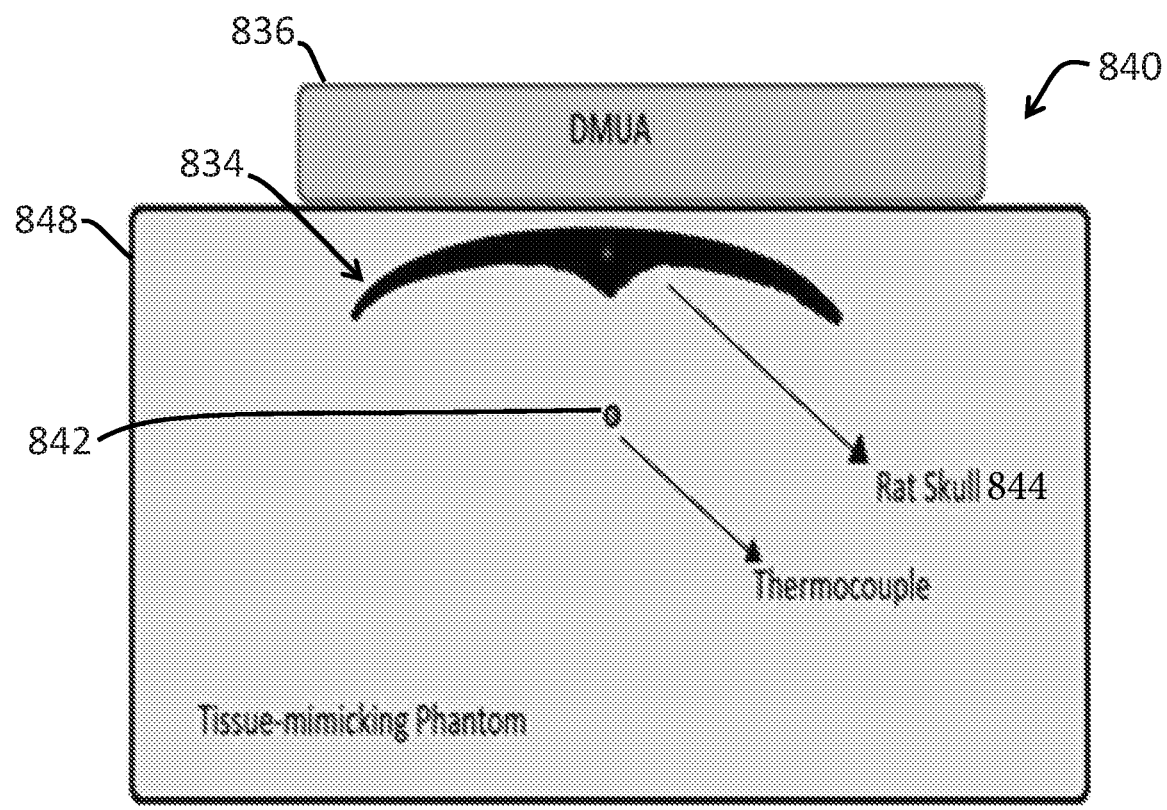
Figure 18:
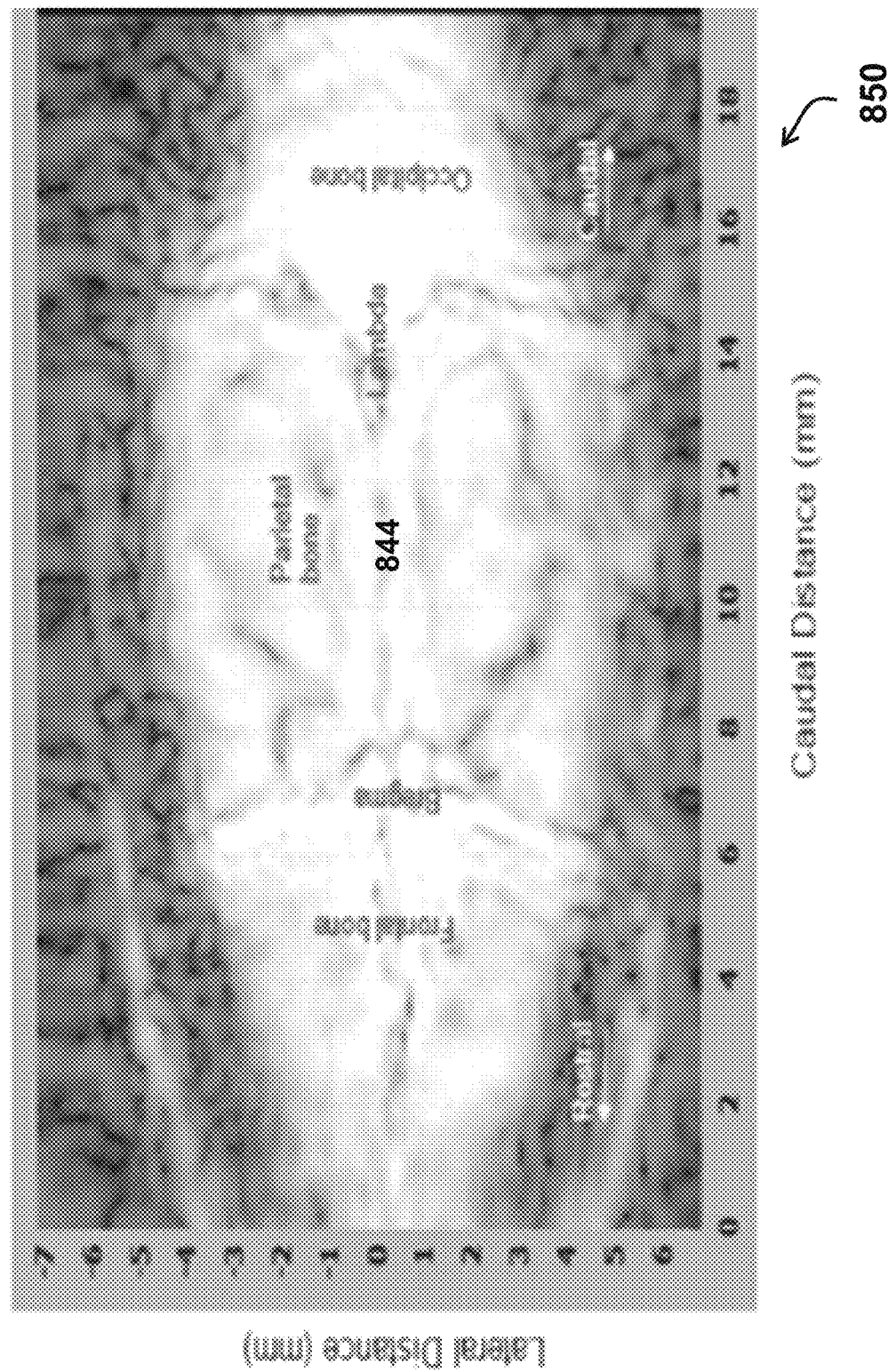
FIG. 18 is an image showing a three-dimensional volume scan of the skull.

Tissue-Mimicking Phantom Experiments. Tissue-mimicking phantoms, or samples, containing ex vivo rodent skull samples were used to evaluate the effect of refocusing on heating efficiency at various target points using DMUA 836. FIG. 17B shows a diagram 840 of the embedded skull 834 near the top of the tissue-mimicking phantom 848 to simulate a thin scalp layer. The positions of the target points were chosen corresponded to what was used during in vivo experiments. After identifying the dorsal aspect of the skull 844 based on the rendering of a 3D volume scan image 850 shown in FIG. 18, a fine diameter (200 μm) T-type thermocouple 842 in the phantom 848 underneath the skull 844 was inserted. The shaft of the needle was perpendicular to the DMUA imaging slice. The junction of the thermocouple 842 was closest to the geometric focus of the DMUA 836 and used as a target point in the refocusing experiments. The thermocouple temperature was measured at a rate of 100 Hz using an HP 34970A data acquisition unit.

Image-Based Transcranial Refocusing. The objective of the refocusing algorithm used was to optimize the tFUS beam to improve the focusing gain at selected target (control) points in real time while minimizing exposure to one or more critical points on the surface of the skull. The algorithm runs automatically once the user has identified the target and critical points on SA imaging according to the following procedure:

- At each operating frequency, the RF echo data corresponding to the target and critical points are extracted from channel data.
- For each point, a region of interest (RoI) is defined by $R_{m,n}^{\{min,max\}} = R_{m,n} \mp R$, where $R_{m,n}$ is the distance between the selected point m and each DMUA element n (n=1, 2, ..., N). The radius of the RoI, R, should be larger than the expected spread in arrival times due to skull aberrations.
- The channel data associated with the target point define a focusing data matrix (FDM), which provides a measure of focusing gain and coherence through eigenvalue decomposition of its Gramian.
- The eigenvectors of the FDM provide updated excitation vectors to maintain or improve focusing gain.
- The data matrix associated with each critical point contribute to a weighting matrix designed to minimize exposure at said critical point.
- The propagation operator vector from the DMUA elements to a target point $\vec{r}_t$ in the imaging field of view of the DMUA is given by $h_t = [h_1(\vec{r}_t), h_2(\vec{r}_t), \ldots, h_N(\vec{r}_t)]$, and to a critical point $\vec{r}_c$ is given by $h_c = [h_1(\vec{r}_c), h_2(\vec{r}_c), \ldots, h_N(\vec{r}_c)]$, where $h_n(\vec{r})$ represents the directivity of the DMUA $n_{th}$ element at the point $\vec{r}$.
- The refocused array excitation vector ($u_{opt}$). The $u_{opt} = W_c^{-1} h_t^* (h_t W_c^{-1} h_t^*)^{-1} p_t$, where $W_c = h_c h_c^* + \gamma I$ with $\gamma$ and I are an appropriately chosen regularization parameter and identity matrix, respectively.

This procedure was repeated for each operating frequency of the 32 frequency bands in the 1.9-5 MHz range. Furthermore, the refocused excitation vector of each frequency was pushed into the ultrasound system and used to generate a tFUS beam.

Results and Discussion

Figure 19:
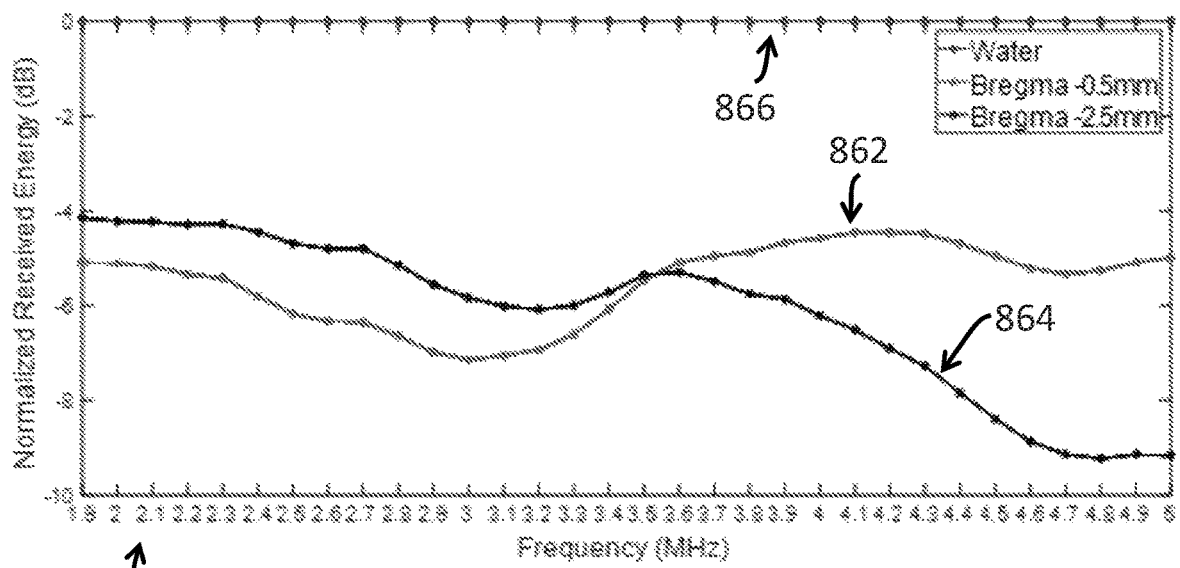
FIG. 19 is a plot showing acoustic energy after two different locations of the same skull.

Water Tank Experiments. FIG. 19 is a plot 860 of normalized received energy (dB) versus frequency (MHz) showing a first profile 862 and a second profile 864 of focusing gain loss as a function of frequency for two different target points at bregma −0.5 mm and bregma −2.5 mm, respectively. The curves were obtained by computing the energy in the signal received by the hydrophone in the presence of the skull with reference to the water-only measurement 866 (on the 0-dB line.) The profiles 862 and 864 can be thought of as transmission efficiency at each target point. Different dependence on frequency was exhibited, in addition to not being monotonic. The curves represent the variation in frequency dependence and may suggest that different frequencies are more efficiently transmitted for a given target. Furthermore, this frequency dependence does not appear to follow a pattern due to the complex dependence on the variable thickness and curvature of the skull region interacting with the FUS beam.

Figure 20:
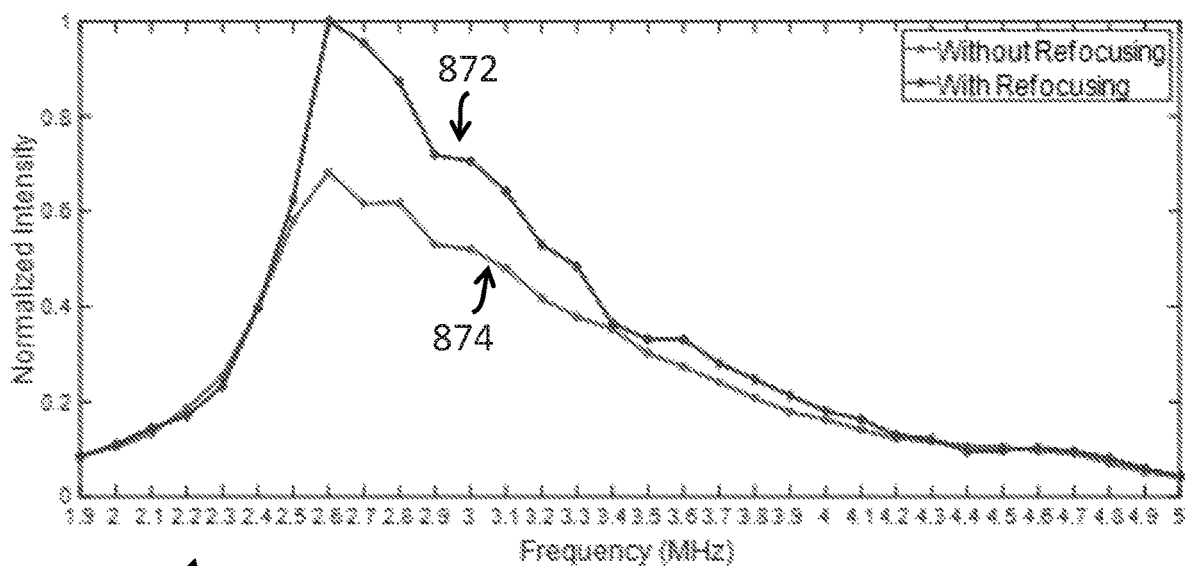
FIG. 20 is a plot showing focal point intensity of skull plane scans.

Hydrophone measurements were also used to evaluate the increase in focusing gain due to refocusing. FIG. 20 is a plot 870 of normalized intensity versus frequency (MHz) showing a first profile 872 and a second profile 874 of focal point intensity values of the scanned planes with and without refocusing at each frequency, respectively. The results are normalized with respect to the maximum focusing gain achieved by refocusing at 2.7 MHz. The results show a significant increase in focusing gain in the frequency range of 2.5-4.1 MHz.

Tissue-Mimicking Phantom Experiments. The goal of these experiments was to demonstrate the effects of refocusing on the improvements in tFUS-induced heating. The 32-channel arbitrary waveform generator was used to generate tFUS beams with increased duty cycles to cause a small increase in temperature as a form of subtherapeutic application of tFUS. At each frequency, the waveforms were programmed as raised-cosine with phase/delay profiles obtained using the refocusing algorithm. The target point was at bregma −3.0 mm and approximately 8 mm behind the skull.

Figure 21A:
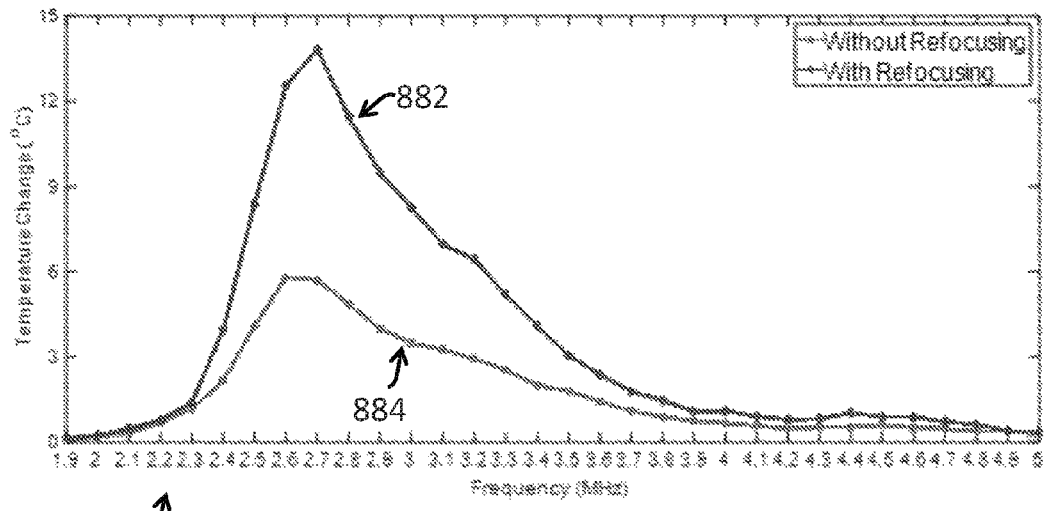
FIGS. 21A-B are plots showing the values of temperature rise (A) and heating rate (B) with and without refocusing.

FIG. 21A is a plot 880 of temperature change (° C.) versus frequency (MHz) showing the maximum temperature achieved due to the applications of the wideband trans-skull ultrasound beams. The temperature values were measured using a thermocouple inserted at the target location below the skull. The temperature rise as a function of frequency was captured in a first profile 882 before refocusing and a second profile 884 after refocusing. The profiles show the improvement in the heating rate in the range of 2.4-3.5 MHz.

Figure 21B:
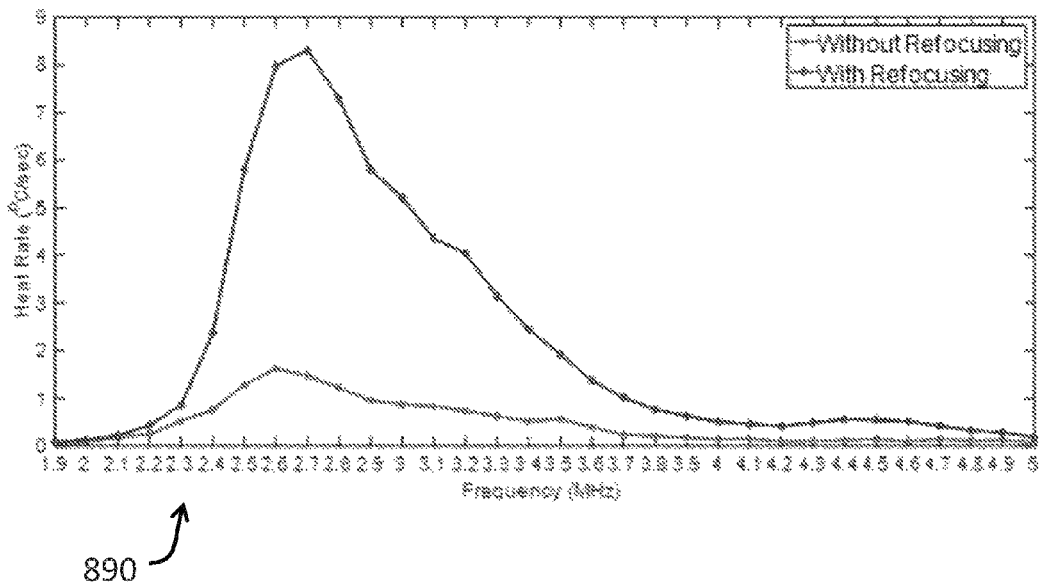

FIG. 21B is a plot 890 of heating rate (° C./sec) versus frequency (MHz) showing results from the same set of phantom experiments represented in terms of the initial heating rate, which serves as a measure of intensity gain in a small volume around the thermocouple as opposed to the point measurements provided by the hydrophone shown in the plot 870 of FIG. 20. These measurements in plot 890 may represent a relevant intensity measurement in thermal therapy, which may be more useful in some cases over other measurements. Improvement in refocusing gain is improved throughout the frequency band. The results were not normalized with respect to the bandwidth efficiency of the DMUA.

The focusing gain profiles may also reflect the transducer bandwidth. The results demonstrate the advantage of refocusing at every frequency in the available spectrum.

All patents, patent documents, and references cited herein are incorporated in their entirety as if each was incorporated separately. This disclosure has been provided with reference to illustrative embodiments and is not meant to be construed in a limiting sense. As described previously, one skilled in the art will recognize that other various illustrative applications may use the techniques as described herein to take advantage of the beneficial characteristics of the apparatus and methods described herein. Various modifications of the illustrative embodiments, as well as additional embodiments of the disclosure, will be apparent upon reference to this description.

All scientific and technical terms used herein have meanings commonly used in the art unless otherwise specified. The definitions provided herein are to facilitate understanding of certain terms used frequently herein and are not meant to limit the scope of the present disclosure.

Unless otherwise indicated, all numbers expressing feature sizes, amounts, and physical properties used in the specification and claims are to be understood as being modified in all instances by the term "about." Accordingly, unless indicated to the contrary, the numerical parameters set forth in the foregoing specification and attached claims are approximations that can vary depending upon the desired properties sought to be obtained by those skilled in the art utilizing the teachings disclosed herein.

The recitation of numerical ranges by endpoints includes all numbers subsumed within that range (e.g. 1 to 5 includes 1, 1.5, 2, 2.75, 3, 3.80, 4, and 5) and any range within that range. Herein, the terms "up to" or "no greater than" a number (e.g., up to 50) includes the number (e.g., 50), and the term "no less than" a number (e.g., no less than 5) includes the number (e.g., 5).

Unless otherwise noted, all parts, percentages, ratios, etc. are by weight. These abbreviations are used herein: wt=weight, ° C.=degrees Celsius, and ppm=parts per million.

The terms "coupled" or "connected" refer to elements being attached to each other either directly (in direct contact with each other) or indirectly (having one or more elements between and attaching the two elements). Either term may be modified by "operatively" and "operably," which may be used interchangeably, to describe that the coupling or connection is configured to allow the components to interact to carry out at least some functionality (for example, a mobile user device may be operatively coupled to a cellular network transmit data to or receive data therefrom).

Reference to "one embodiment," "an embodiment," "certain embodiments," or "some embodiments," etc., means that a particular feature, configuration, composition, or characteristic described in connection with the embodiment is included in at least one embodiment of the disclosure. Thus, the appearances of such phrases in various places throughout are not necessarily referring to the same embodiment of the disclosure. Furthermore, the particular features, configurations, compositions, or characteristics may be combined in any suitable manner in one or more embodiments.

The words "preferred" and "preferably" refer to embodiments of the disclosure that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the disclosure.

As used in this specification and the appended claims, the singular forms "a," "an," and "the" encompass embodiments having plural referents, unless the content clearly dictates otherwise. As used in this specification and the appended claims, the term "or" is generally employed in its open-ended sense including "and/or" unless the content clearly dictates otherwise.

As used herein, "have," "having," "include," "including," "comprise," "comprising" or the like are used in their open-ended sense, and generally mean "including, but not limited to." It will be understood that "consisting essentially of" "consisting of," and the like are subsumed in "comprising," and the like.

The term "and/or" means one or all of the listed elements or a combination of any two or more of the listed elements.

The phrases "at least one of," "comprises at least one of," and "one or more of" followed by a list refers to any one of the items in the list and any combination of two or more items in the list.

The invention claimed is:

1. A dual mode ultrasound transducer system, comprising:
an array of ultrasound transducer elements configured to deliver multiband ultrasound energy to a tissue volume including a target region and to receive echo ultrasound energy from the tissue volume, wherein the tissue volume includes an ultrasound distorting obstacle in an imaging field of view of the array and wherein the target region is disposed distal to the obstacle such that at least a portion of the ultrasound energy delivered to one or more target points in the target region must pass through the obstacle; and a control apparatus comprising at least one processor configured to:

generate initial image data of the tissue volume in the imaging field of view using the array of ultrasound transducer elements;

identify the one or more target points in the target region and one or more critical points associated with the obstacle in the tissue volume;

synthesize excitation waveforms for driving the array of ultrasound transducer elements based on the one or more target points and the one or more critical points;

generate focused image data of the target region using the excitation waveforms to drive the array of ultrasound transducer elements, the focused image data comprising measurements in a plurality of different frequency bands using the ultrasound transducer elements, the focused image data comprising information associated with the one or more target points and information associated with the one or more critical points;

determine focusing gains based on the focused image data, the focusing gains including at least a target focusing gain associated with one of the target points and a critical focusing gain associated with one of the critical points;

in response to determining that both the target focusing gain is no less than a minimum threshold and that the critical focusing gain is no greater than a maximum threshold, configure delivery of refocused ultrasound energy to the tissue volume including the one or more target points in the target region based on the excitation waveforms for imaging or therapy; and in response to determining that either the target focusing gain is less than the minimum threshold or that the critical focusing gain is greater than the maximum threshold, synthesize an iteration of the excitation waveforms based on the focused image data, and generate refocused image data comprising a plurality of multiband focused data matrices each formed from a different band of multiband channel data using the iteration of the excitation waveforms to drive the array of ultrasound transducer elements.

2. The system of claim 1, wherein the control apparatus is configured to determine focusing gain by measuring a response to delivering subtherapeutic focused ultrasound energy at one or more control points.

3. The system of claim 2, wherein the control apparatus is configured to determine focusing gain by measuring echogenicity at the one or more control points.

4. The system of claim 2, wherein the subtherapeutic focused ultrasound energy is delivered for a duration from about 10 milliseconds to about 100 milliseconds to produce localized heating in the tissue volume, and the control apparatus is configured to measure heating using ultrasound thermography at the one or more control points.

5. The system of claim 2, wherein the subtherapeutic focused ultrasound energy is delivered for a duration from about 10 microseconds to about 100 microseconds to produce localized cavitation in the tissue volume, and the control apparatus is configured to measure cavitation using bubble oscillations or cavitation noise at the one or more control points.

6. The system of claim 2, wherein the subtherapeutic focused ultrasound energy is delivered for a duration from about 100 microseconds to about 1000 microseconds to provide acoustic radiation force to produce tissue displacements in the tissue volume, and the control apparatus is configured to measure tissue displacement using speckle tracking at the one or more control points.

7. The system of claim 1, wherein the initial image data is generated using a first field of view and the focused image data is generated using a second field of view narrower than the first field of view.

8. The system of claim 1, wherein the initial image data is generated using synthetic aperture (SA) imaging or coded synthetic aperture (cSA) imaging.

9. The system of claim 1, wherein the focused image data is generated using multiple transmit-focus (MTF) imaging or coded multiple transmit-focus (cMTF) imaging.

10. The system of claim 1, wherein the focused image data is generated in the form of the focused data matrices each comprising truncated channel data.

11. The system of claim 10, wherein the control apparatus is configured to generate focused image data using a sequence of multiple transmit-focus (MTF) or coded multiple transmit focus (cMTF) image acquisitions and acquire multiple focusing data matrices associated with one or more of the target points and the critical points.

12. The system of claim 10, wherein the control apparatus is configured to generate focused image data by spatially filtering a channel data matrix to generate the focused data matrices associated with the one or more target points and one or more critical points.

13. The system of claim 12, wherein the control apparatus is configured to spatially filter the channel data matrix using axi-lateral filtering of channel data, pre-beamforming or post-beamforming of a full aperture or sub-aperture, to compress channel data and improve axial resolution, lateral resolution, or both.

14. The system of claim 13, wherein the control apparatus is configured to spatially filter the channel data matrix using inverse spatial filtering pre- and post-beamforming.

15. The system of claim 12, wherein the control apparatus is configured to spatially filter the channel data matrix using narrowband filtering using one or more of an infinite impulse response (IIR) filter, a finite impulse response (FIR) filter, a low-order Butterworth filter, and a sliding discrete Fourier transform (DFT) filter.

16. The system of claim 12, wherein the control apparatus is configured to spatially filter the channel data matrix using one or more of a digitally programmable analog filter, a surface acoustic wave device, and a mixed analog-digital transmit-receive network.

17. The system of claim 1, wherein the control apparatus is configured to determine focusing gain based on the refocused image data.

18. The system of claim 1, wherein the control apparatus is configured to synthesize the iteration of the excitation waveforms to increase target focusing gain associated with the one or more target points and reduce critical focusing gain associated with the one or more critical points.

19. The system of claim 1, wherein the control apparatus is configured to synthesize iterations of the excitation waveforms until:

both the target focusing gain is no less than the minimum threshold and the critical focusing gain is no greater than the maximum threshold; or one or both of the target focusing gain and the critical focusing gain converge in consecutive iterations.

20. A dual mode ultrasound transducer system, comprising:

an array of ultrasound transducer elements configured to deliver multiband ultrasound energy to a tissue volume including a target region and to receive echo ultrasound energy from the tissue volume, wherein the tissue volume includes an ultrasound distorting obstacle in an imaging field of view of the array and wherein the target region is disposed distal to the obstacle such that at least a portion of the ultrasound energy delivered to one or more target points in the target region must pass through the obstacle; and a control apparatus comprising at least one processor configured to:

generate initial image data of a tissue volume in an imaging field of view using the array of ultrasound transducer elements, determine one or more critical points associated with the obstacle based on the initial image data, wherein the critical points are to be avoided when propagating focused ultrasound energy to the target region;

determine one or more transmission points associated with the obstacle, each transmission point being different than any of the critical points, wherein the transmission points are to be used for propagating focused ultrasound energy to the target region;

generate focused image data of the tissue volume including the target region and the obstacle using the array of ultrasound transducer elements, the focused image data comprising information associated with one or more of the transmission points for a plurality of different frequency bands within a bandwidth of the array of ultrasound transducer elements;

determine one or more efficient frequency bands for one or more of the transmission points based on the focused image data; and synthesize excitation waveforms and generate refocused image data comprising a plurality of multiband focused data matrices each formed from a different band of multiband channel data for delivering refocused ultrasound energy to the one or more target points in the target region based on one or more of the transmission points and one or more associated efficient frequency bands.

21. The system of claim 20, wherein the obstacle has non-uniform ultrasound propagation characteristics, wherein the one or more transmission points are associated with higher focusing gain compared to focusing gain for one or more of the critical points.

22. The system of claim 20, wherein the obstacle comprises at least a portion of one or more of a skull, a rib cage, a spinal vertebra, and a surgical scar.

23. A dual mode ultrasound transducer system, comprising:

an array of ultrasound transducer elements configured to deliver multiband ultrasound energy to the tissue volume including a target region and to receive echo ultrasound energy from the tissue volume, wherein the tissue volume includes an ultrasound distorting obstacle in an imaging field of view of the array and wherein the target region is disposed distal to the obstacle such that at least a portion of the ultrasound energy delivered to one or more target points in the target region must pass through the obstacle;

generate initial image data of a tissue volume in an imaging field of view using the array of ultrasound transducer elements, determine one or more first virtual elements of a first virtual array associated with a distal surface of the obstacle based on the initial image data;

determine one or more second virtual elements of a second virtual array associated with a proximal surface of the obstacle based on the initial image data;

estimate a first propagation operator between the one or more of the target points in the target region and the one or more second virtual elements of the first virtual array;

estimate a second propagation operator between the one or more first virtual elements and the one or more second virtual elements based on the initial image data;

estimate a third propagation operator between the one or more second virtual elements and one or more of the ultrasound transducer elements of the array; and configure delivery of refocused ultrasound energy to the one or more target points in the target region by solving an optimization problem on a cascade of the first, second, and third propagation operators or solving an optimization problem for each of the first, second, and third propagation operators;

wherein the control apparatus is configured to deliver the refocused ultrasound energy by synthesizing excitation waveforms and generating refocused image data comprising a plurality of multiband focused data matrices each formed from a different band of multiband channel data for delivering the refocused ultrasound energy.

24. The system of claim 23, wherein each of the virtual arrays is defined by a point spread function of the array of ultrasound transducer elements at a surface of the obstacle.

25. The system of claim 23, wherein each of the virtual arrays is defined by a point spread function of one or more sub-apertures of the array at a surface of the obstacle.

26. The system of claim 23, wherein the control apparatus is configured to determine the one or more first virtual elements by determining a control point associated with the distal surface of the obstacle for each of the ultrasound transducer elements of the array to determine the one or more second virtual elements.

27. The system of claim 23, wherein the control apparatus is configured to determine the one or more second virtual elements by determining a control point associated with the proximal surface of the obstacle for each of the ultrasound transducer elements of the array to determine the one or more first virtual elements.

28. The system of claim 23, wherein each point in the first virtual array is associated with a point in the second virtual array disposed on an opposite side of the obstacle.

29. The system of claim 23, wherein the obstacle comprises at least a portion of a skull having an interior surface associated with the first virtual array and an exterior surface associated with the second virtual array.

* * * * *